United States Patent
Ma et al.

(10) Patent No.: US 10,759,765 B2
(45) Date of Patent: Sep. 1, 2020

(54) HETEROCYCLIC CARBOXYLIC ACID AMIDE LIGAND AND APPLICATIONS THEREOF IN COPPER CATALYZED COUPLING REACTION OF ARYL HALOGENO SUBSTITUTE

(71) Applicant: CE Pharm CO., LTD., Taizhou (CN)

(72) Inventors: Dawei Ma, Shanghai (CN); Wei Zhou, Shanghai (CN); Mengyang Fan, Shanghai (CN); Haibo Wu, Shanghai (CN); Junli Yin, Shanghai (CN); Xi Jiang, Shanghai (CN); Yuntong Zhai, Shanghai (CN); Songtao Niu, Shanghai (CN)

(73) Assignee: CE Pharm Co., Ltd., Taizhou, Zhejiang Province (CN)

( * ) Notice: Subject to any disclaimer, the term of this patent is extended or adjusted under 35 U.S.C. 154(b) by 0 days.

(21) Appl. No.: 16/093,688

(22) PCT Filed: Apr. 14, 2017

(86) PCT No.: PCT/CN2017/080626
§ 371 (c)(1),
(2) Date: Jan. 10, 2019

(87) PCT Pub. No.: WO2017/177979
PCT Pub. Date: Oct. 19, 2017

(65) Prior Publication Data
US 2019/0127337 A1    May 2, 2019

(30) Foreign Application Priority Data
Apr. 15, 2016  (CN) .......................... 2016 1 0236714

(51) Int. Cl.
| | | |
|---|---|---|
| C07D 241/02 | (2006.01) |
| B01J 31/22 | (2006.01) |
| C07C 231/02 | (2006.01) |
| C07C 233/00 | (2006.01) |
| C07D 207/32 | (2006.01) |
| C07D 209/08 | (2006.01) |
| C07D 209/12 | (2006.01) |
| C07D 213/06 | (2006.01) |
| C07D 235/08 | (2006.01) |
| C07D 239/02 | (2006.01) |
| C07D 277/02 | (2006.01) |
| C07D 277/62 | (2006.01) |
| C07D 307/02 | (2006.01) |
| C07D 307/78 | (2006.01) |
| C07C 209/60 | (2006.01) |

(52) U.S. Cl.
CPC .......... *C07D 241/02* (2013.01); *B01J 31/22* (2013.01); *C07C 231/02* (2013.01); *C07C 233/00* (2013.01); *C07D 207/32* (2013.01); *C07D 209/08* (2013.01); *C07D 209/12* (2013.01); *C07D 213/06* (2013.01); *C07D 235/08* (2013.01); *C07D 239/02* (2013.01); *C07D 277/02* (2013.01); *C07D 277/62* (2013.01); *C07D 307/02* (2013.01); *C07D 307/78* (2013.01); *C07C 209/60* (2013.01)

(58) Field of Classification Search
CPC .................................................... C07D 241/02
See application file for complete search history.

(56) References Cited

PUBLICATIONS

Fan, et al. Angew. Chem. Int. Ed. 2016, 55, 6211-6215. (Year: 2016).*
Sambiagio, Carlo et al., "Picolinamides as Effective Ligands for Copper-Catalysed Aryl Ether Formation: Structure-Activity Relationships, Substrate Scope and Mechanistic Investigations," Chem. Eur. J. 2014, vol. 20, pp. 1-11.
Damkaci, F., Alawaed, A., Vik, E., N-Picolinamides as ligands for Ullmann-type C—N coupling reactions, Tetrahedron Letters (2016), doi: http://dx.doi.org/10.1016/j.tetlet.2016.04.017.
Liu, Xianghao, et al. "Highly Efficient Copper-Catalyzed O-Arylation Using Readily Available (S)—N-Methylpyrrolidine-2-Carboxamide as the Ligand," Synlett 2008, No. 2, pp. 0221-0224.
Otto, Nicola, et al., "Screening of ligands for the Ullmann synthesis of electron-rich diaryl ethers," Beilstein J. Org. Chem. 2012, vol. 8, pp. 1105-1111 & Supporting Information, pp. S1-S35.
Evindar, Ghotas, et al., "Parallel Synthesis of a Library of Benzoxazoles and Benzothiazoles Using Ligand-Accelerated Copper-Catalyzed Cyclizations of ortho-Halobenzanilides," J. Org. Chem. 2006, vol. 71, pp. 1802-1808 & Supporting Information, pp. S1-S44.
Yong, Fui-Fong, et al., "Efficient ligand-free copper-catalyzed N-arylation of amides with aryl halides in water," Tetrahedron Letters 2011, Vo. 52, pp. 1169-1172.
Japanese Office Action issued in Japanese patent application No. 2018-554117, dated Dec. 9, 2019 (w/ English translation).
International Search Report issued in International application No. PCT/CN2017/080626, dated Jun. 21, 2017.

(Continued)

Primary Examiner — Shawquia Jackson
(74) Attorney, Agent, or Firm — Faegre Drinker Biddle & Reath LLP

(57) ABSTRACT

Provided are a heterocyclic carboxylic acid amide ligand and applications thereof in a copper catalyzed coupling reaction. Specifically, provided are uses of a compound represented by formula (I), definitions of radical groups being described in the specifications. The compound represented by formula (I) can be used as the ligand in the copper catalyzed coupling reaction of the aryl halogeno substitute, and is used or catalyzing the coupling reaction for forming the aryl halogeno substitute having C—N, C—O, C—S and other bonds.

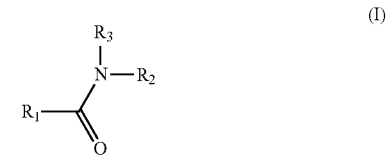

(I)

13 Claims, No Drawings

(56) References Cited

PUBLICATIONS

Habash, M. et al., "Ligand-based modelling followed by synthetic exploration unveil novel glycogen phosphorylase inhibitory leads," Bioorganic & Medicinal Chemistry, vol. 19, No. 16, Jul. 7, 2011, pp. 4746-4771.

Supplementary European search report from European patent application No. 17781955.4, dated Oct. 1, 2019.

Evano, Gwilherm, et al., "Copper-Mediated Coupling Reactions and Their Applications in Natural Products and Designed Biomolecules Synthesis," Chemical, Reviews, vol. 108, No. 8, Aug. 1, 2008 (Aug. 1, 2008), pp. 3054-3131,XP008151521.

Mistry, Shailesh N., et al., "Discovery of a Novel Class of Negative Allosteric Modulator of the Dopamine D Receptor Through Fragmentation of a Bitopic Ligand," J. Med. Chem, vol. 58, No. 17, Aug. 10, 2015, pp. 6819-6843.

Mitra, Aurpon W., et al., "α-Aminoamides as ligands in Goldberg amidations," Tetrahedron Letters 2013, vol. 54, pp. 6580-6583.

\* cited by examiner

HETEROCYCLIC CARBOXYLIC ACID AMIDE LIGAND AND APPLICATIONS THEREOF IN COPPER CATALYZED COUPLING REACTION OF ARYL HALOGENO SUBSTITUTE

CROSS REFERENCE TO RELATED APPLICATIONS

This application is a National Stage of International Application No. PCT/CN2017/080626 filed Apr. 14, 2017, which claims benefit of Chinese Patent Application No. 201610236714.1 filed Apr. 15, 2016, both of which are herein incorporated by reference in their entirety.

FIELD OF THE INVENTION

The present invention relates to the field of organic synthesis. In particular, a copper-catalyzed coupling reaction of aryl halide catalyzed by a heterocyclic carboxylic acid amide ligand, especially a coupling reaction to form C—N, C—O, and C—S bonds is provided in the present invention.

BACKGROUND OF THE INVENTION

Transition metal-catalyzed coupling reaction of aryl halides with suitable nucleophiles, such as organic amines, active methylene compounds, alkynes, phenols, alcohols, thiophenols, sodium sulfinates, sodium sulfide, or phosphates is an effective method to form C—N, C—C, C—O, C—S, and C—P bonds. Generally, aryl iodide and aryl bromide are of higher reactivity, thus can achieve the corresponding coupling reaction when catalyzed by transition metals such as palladium, copper, nickel, etc. Compared with bromine (iodo) aromatic hydrocarbon, chlorination aromatic hydrocarbons are cheaper and of better application prospect, however, C—Cl bond is of high energy (Grushin, V V; Alper, H. Chem. Rev. 1994, 94, 1047.), which makes it difficult for the oxidative addition between C—Cl bond and transition metals. The reaction is not as efficient as the bromide and iodine. The C—N coupling reaction of aryl chlorides catalyzed by palladium and nickel has been reported. The use of large sterically hindered phosphorus ligands to promote the reaction is an effective strategy. In 2005, Hartwig's group has used large steric phosphines with ferrocene structure to successfully complete the coupling reaction of chlorinated aromatic ring or aromatic heterocyclic compound with the primary amine, in which the equivalent of the catalyst and the ligand in the system can be reduced even to one hundred thousandth molar equivalent. For certain aromatic heterocyclic ring substrates, this type of reaction can be achieved at room temperature, which fully demonstrates the high efficiency of the catalyst system. Moreover, the reaction is also compatible with the substituent groups on the benzene ring (Shen, Q.; Shekhar, S Stambuli, J P; Hartwig, J F Angew. Chem. Int. Ed. 2005, 44, 1371.1.

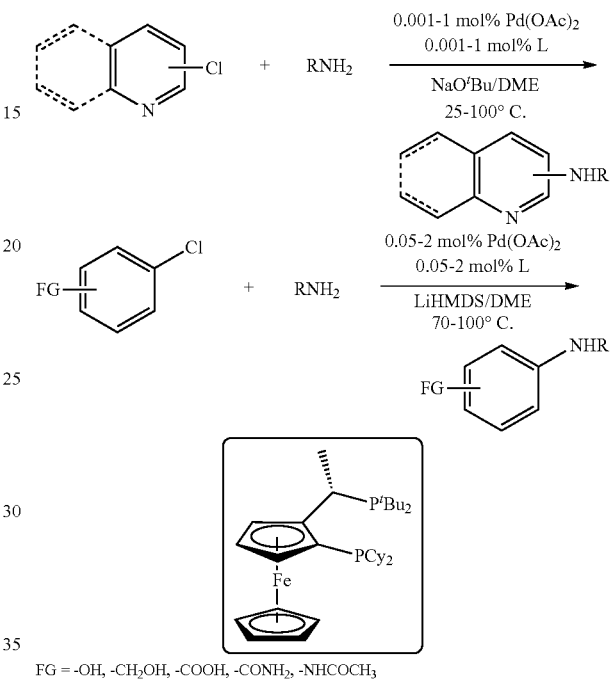

FG = -OH, -CH$_2$OH, -COOH, -CONH$_2$, -NHCOCH$_3$

In 2011, Buchwald's team found that chlorinated aromatics can be coupled to primary amines and secondary amines, respectively by employing different phosphine ligands. The system has broad compatibility with substrates. Besides general aliphatic amines, the heterocyclic aromatic amine can also be subjected to the coupling reaction successfully (Maiti, D.; Fors, B P; Henderson, J L; Nakamura, Y.; Buchwald, S L Chem. Sci. 2011, 2, 57.).

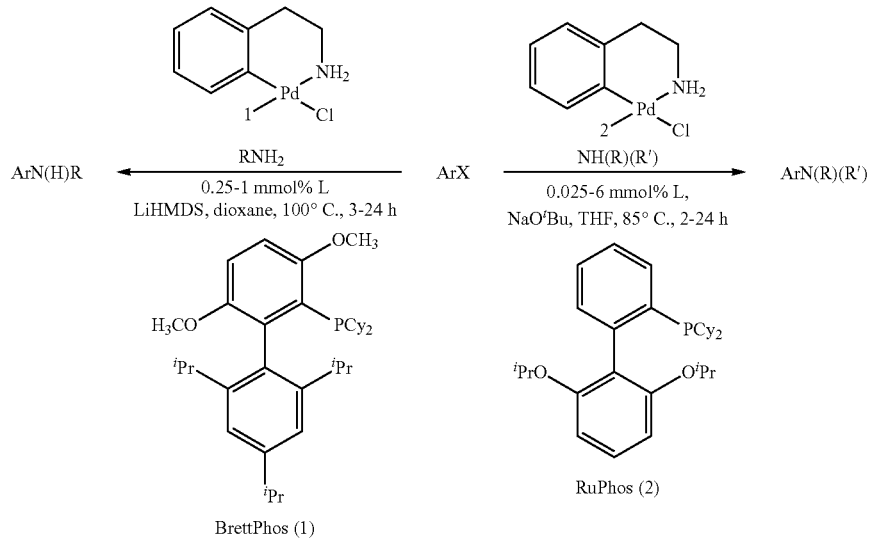

Although palladium and nickel are highly efficient in catalyzing the amination reaction of chlorinated aromatic hydrocarbons, there still are some problems in large-scale applications: 1. in the system, the addition of large sterically hindered, complex phosphine ligands or azacarbene ligands is necessary to promote the reaction; 2. the palladium catalyst is expensive, and the reaction operation required for zero-valent nickel is quite demanding, which to some extent has limited the application thereof. Compared with the above, copper catalysts are inexpensive, stable, and readily available, and the ligands used are in simple structure, which obviously avoids those deficiencies. However, the copper-catalyzed coupling reaction substrates reported so far are mostly limited to iodinated and brominated substrates.

In 2007, Pellón's group has achieved the coupling reaction of aliphatic amine with 2-chlorobenzoic acid under the action of ultrasound by and the promoting effects of the ortho-carboxy group of 2-chlorobenzoic acid, and good yield can be obtained for both primary amine and the secondary amine. However, this method is only effective for ortho-carboxy substituted substrates, which cannot be generally applied (Docampo, M L; Pellón, R F; Estevez-Braun, A.; Ravelo, A G Eur. J. Org. Chem. 2007, 4111). This reaction is essentially a nucleophilic substitution reaction rather than a coupling reaction, and the reaction temperature is very high.

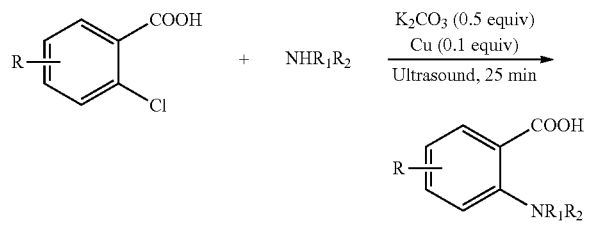

Another report on the Ullmann coupling reaction of chlorinated aromatic hydrocarbons was reported by Taillefer's group. They used 2,2,6,6-tetramethyl-3,5-heptanedione as ligand to achieve the C—O coupling of chlorobenzene and phenols. The major disadvantage of this system is that up to 0.8 equivalents of ligand should be added into the reaction, thus reducing the economical efficiency of the reaction (Xia, N.; Taillefer, M. Chem. Eur. J. 2008, 14, 6037.).

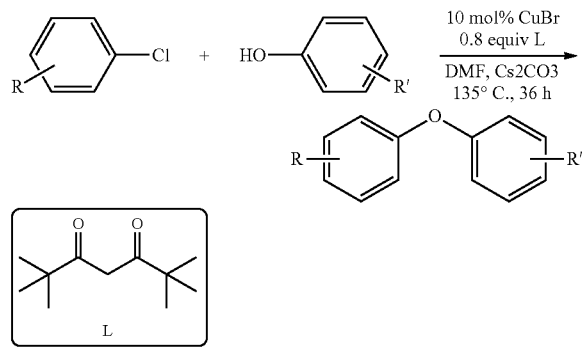

In 2012, Ma Dawei's group has used the oxalic acid 2,6-dimethylphenyl monoamide carboxylic acid as a ligand for copper-catalyzed C—N coupling reaction of aryl iodide or bromine with organic amine (Org. Lett 2012, 14, 3056-3059). Recently, they have successfully applied oxalic diamide ligands designed based on that in the coupling reaction of aryl chlorides, and found that various types of nucleophiles can be used in the reaction, including primary amines, cyclic secondary amines, ammonium hydroxide, phenol, etc. This reaction provides coupled products in a good yield (J. Am. Chem. Soc. 2015, 137, 11942-11945; Org. Lett. 2015, 17, 5934-5937.).

In summary, the copper-catalyzed coupling reaction of aryl chlorides has very important application prospects, and suitable ligands are the key to such reactions. There is still a lack of a catalytic system for copper-catalyzed aryl chloride coupling reactions that is simple to be prepared, suitable for industrial applications that enables efficient reaction.

SUMMARY OF THE INVENTION

It is an object of the present invention to provide a catalytic system that can be used in copper catalyzed coupling reactions of aryl halides, particularly aryl chlorides.

In the first aspect of the present invention, a use of compound of following formula I as a ligand in a copper-catalyzed aryl halide coupling reaction is provided:

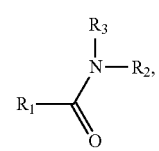

Wherein $R_1$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be monocyclic, multiple-cyclic, spiro or bridged ring structure;

$R^2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be of monocyclic, multiple-cyclic, spiro or bridged ring structure;

$R_3$ is selected from the group consisting of hydrogen, and a substituted or unsubstituted C1-C6 alkyl;

or $R_2$ and $R_3$ together with the connected N atom to form a 3- to 20-membered saturated or unsaturated ring (e.g., a substituted or unsubstituted pyrrole, indole, azole, benzoxazole, and aromatic heterocycle);

wherein the aryl halide is selected from the group consisting of aryl chlorides, aryl bromides, aryl iodides, and combinations thereof.

In another preferred embodiment, the $R_1$ is selected from the group consisting of a substituted or unsubstituted saturated or unsaturated 3-15 membered (preferably 5-9 membered) heterocyclic group having 1 to 3 hetero atoms, the hetero atom is selected from N, O or S, and the heterocyclic group is saturated or unsaturated.

In another preferred embodiment, the $R_1$ is selected from the group consisting of a substituted or unsubstituted indolyl group, substituted or unsubstituted pyrrolyl group, substituted or unsubstituted benzimidazolyl group, substituted or unsubstituted imidazolyl group, substituted or unsubstituted thiazolyl, substituted or unsubstituted benzothiazolyl, substituted or unsubstituted saturated or unsaturated 6-membered heterocyclic group containing 1 or 2 N atoms (e.g., pyridyl, pyrazinyl, pyrimidinyl), substituted or unsubstituted phenyl, substituted or unsubstituted naphthyl, substituted or unsubstituted benzyl, substituted or unsubstituted quinolinyl, substituted or unsubstituted

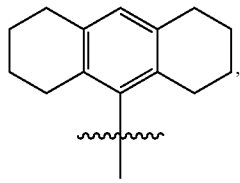 [SMILES: *c1c2c(cc3c1CCCC3)CCCC2]

substituted or unsubstituted adamantyl, substituted or unsubstituted C1-C6 alkyl, substituted or unsubstituted

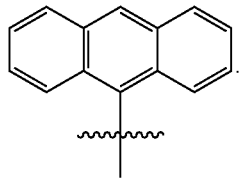 [SMILES: *c1c2ccccc2cc2ccccc12]

In another preferred embodiment, "substituted" means that one or more hydrogen atoms on a group are substituted with a substituent selected from the group consisting of halogen, methyl, trifluoromethyl, ethyl, isopropyl, tert-butyl, dimethylamino, methoxy, tert-butoxy, —Ac, CH$_3$NHC(O)—, phenyl, phenoxy, —COOH, ester group, nitro, cyano, hydroxy, methylthio.

In another preferred embodiment, the aryl halide is aryl chloride.

In another preferred embodiment, the structure of the compound is as shown in Formula II:

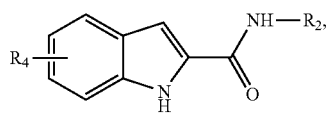

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R_4$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure.

In another preferred embodiment, the number of $R_4$ substituent is 1-4, the substitution position may be ortho or meta, and each $R_4$ may be the same or different. When the number of $R_5$ substituent is ≤2, the adjacent $R_4$ may be linked to form a ring (preferably a 3-20 membered ring, which may be a saturated, unsaturated or aromatic carbocyclic or heterocyclic ring).

In another preferred embodiment, the structure of the compound is as shown in Formula III:

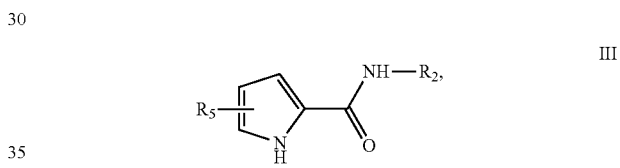

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

$R_5$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of $R_5$ substituent is 1-3, the substitution position may be ortho or meta, and each $R_5$ may be the same or different. When the number of $R_5$ substituent is ≤2, the adjacent $R_5$ may be linked to form a ring (preferably a 3-20 membered ring, which may be a saturated, unsaturated or aromatic carbocyclic or heterocyclic ring).

In another preferred embodiment, the structure of the compound is as shown in Formula IV:

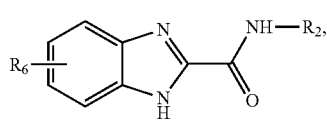

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

$R_6$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of $R_6$ substituent is 1-4, the substitution position may be ortho or meta, and each $R_6$ may be the same or different. When the number of $R_6$ substituent is ≤2, the adjacent $R_6$ may be linked to form a ring (preferably a 3-20 membered ring, which may be a saturated, unsaturated or aromatic carbocyclic or heterocyclic ring).

In another preferred embodiment, the structure of the compound is as shown in the formula Va, Vb, or Vc:

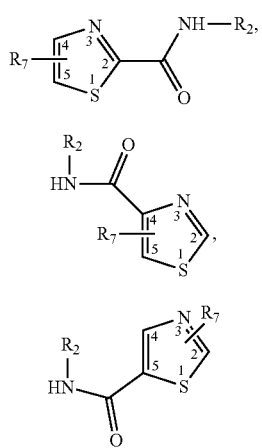

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R_7$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of $R_7$ substituent is 1 or 2, and each $R_7$ may be the same or different. When the number of $R_7$ substituent is 2, the adjacent $R_7$ may be linked to form a ring (preferably 6-20 membered aromatic rings, such as benzene rings).

In another preferred embodiment, the structure of the compound is as shown in the formula VIa, VIb, or VIc:

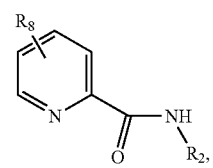

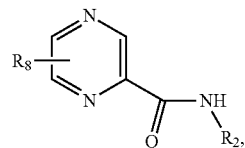

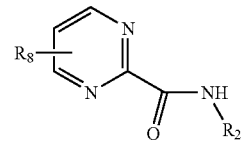

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

R₈ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of R₈ substituent is 1-3, and each R₈ may be the same or different. When the number of R₈ substituent is ≤2, the adjacent R₈ may be linked to form a ring (preferably 6-20 membered saturated or unsaturated aromatic rings).

In another preferred embodiment, the structure of the compound is as shown in Formula VII:

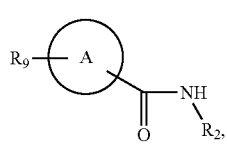

VII

Wherein R₂ is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

R₉ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

A is 3- to 12-membered saturated or unsaturated heterocyclic group wherein the heterocyclic group contains 1 to 4 heteroatoms each independently selected from N, O, and S.

In another preferred embodiment, A is a 5-membered heterocyclic ring containing one N atom.

In another preferred embodiment, A is furan, thiophene or pyrrole.

In another preferred embodiment, the number of R₉ substituent is 1-3, and each R₉ may be the same or different. When the number of R₉ substituent is ≤2, the adjacent R₉ may be linked to form a ring (preferably 6-20 membered saturated or unsaturated aromatic rings, such as benzene ring).

In another preferred embodiment, the compound is selected from the following group:

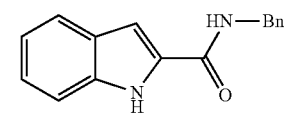

L-1

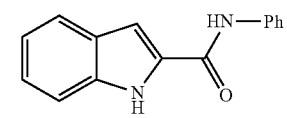

L-2

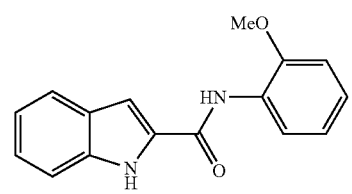 [SMILES: COc1ccccc1NC(=O)c1cc2ccccc2[nH]1]

L-3

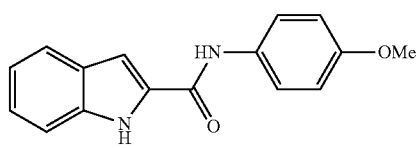 [SMILES: COc1ccc(NC(=O)c2cc3ccccc3[nH]2)cc1]

L-4

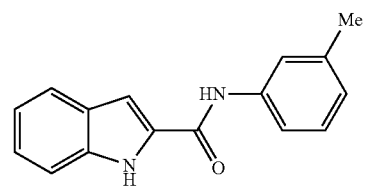 [SMILES: Cc1cccc(NC(=O)c2cc3ccccc3[nH]2)c1]

L-5

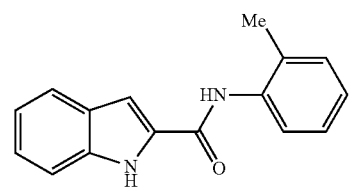

L-6

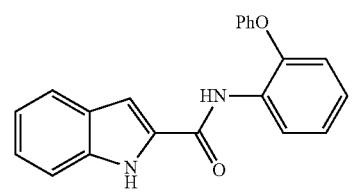

L-7

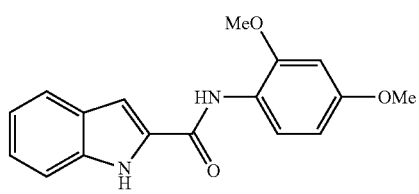 [SMILES: COc1ccc(NC(=O)c2cc3ccccc3[nH]2)c(OC)c1]

L-8

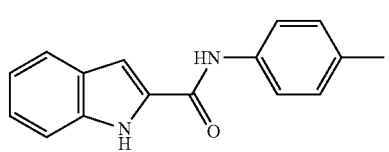

L-9

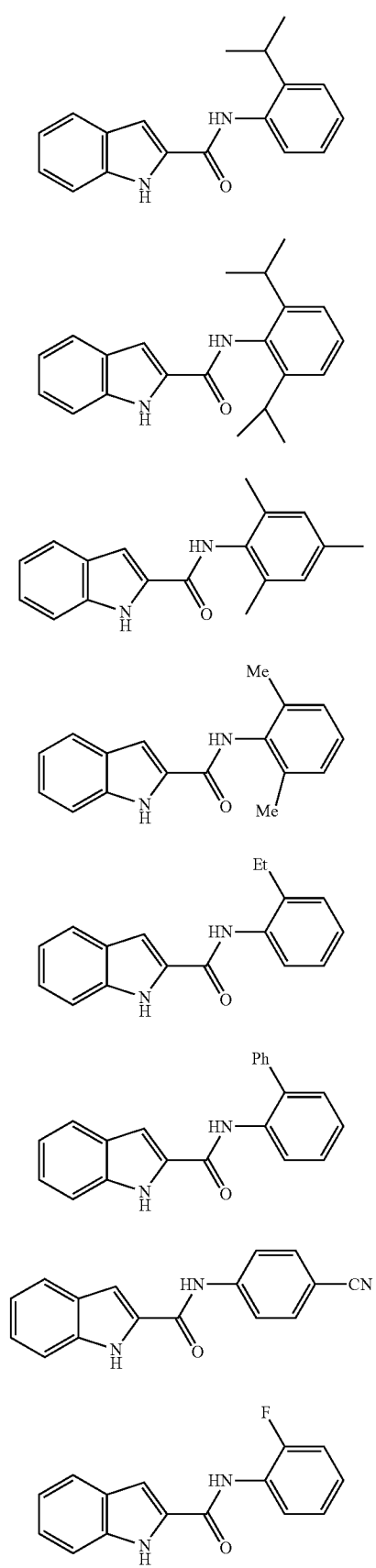
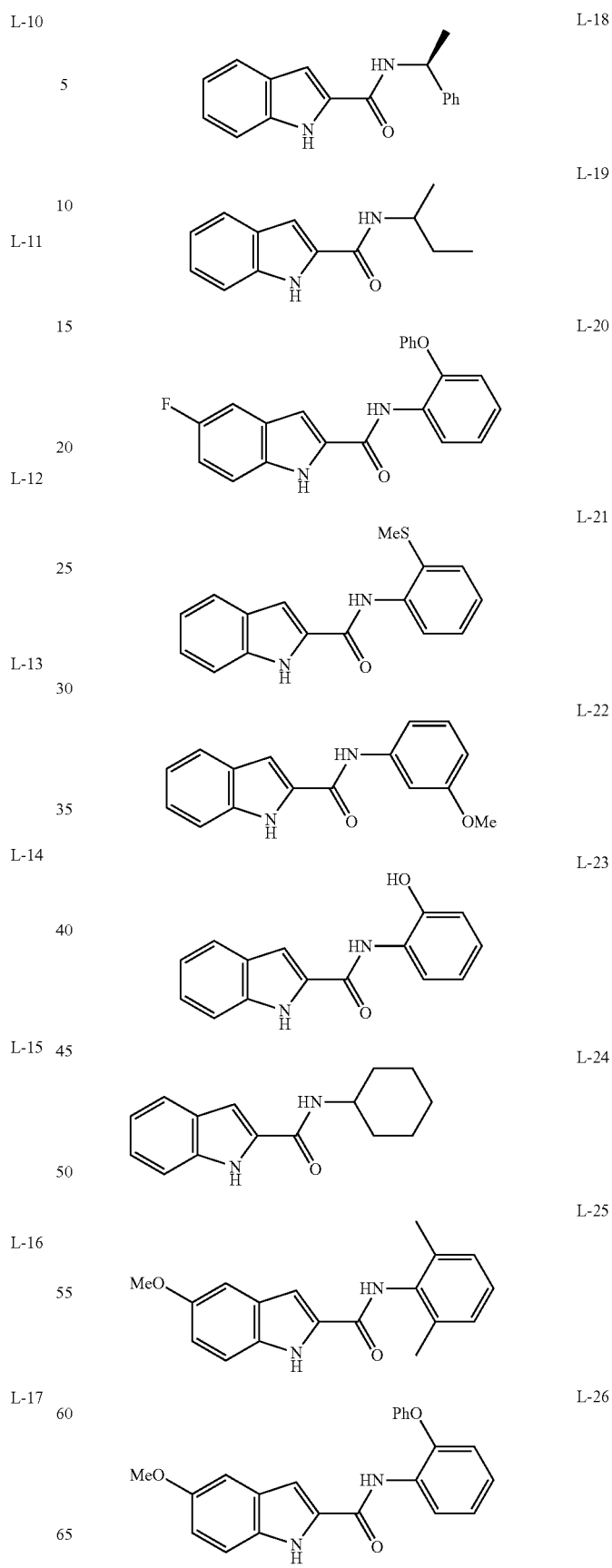

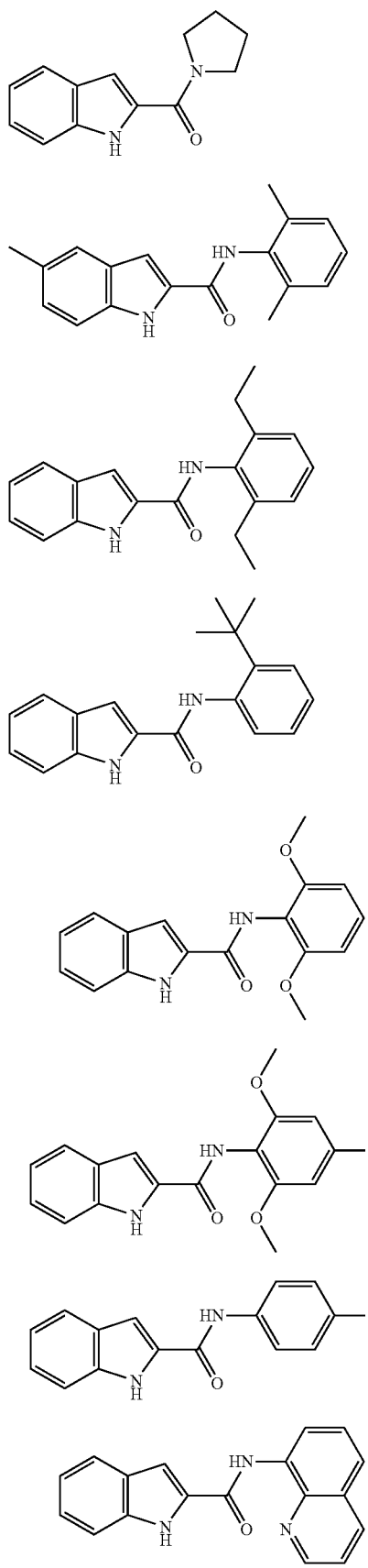
L-27
L-28
L-29
L-30
L-31
L-32
L-33
L-34
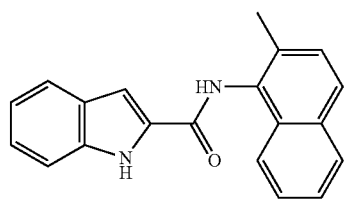 [SMILES: Cc1ccc2ccccc2c1NC(=O)c1cc2ccccc2[nH]1]
L-35
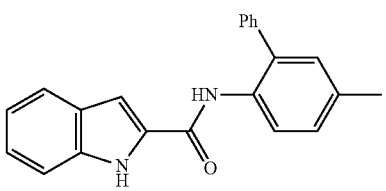 [SMILES: Cc1ccc(NC(=O)c2cc3ccccc3[nH]2)c(-c2ccccc2)c1]
L-36
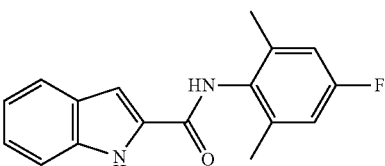
L-37
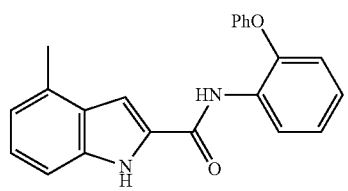
L-38
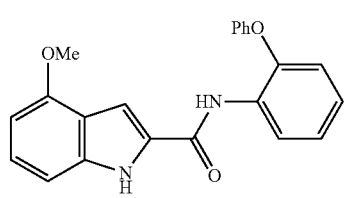 [SMILES: COc1cccc2[nH]c(C(=O)Nc3ccccc3Oc3ccccc3)cc12]
L-39
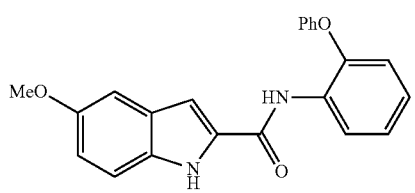 [SMILES: COc1ccc2[nH]c(C(=O)Nc3ccccc3Oc3ccccc3)cc2c1]
L-40
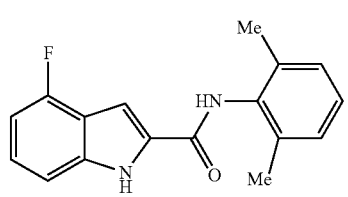 [SMILES: Cc1cccc(C)c1NC(=O)c1cc2c(F)cccc2[nH]1]
L-41
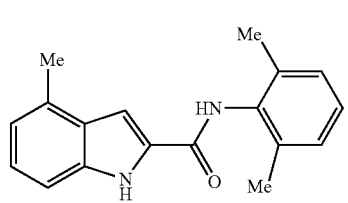 [SMILES: Cc1cccc(C)c1NC(=O)c1cc2c(C)cccc2[nH]1]
L-42

-continued
L-43
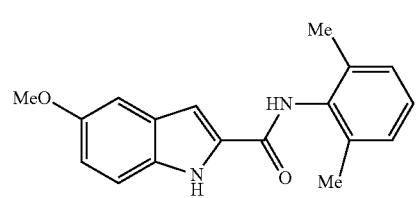 [SMILES: COc1ccc2[nH]c(C(=O)Nc3c(C)cccc3C)cc2c1]
L-44
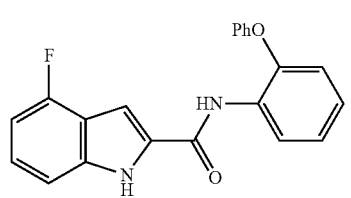
L-45
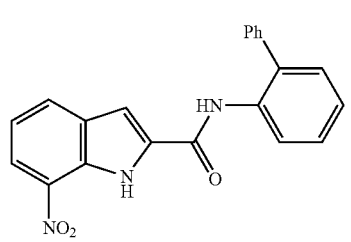 [SMILES: O=C(Nc1ccccc1-c1ccccc1)c1cc2cccc([N+](=O)[O-])c2[nH]1]
L-46
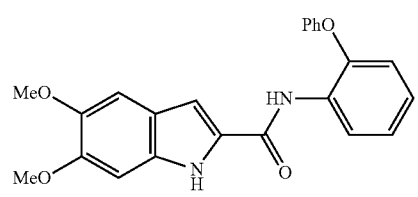 [SMILES: COc1cc2cc(C(=O)Nc3ccccc3Oc3ccccc3)[nH]c2cc1OC]
L-47
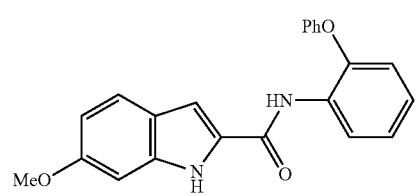 [SMILES: COc1ccc2cc(C(=O)Nc3ccccc3Oc3ccccc3)[nH]c2c1]
L-48
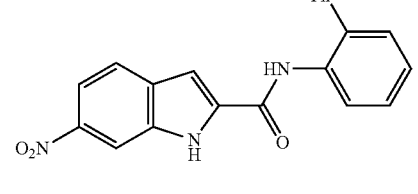
L-49
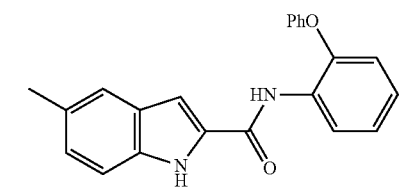 [SMILES: Cc1ccc2[nH]c(C(=O)Nc3ccccc3Oc3ccccc3)cc2c1]
L-50
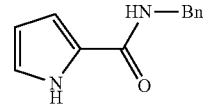 [SMILES: O=C(NCc1ccccc1)c1ccc[nH]1]
-continued
L-51
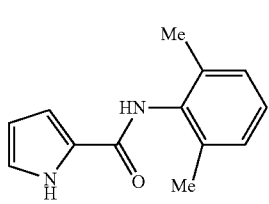 [SMILES: Cc1cccc(C)c1NC(=O)c1ccc[nH]1]
L-52
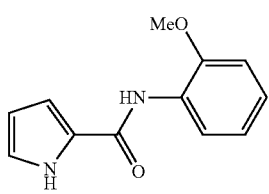
L-53
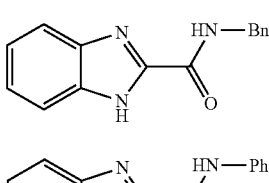
L-54
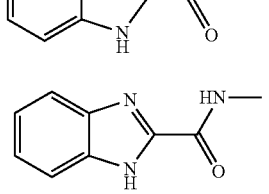
L-55
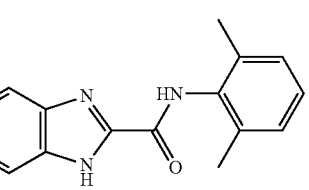
L-56
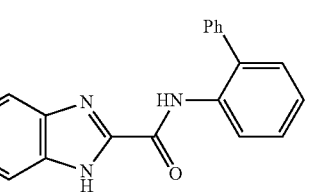
L-57
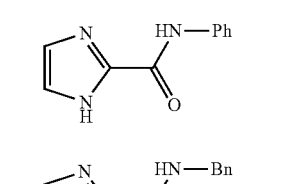
L-58
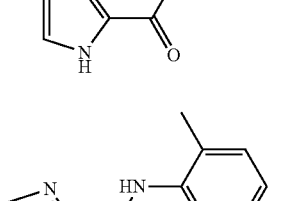
L-59
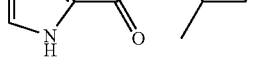
L-60

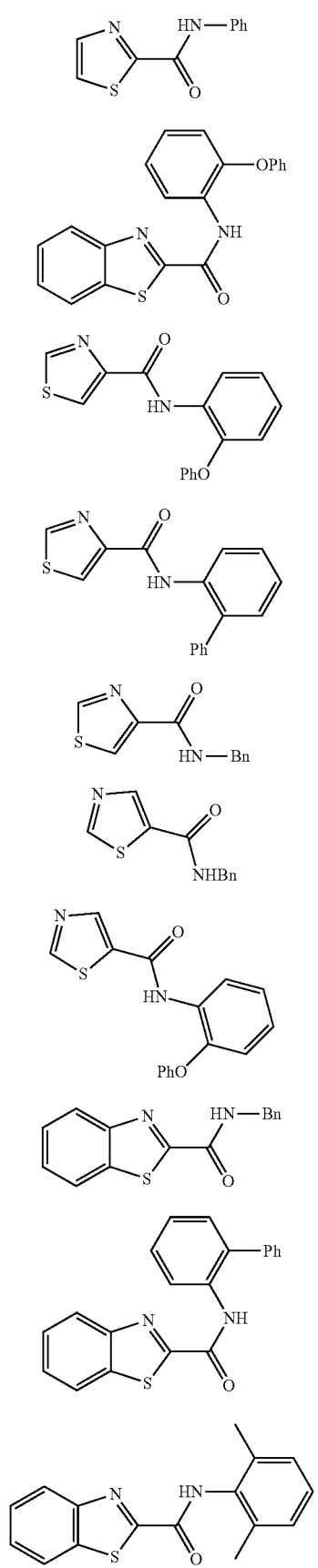
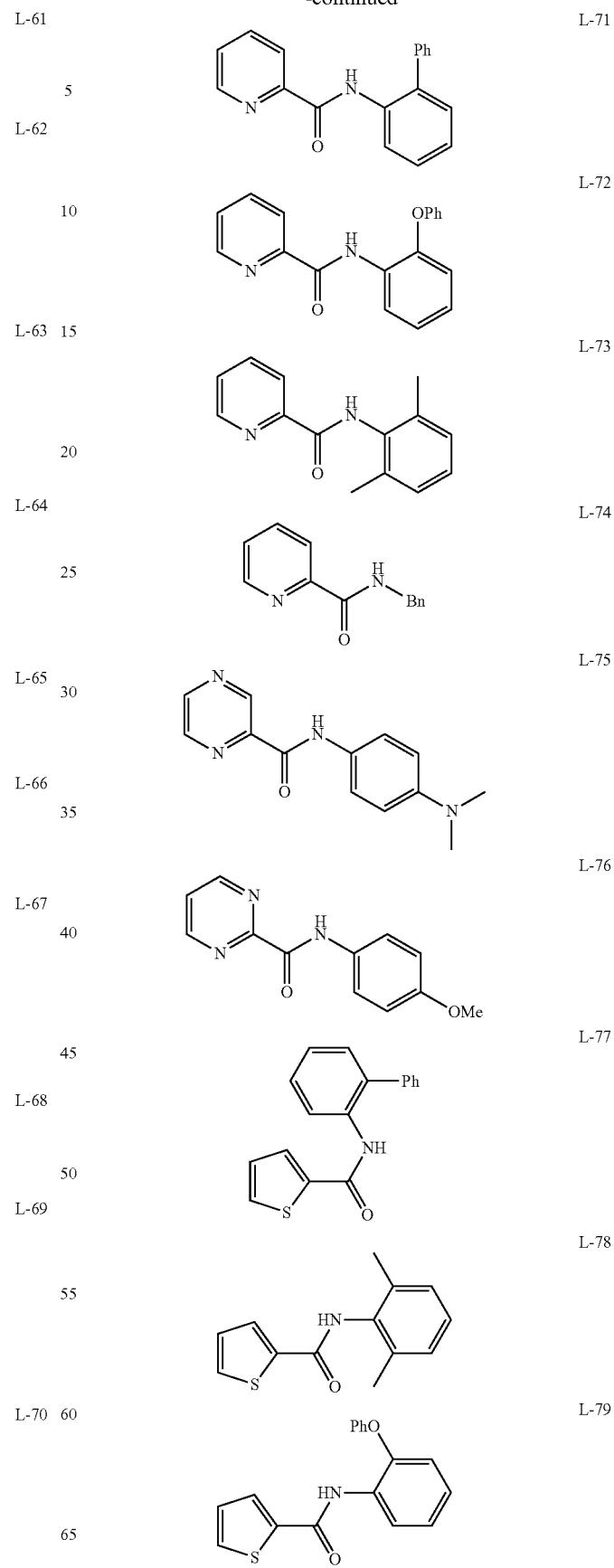

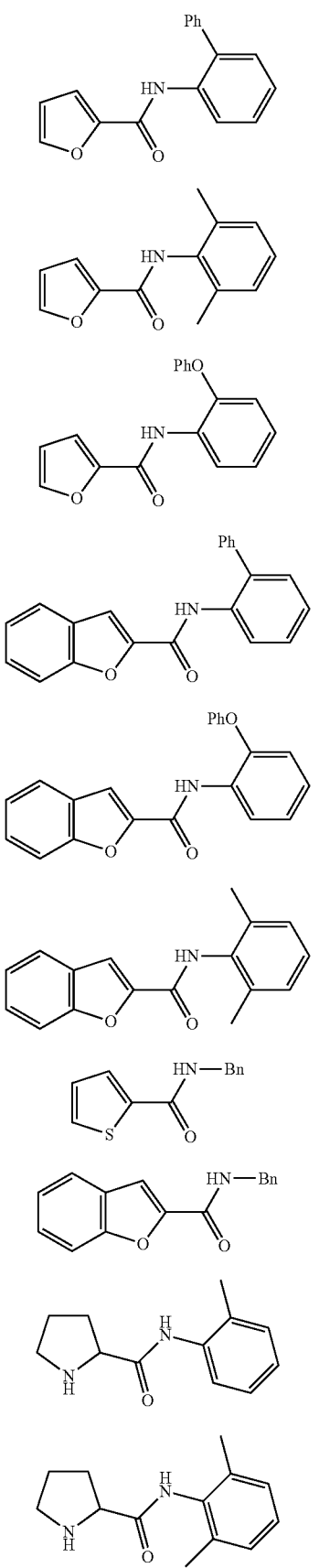
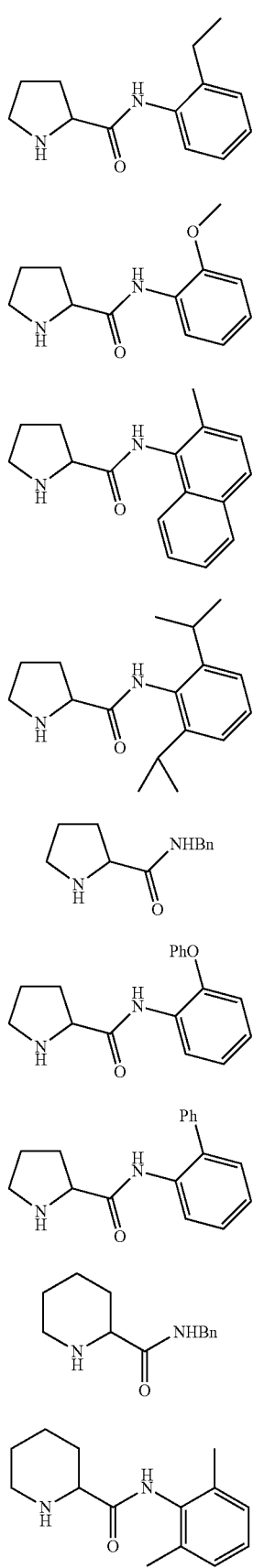

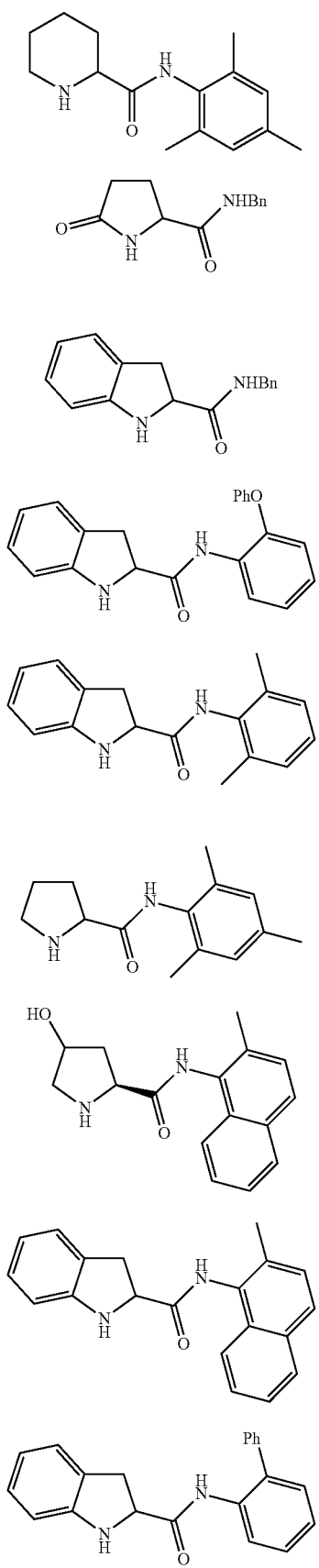
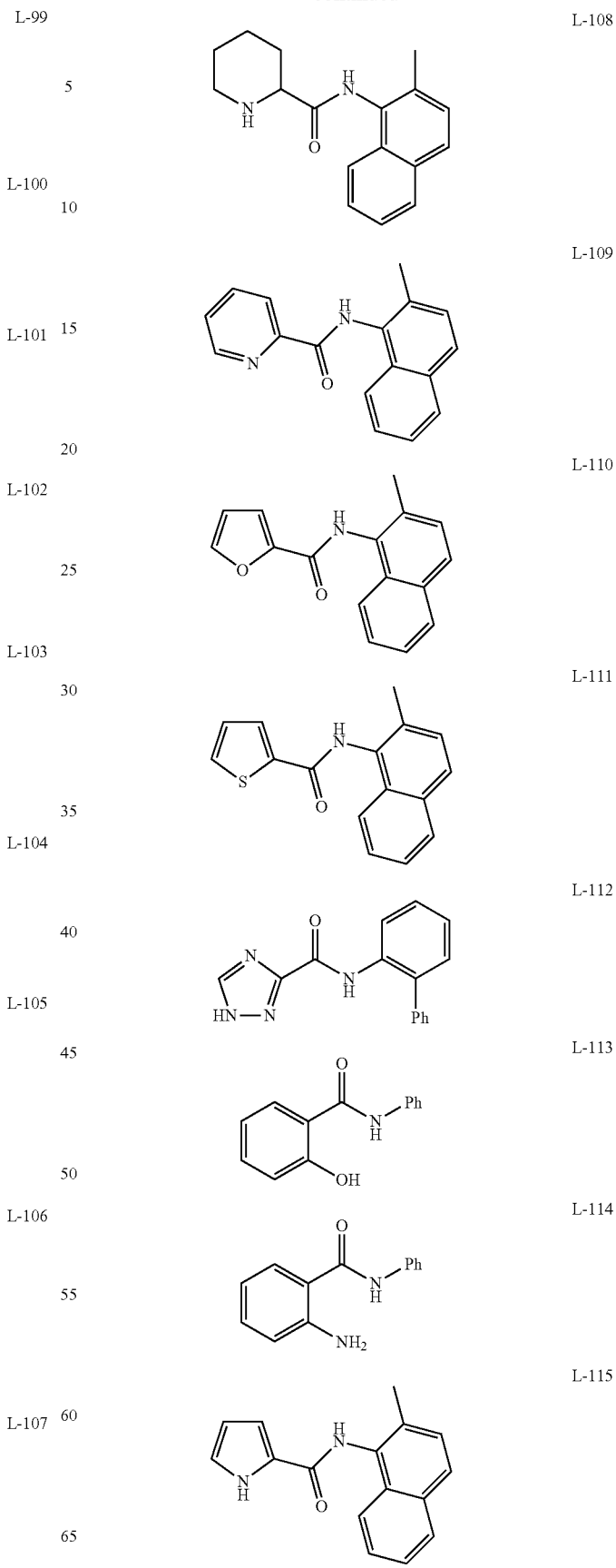

L-116

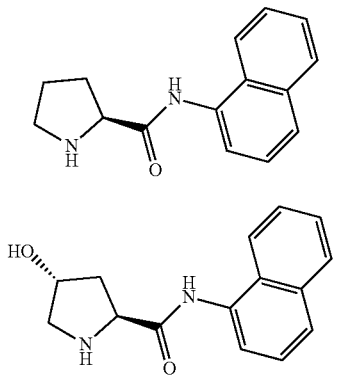

L-117

In the second aspect of the present invention, a method for coupling reaction of aryl halide is provided, comprising: carrying out the coupling reaction using copper as a catalyst and the compound of following formula I as a ligand:

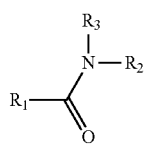

I

Wherein R; is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R^2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be of monocyclic, multiple-cyclic, Spiro or bridged ring structure;

$R_3$ is selected from the group consisting of hydrogen, and a substituted or unsubstituted C1-C6 alkyl;

or $R_2$ and $R_3$ together with the connected N atom to form a 3- to 20-membered saturated or unsaturated ring (e.g., substituted or unsubstituted pyrrole, indole, azole, benzoxazole, and aromatic heterocycle);

wherein the aryl halide is selected from the group consisting of aryl chlorides, aryl bromides, aryl iodides, and combinations thereof.

In another preferred embodiment, the copper catalyst is selected from the group consisting of CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, and combinations thereof; preferably CuI.

In another preferred embodiment, the reaction is carried out in the presence of a base.

In another preferred embodiment, the base is selected from the group consisting of potassium carbonate, cesium carbonate, potassium phosphate, sodium bicarbonate, potassium bicarbonate, sodium carbonate, sodium hydroxide, potassium hydroxide, lithium hydroxide, sodium acetate, and combinations thereof; preferably potassium phosphate or cesium carbonate; most preferably potassium phosphate.

In another preferred embodiment, in the reaction, the molar ratio of the ligand to the reactant aryl halide is 1-50:100, preferably 5-20:100; the molar ratio of the ligand to the copper catalyst is 1-5:1, preferably 1-2:1.

In another preferred embodiment, the reaction comprises:

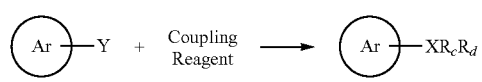

In an inert solvent, reacting

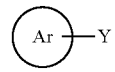

with a coupling reagent to obtain compound

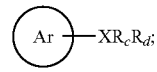

Wherein X is selected from the group consisting of N, O and S;

Y is selected from the group consisting of Cl, Br, and I;

is selected from the group consisting of a substituted or unsubstituted C6-C20 aryl, substituted or unsubstituted 3- to 20-membered heteroaryl; wherein the "substituted" means that one or more hydrogen atoms on the aryl group is substituted by a substituent selected from the group consisting of halogen, nitro, cyano, amino which is unsubstituted or substituted with 1 or 2 C1-C6 alkyls or C2-C10 acyls (alkyl-CO—), hydroxy, unsubstituted or halogenated C1-C6 alkyl, C1-C6 alkoxy, C6-C10 aryl, 3- to 20-membered heteroaryl, C6-C10 aryl-oxy, C2-C10 ester group (alkyl-COO—), C2-C10 acyl (alkyl-CO—), C2-C10 acyl-alkoxy (alkyl-OOC—), C2-C10 amide group (alkyl-NHC(O)—, aryl-NHC(O)—), —COOH, hydroxy-C1-C10 alkylene, MeS—, sulfonyl, sulfamine group; wherein two hydrogen atoms on adjacent carbon atoms of the aryl may be substituted by —(CH$_2$)$_n$— (n is 1, 2, 3, 4, 5 or 6);

The coupling reagent is selected from the group consisting of ammonia water, ammonia gas, ammonium salt (preferably ammonium chloride, ammonium carbonate, ammonium sulfate, ammonium hydrogen phosphate, or a combination thereof)/hydroxide solution (preferably potassium hydroxide solution),

$R_eC(O)NHR_d$, $R_cSO_2M$ (preferably, M is sodium or potassium), sodium azide, $NHR_cR_d$, $R_cOH$, $R_cSH$, hydroxide, and a salt that can be hydrolyzed to form hydroxide;

$R_c$, $R_d$, $R_e$ are each independently select from the group consisting of H, a substituted or unsubstituted C1-C6 alkyl, substituted or unsubstituted C1-C6 alkenyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, substituted or unsubstituted C1-C5 alkyl-(C3-C20 cycloalkyl), substituted or unsubstituted 3- to 20-membered heterocyclic group, and substituted or unsubstituted C1-C5 alkyl-(3- to 20-membered heterocyclic group);

or $R_c$ and $R_d$ together form a substituted or unsubstituted C3-C20 cycloalkyl, substituted or unsubstituted 3- to 20-membered heterocyclic group;

or $R_e$ and $R_d$ together form a substituted or unsubstituted C3-C20 cycloalkyl, substituted or unsubstituted 3- to 20-membered heterocyclic group;

Wherein the heteroaryl or heterocyclic group has 1 to 5 heteroatoms selected from the group consisting of N, O and S; the cycloalkyl or heterocyclic group may be of monocyclic, multiple cyclic, spiral or bridged ring structure;

The "substituted" means that one or more hydrogen atoms on a group are substituted by substituent selected from the group consisting of halogen, cyano, oxygen (i.e., two hydrogen atoms on the same carbon atom on the group are replaced by =O), a C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 amide group (alkyl/aryl NHC(O)—), —COOH, nitro, hydroxy, amino, amino substituted by 1 or 2 C1-C6 alkyl groups, C1-C6 alkyl-S—.

In another preferred embodiment, the inert solvent is selected from the group consisting of: DMSO, DMF, DMA, NMP, acetonitrile, tert-butanol, isopropanol, and combinations thereof; preferably DMSO and/or DMF.

In another preferred embodiment, the reaction temperature is 50-180° C., preferably 100-130° C.

In another preferred embodiment, the reaction comprises the following (1), (2), (3) or (4):

(1) reacting

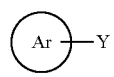

with $NHR_cR_d$ in an inert solvent to give

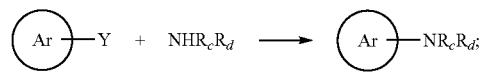

Wherein the groups are defined as above;

(2) reacting

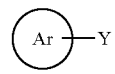

with ammonia source in an inert solvent to obtain

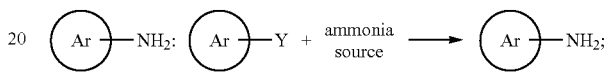

Wherein the groups are defined as above;

The ammonia source is selected from the group consisting of ammonia gas, ammonium hydroxide, ammonium chloride, ammonium carbonate, ammonium hydrogen carbonate, ammonium sulfate, ammonium nitrate, ammonium phosphate, diammonium hydrogen phosphate, sodium azide; preferably ammonia gas, ammonium hydroxide, ammonium chloride and diammonium hydrogen phosphate.

(3) in an inert solvent, reacting

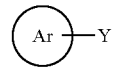

with $R_cOH$ to provide

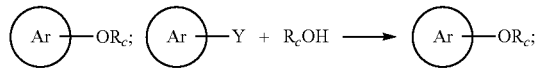

Wherein the groups are defined as above;

(4) in an inert solvent, reacting

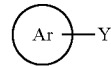

with $R_cSO_2M$ to provide

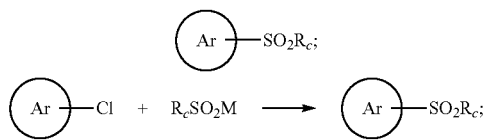

Wherein the groups are defined as above.

(5) in an inert solvent, reacting

with R$_c$SH to provide

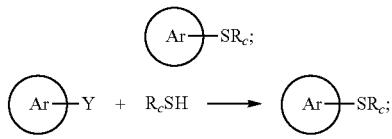

Wherein the groups are defined as above.

In another preferred embodiment, in the reaction (1), the ligand is preferably L-53 or L-103.

In another preferred embodiment, in the reaction (1), the base is selected from the group consisting of potassium carbonate, cesium carbonate, potassium phosphate, sodium carbonate, sodium hydrogen carbonate, potassium hydrogen carbonate, and combinations thereof; preferably potassium phosphate.

In another preferred embodiment, in the reaction (1), the inert solvent can be DMSO, DMF, DMA, NMP, acetonitrile, tert-butanol, isopropanol, THF, 1,4-dioxane, preferably DMSO, DMF, most preferably DMSO.

In another preferred embodiment, in the reaction (1), the reaction temperature is 50-180° C., preferably 100-130° C.

In another preferred embodiment, in the reaction (2), the ligand is preferably selected from: L-13, L-15 or L-31.

In another preferred embodiment, in the reaction (2), the base is selected from the group consisting of potassium carbonate, cesium carbonate, potassium phosphate, sodium carbonate, sodium hydrogen carbonate, potassium hydrogen carbonate, and combinations thereof; preferably potassium phosphate.

In another preferred embodiment, in the reaction (2), when the ammonia source is an ammonium salt, the reaction is carried out in the presence of a strong base (preferably in the presence of KOH).

In another preferred embodiment, in the reaction (2), the solvent is selected from the group consisting of DMSO, DMF, DMA, NMP, acetonitrile, tert-butanol, isopropanol, THF, 1,4-dioxane, preferably DMSO, DMF, most preferably DMSO.

In another preferred embodiment, in the reaction (2), the reaction temperature is 50-180° C., preferably 100-130° C.

In another preferred embodiment, in the reaction (3), the ligand is preferably selected from: L-13, L-15 or L-35.

In another preferred embodiment, in the reaction (3), the base is selected from the group consisting of potassium carbonate, cesium carbonate, potassium phosphate, sodium carbonate, sodium hydrogen carbonate, potassium hydrogen carbonate, and combinations thereof; preferably potassium phosphate.

In another preferred embodiment, in the reaction (3), the solvent is selected from the group consisting of DMSO, DMF, DMA, NMP, acetonitrile, tert-butanol, isopropanol, THF, 1,4-dioxane, preferably DMSO.

In another preferred embodiment, in the reaction (3), the reaction temperature is 50-180° C., preferably 100-130° C.

In another preferred embodiment, in the reaction (4), the ligand is preferably selected from: L-92, and/or L-105.

In another preferred embodiment, in the reaction (4), the base is selected from the group consisting of potassium carbonate, cesium carbonate, potassium phosphate, sodium carbonate, sodium hydrogen carbonate, potassium hydrogen carbonate, and combinations thereof; preferably potassium phosphate.

In another preferred embodiment, in the reaction (4), the solvent is selected from the group consisting of: DMSO, DMF, DMA, NMP, acetonitrile, tert-butanol, isopropanol, THF, 1,4-dioxane, and combinations thereof; preferably DMSO.

In another preferred embodiment, in the reaction (4), the reaction temperature is 50-180° C., preferably 100-130° C.

In another preferred embodiment, in the reaction (5), the ligand is preferably selected from: L-13, L-112, L-114.

In another preferred embodiment, in the reaction (5), the base is selected from the group consisting of potassium carbonate, cesium carbonate, potassium phosphate, sodium carbonate, sodium hydrogen carbonate, potassium hydrogen carbonate, and combinations thereof; preferably potassium phosphate.

In another preferred embodiment, in the reaction (5), the solvent is selected from the group consisting of DMSO, DMF, DMA, NMP, acetonitrile, tert-butanol, isopropanol, THF, 1,4-dioxane, DME, and combinations thereof; preferably DME.

In another preferred embodiment, in the reaction (5), the reaction temperature is 25-180° C., preferably 50-120° C.

In a third aspect of the invention, a catalytic system for an aryl coupling reaction is provided, the reaction system comprising: a copper catalyst, ligand, base, and organic solvent;

wherein the copper catalyst is selected from the group consisting of CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, and combinations thereof; preferably CuI;

the base is selected from the group consisting of potassium carbonate, cesium carbonate, potassium phosphate, sodium bicarbonate, potassium bicarbonate, sodium carbonate, sodium hydroxide, potassium hydroxide, lithium hydroxide, sodium acetate, and combinations thereof; preferably potassium phosphate or cesium carbonate;

The solvent is selected from the group consisting of DMSO, DMF, DMA, NMP, acetonitrile, tert-butanol, isopropanol, 1,4-dioxane, tetrahydrofuran, DME, toluene, and combinations thereof; preferably DMSO and/or DMF and/or DME;

The ligand is of the structure shown in formula (I):

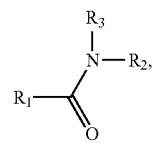

Wherein the groups are defined as in the first aspect of the present invention.

In another preferred embodiment, the catalytic system is used to carry out the coupling reaction of aryl halide; the aryl halide is selected from the group consisting of aryl chloride, aryl bromide, and aryl iodide.

In another preferred embodiment, the catalytic system is used to carry out the coupling reaction of aryl chloride.

In the fourth aspect of the present invention, a compound of the formula (I) is provided:

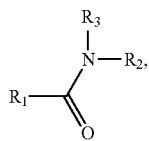

Wherein $R_1$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R^2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be of monocyclic, multiple-cyclic, spiro or bridged ring structure;

$R_3$ is selected from the group consisting of hydrogen, and a substituted or unsubstituted C1-C6 alkyl;

or $R_2$ and $R_3$ together with the connected N atom to form a 3- to 20-membered saturated or unsaturated ring (e.g., a substituted or unsubstituted pyrrole, indole, azole, benzoxazole, and aromatic heterocycle).

In another preferred embodiment, in the compound, any one of $R_1$, $R_2$, and $R_3$ is the group corresponding to the group in the specific compounds in the present application.

In another preferred embodiment, the structure of the compound is as shown in Formula II:

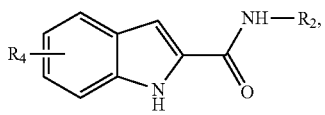

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

$R_4$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure.

In another preferred embodiment, the number of $R_4$ substituent is 1-4, the substitution position may be ortho or meta, and each $R_4$ may be the same or different. When the number of $R_4$ substituent is ≤2, the adjacent $R_4$ may be linked to form a ring.

In another preferred embodiment, the structure of the compound is as shown in Formula III:

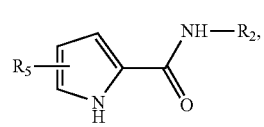

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R_5$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of $R_5$ substituent is 1-3, the substitution position may be ortho or meta, and each $R_5$ may be the same or different. When the number of $R_5$ substituent is ≤2, the adjacent $R_5$ may be linked to form a ring.

In another preferred embodiment, the structure of the compound is as shown in formula VI:

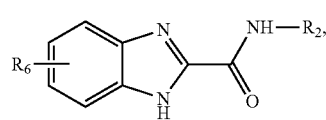

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R_6$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of $R_6$ substituent is 1-4, the substitution position may be ortho or meta, and each $R_6$ may be the same or different. When the number of $R_6$ substituent is ≤2, the adjacent $R_6$ may be linked to form a ring.

In another preferred embodiment, the structure of the compound is as shown in the formula Va, Vb, or Vc:

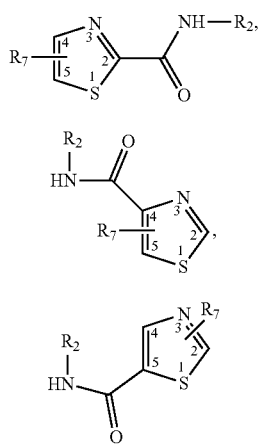

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R_7$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of $R_7$ substituent is 1 or 2, and each $R_7$ may be the same or different. When the number of $R_7$ substituent is 2, the adjacent $R_7$ may be linked to form a ring (preferably 6-20 membered aromatic rings, such as benzene rings).

In another preferred embodiment, the structure of the compound is as shown in the formula VIa, VIb, or VIc:

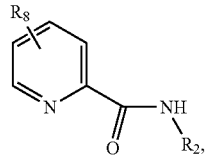

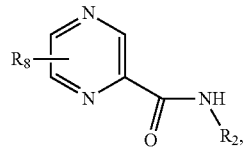

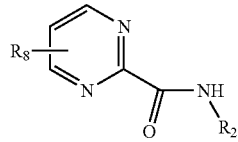

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

$R_8$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of $R_8$ substituent is 1-3, and each $R_8$ may be the same or different. When the number of $R_8$ substituent is ≤2, the adjacent $R_8$ may be linked to form a ring (preferably 6-20 membered saturated or unsaturated aromatic rings).

In another preferred embodiment, the structure of the compound is as shown in Formula VII:

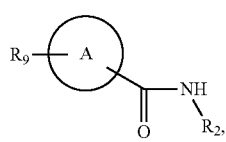

VII

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R_9$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

A is 3- to 12-membered saturated or unsaturated heterocyclic group wherein the heterocyclic group contains 1 to 4 heteroatoms each independently selected from N, O, and S.

In another preferred embodiment, A is a 5-membered heterocyclic ring containing one N atom.

In another preferred embodiment, A is furan, thiophene or pyrrole.

In another preferred embodiment, the number of $R_9$ substituent is 1-3, and each $R_9$ may be the same or different. When the number of $R_9$ substituent is ≤2, the adjacent $R_9$ may be linked to form a ring (preferably 6-20 membered saturated or unsaturated aromatic rings, such as benzene ring).

In another preferred embodiment, the compound of formula (I) is selected from the group consisting of

| Type 1 |
|---|
| 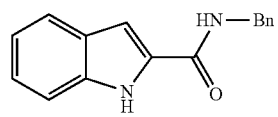 L-1 |
| 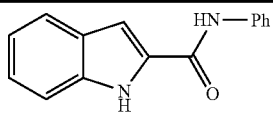 L-2 |
| 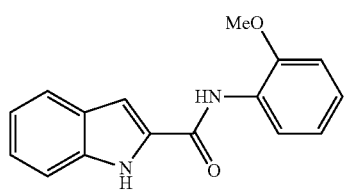 L-3 |
| 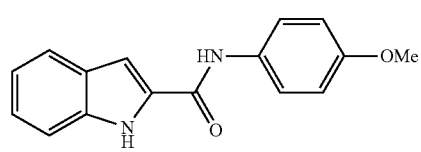 L-4 |
| 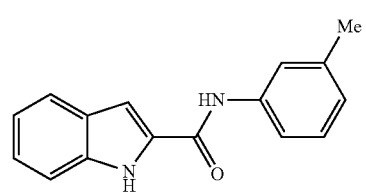 L-5 |
| 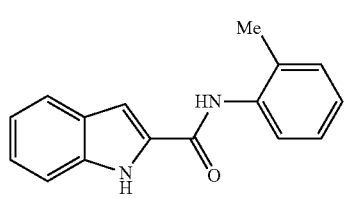 L-6 |
| 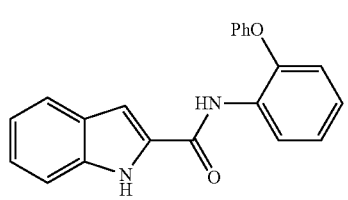 L-7 |
| 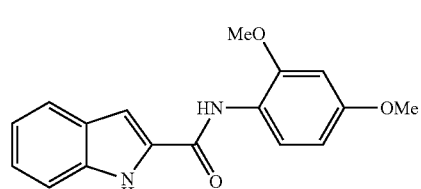 L-8 |
| 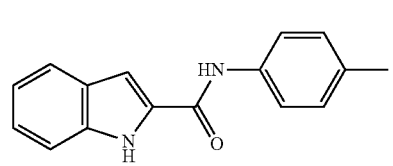 L-9 |
| 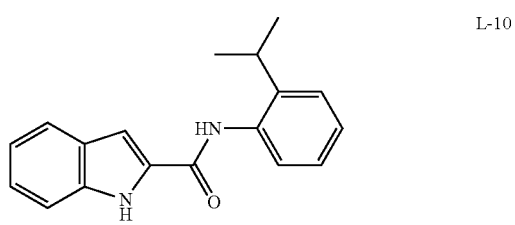 L-10 |

-continued
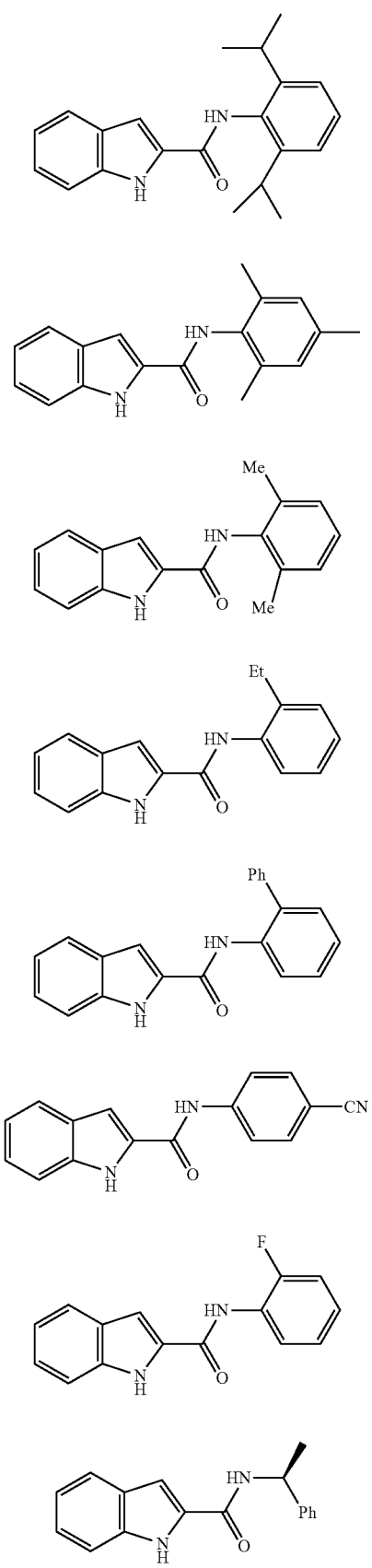
L-11
L-12
L-13
L-14
L-15
L-16
L-17
L-18
-continued
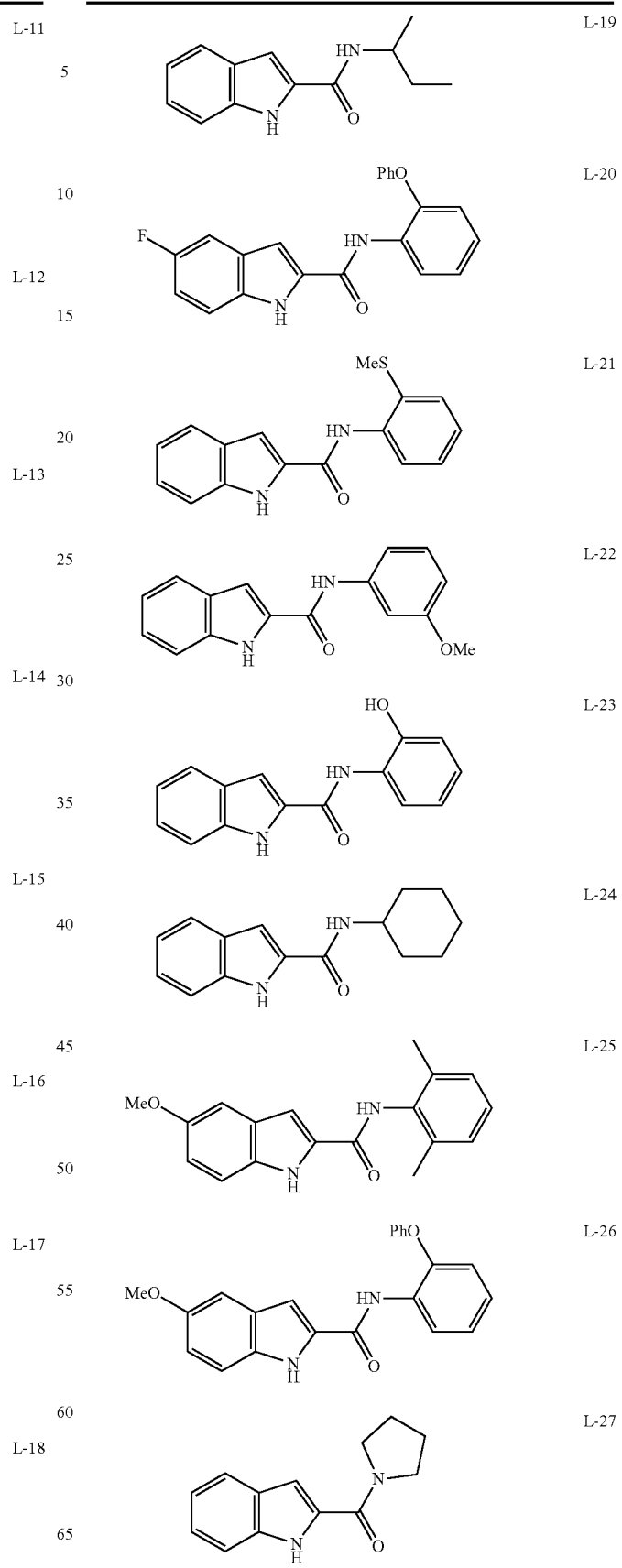
L-19
L-20
L-21
L-22
L-23
L-24
L-25
L-26
L-27

| | |
|---|---|
| 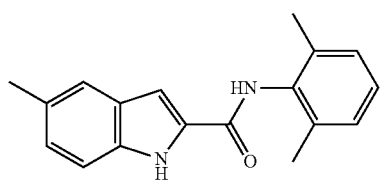 L-28 | 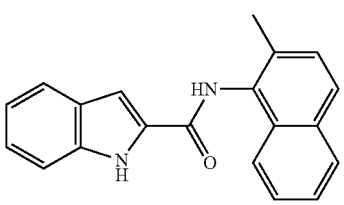 L-35 |
| 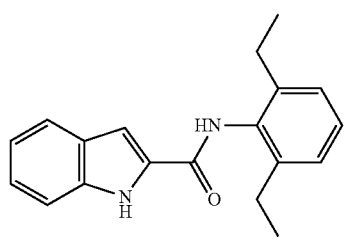 L-29 | 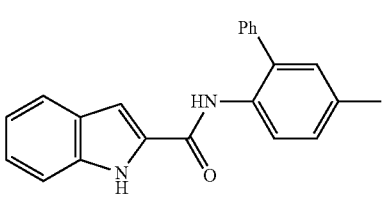 L-36 |
| 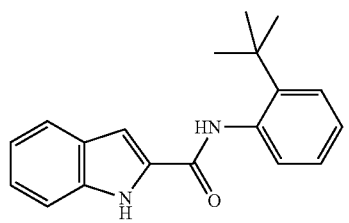 L-30 | 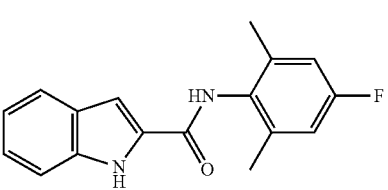 L-37 |
| 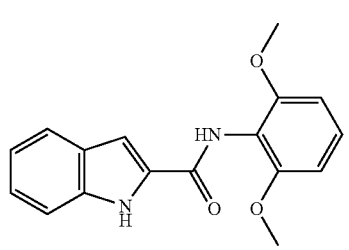 L-31 | 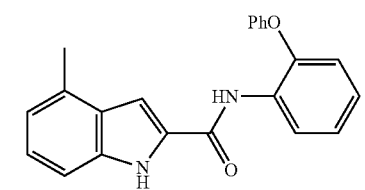 L-38 |
| 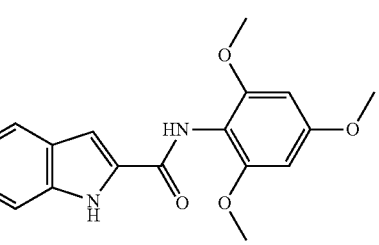 L-32 | 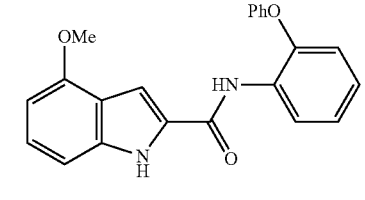 L-39 |
| 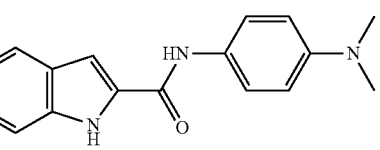 L-33 | 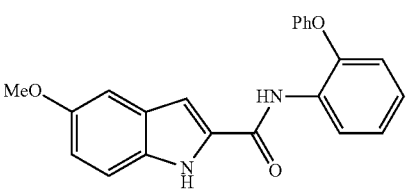 L-40 |
| 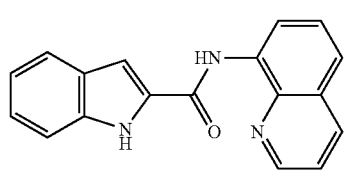 L-34 | 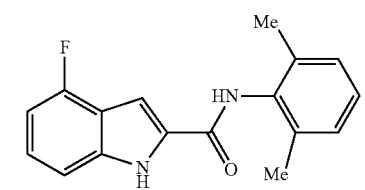 L-41 |
| | 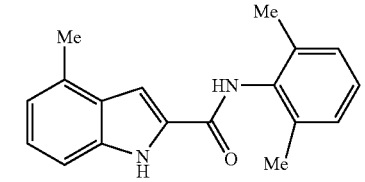 L-42 |

-continued
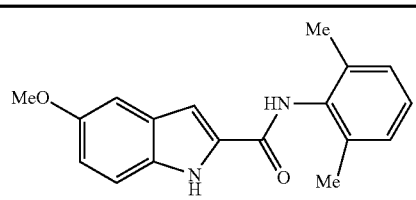 L-43
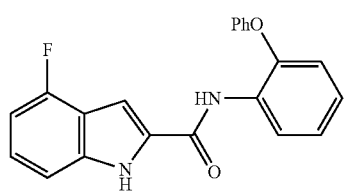 L-44
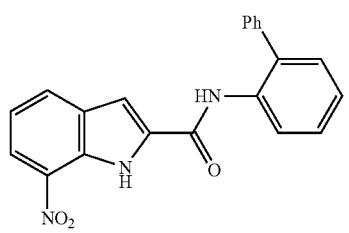 L-45
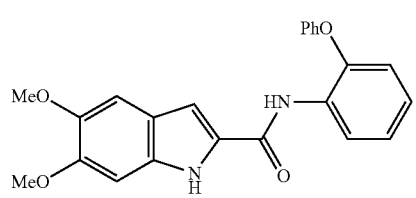 L-46
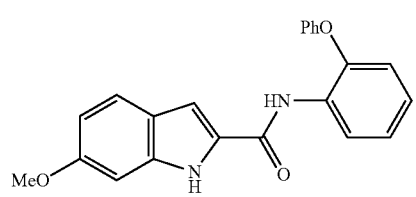 L-47
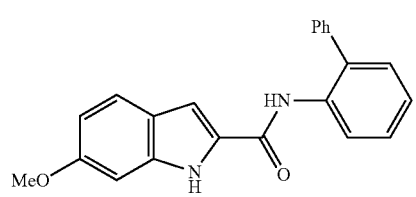 L-48
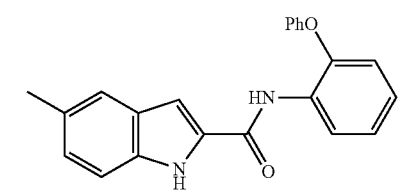 L-49
Type 2:
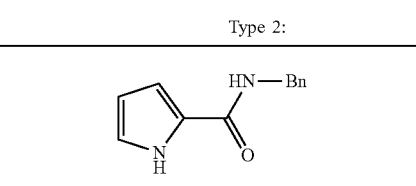 L-50
-continued
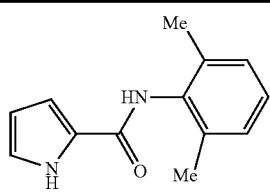 L-51
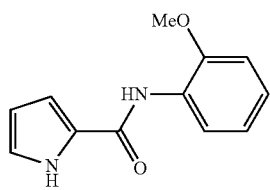 [SMILES: COc1ccccc1NC(=O)c1ccc[nH]1] L-52
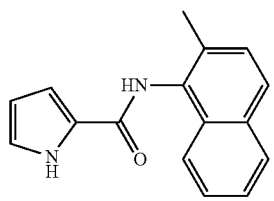 [SMILES: Cc1ccc2ccccc2c1NC(=O)c1ccc[nH]1] L-115
Type 3
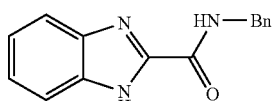 L-53
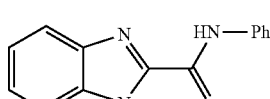 L-54
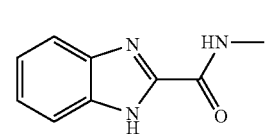 L-55
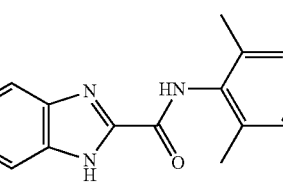 L-56
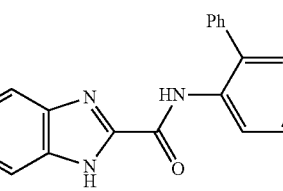 L-57
Type 4
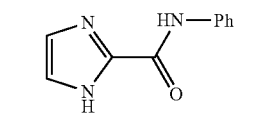 [SMILES: O=C(Nc1ccccc1)c1ncc[nH]1] L-58

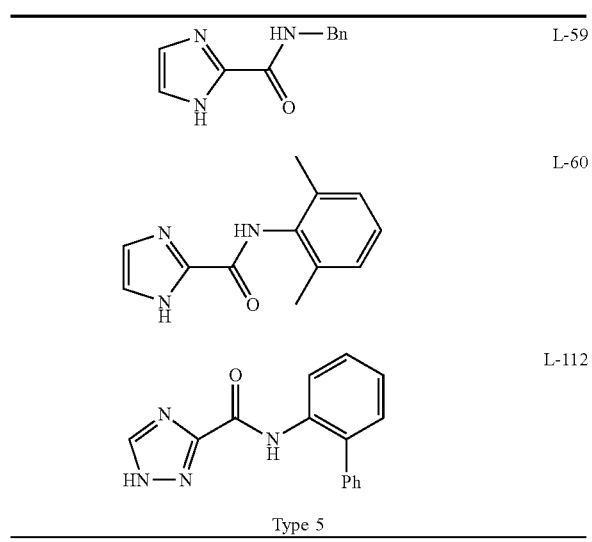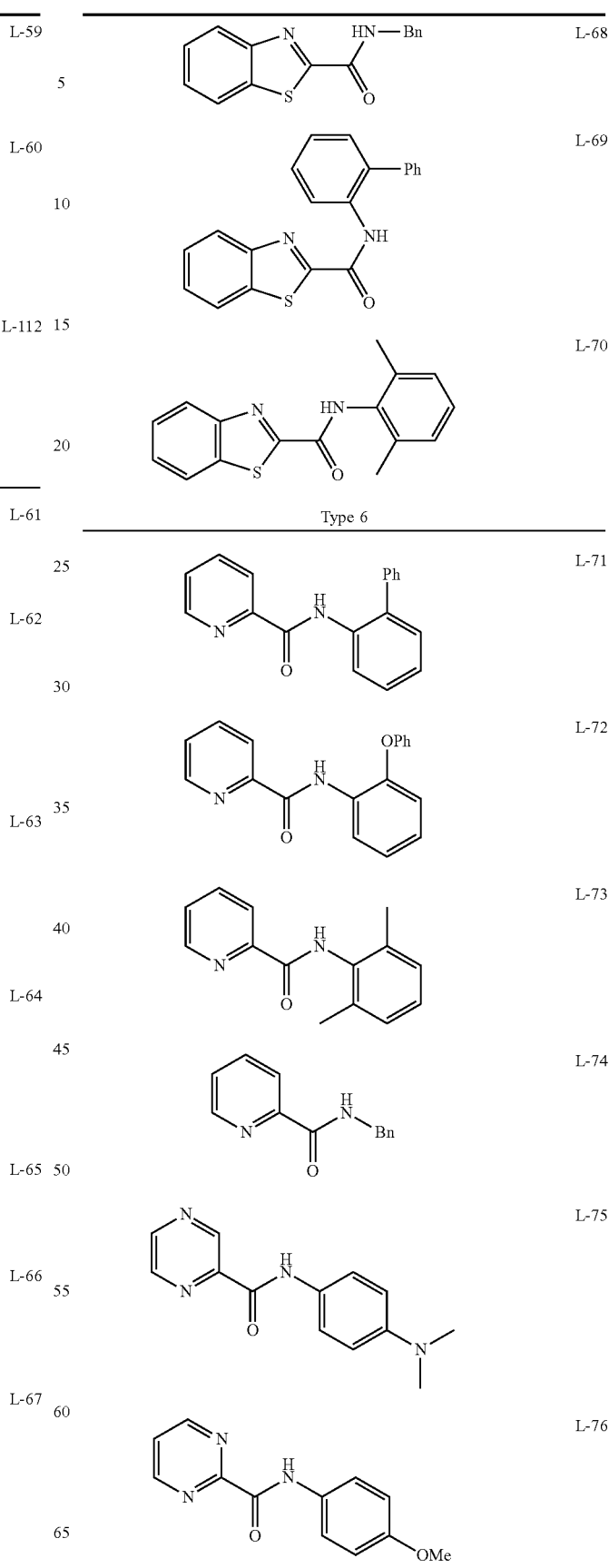

| | |
|---|---|
| L-109 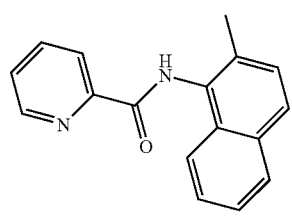 [SMILES: Cc1ccc2ccccc2c1NC(=O)c1ccccn1] | L-84 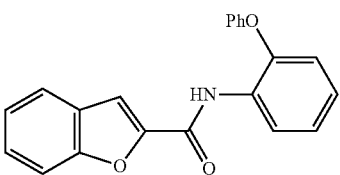 [SMILES: O=C(Nc1ccccc1Oc1ccccc1)c1cc2ccccc2o1] |
| Type 7 | L-85 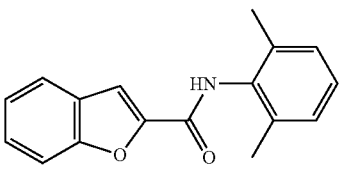 [SMILES: Cc1cccc(C)c1NC(=O)c1cc2ccccc2o1] |
| L-77 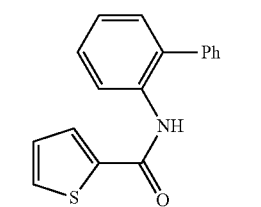 | L-86 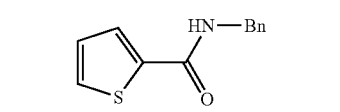 [SMILES: O=C(NCc1ccccc1)c1cccs1] |
| L-78 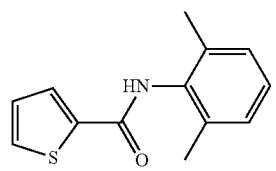 | L-87 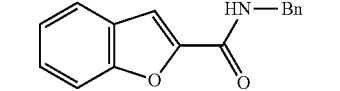 [SMILES: O=C(NCc1ccccc1)c1cc2ccccc2o1] |
| L-79 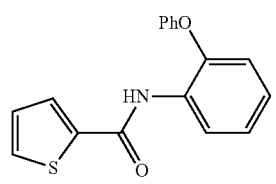 | L-110 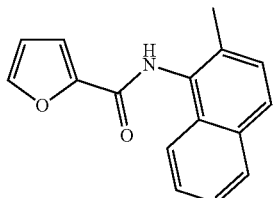 |
| L-80 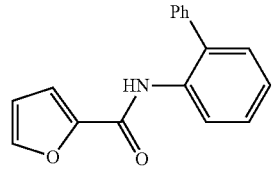 | L-111 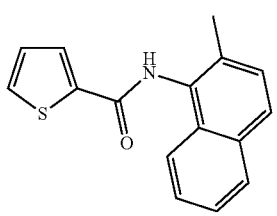 [SMILES: Cc1ccc2ccccc2c1NC(=O)c1cccs1] |
| L-81 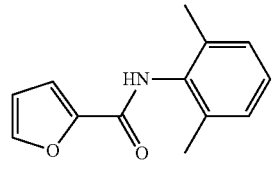 | Type 8 |
| L-82 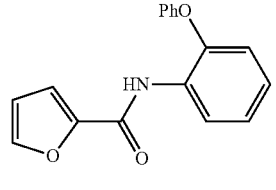 | L-88 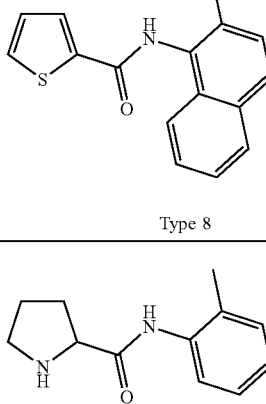 |
| L-83 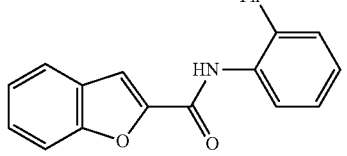 | L-89 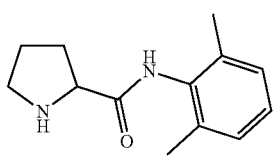 [SMILES: Cc1cccc(C)c1NC(=O)C1CCCN1] |
| | L-90 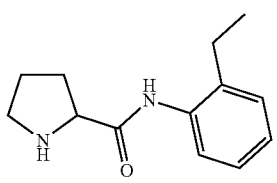 [SMILES: CCc1ccccc1NC(=O)C1CCCN1] |

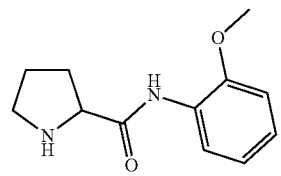 [SMILES: COc1ccccc1NC(=O)C1CCCN1] L-91
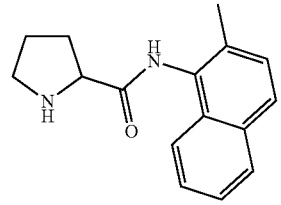 [SMILES: Cc1ccc2ccccc2c1NC(=O)C1CCCN1] L-92
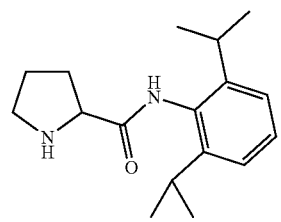 [SMILES: CC(C)c1cccc(C(C)C)c1NC(=O)C1CCCN1] L-93
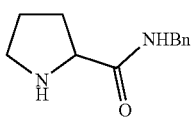 L-94
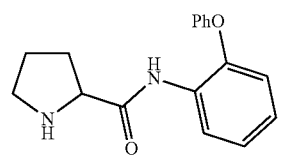 [SMILES: O=C(Nc1ccccc1Oc1ccccc1)C1CCCN1] L-95
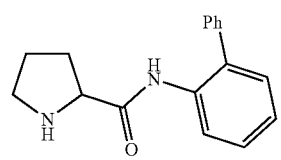 [SMILES: O=C(Nc1ccccc1-c1ccccc1)C1CCCN1] L-96
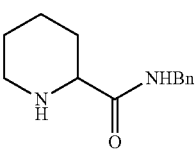 L-97
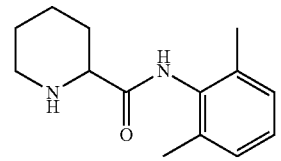 [SMILES: Cc1cccc(C)c1NC(=O)C1CCCCN1] L-98
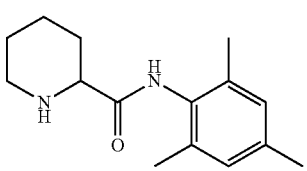 [SMILES: Cc1cc(C)c(NC(=O)C2CCCCN2)c(C)c1] L-99
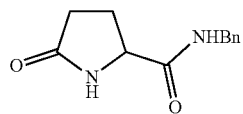 L-100
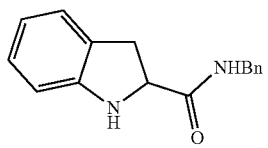 L-101
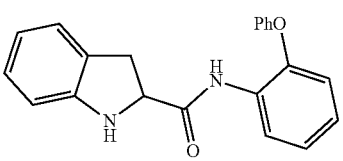 [SMILES: O=C(Nc1ccccc1Oc1ccccc1)C1Cc2ccccc2N1] L-102
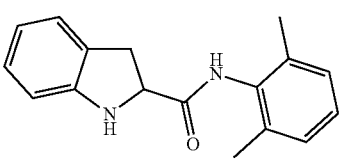 [SMILES: Cc1cccc(C)c1NC(=O)C1Cc2ccccc2N1] L-103
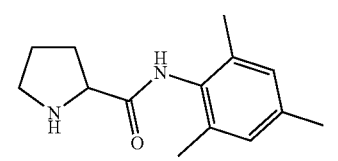 [SMILES: Cc1cc(C)c(NC(=O)C2CCCN2)c(C)c1] L-104
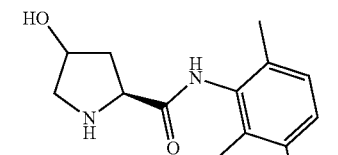 L-105
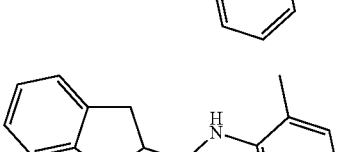 L-106
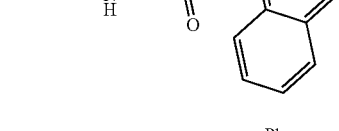 L-107
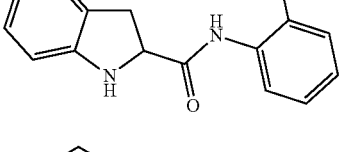 L-108

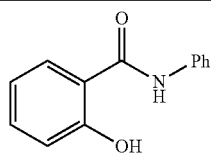

L-113

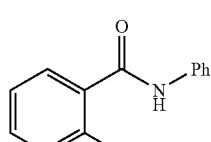

L-114

In the fifth aspect of the invention, a process for the preparation of a compound according to the fourth aspect of the invention is provided, which is carried out by a process selected from (i) or (ii):

Method (i) includes the steps:

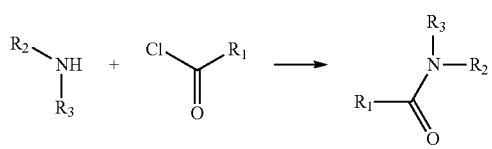

In an inert solvent, reacting $R_2$—NH—$R_3$ with

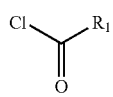

to give the compound of formula (I);

Method (ii) comprises the step:

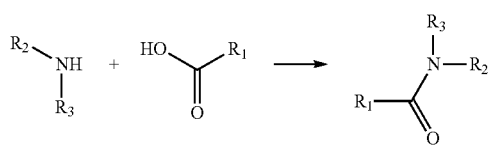

In an inert solvent, reacting $R_2$—NH—$R_3$ with to give the compound of formula (I);

wherein the groups are defined as in the fourth aspect of the present invention.

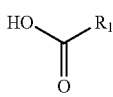

In another preferred embodiment, in the method (i), the inert solvent is selected from the group consisting of tetrahydrofuran, dichloromethane, and DMF.

In another preferred embodiment, in the method (i), the reaction is carried out in the presence of triethylamine.

In another preferred embodiment, in the method (i), the reaction is carried out at 10° C.-80° C. (preferably at room temperature, i.e., 10-40° C.).

In another preferred embodiment, in the method (ii), the inert solvent is selected from the group consisting of tetrahydrofuran, dichloromethane, and DMF.

In another preferred embodiment, in the method (ii), the reaction is carried out at −5° C.-80° C. (preferably at room temperature, i.e., 10-40° C.).

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

After long-term and intensive research, the inventors have provided a class of oxalic acid (mono or bis) amide ligands suitable for copper-catalyzed coupling reaction of aryl chloride. A suitable catalytic system composed by the ligand, copper, bases and solvents can be used for the copper-catalyzed coupling reaction of aryl halides, especially for promoting the copper-catalyzed coupling of aryl chlorides with various nucleophiles to form C—N, C—O, C—S bond which are difficult to occur under conventional conditions, thus synthesizing many useful small molecule compounds. The method has various advantages, such as mild reaction, conditions, wide application range and good industrial application prospect.

Terms

As used herein, the term "halogen" refers to fluorine, chlorine, bromine, and iodine.

The term "halogenated" means that one or more hydrogen atoms on a group are replaced by halogens.

The term "alkyl" refers to a straight or branched alkyl group. When the alkyl group is limited by the number of carbon atoms (such as C1-C6), it means that the alkyl group has 1-6 carbon atoms, such as methyl, ethyl, propyl, isopropyl, butyl, isobutyl, sec-butyl, tert-butyl, or the like.

The term "cycloalkyl" refers to a unit having a saturated or partially saturated monocyclic, bicyclic or tricyclic (cyclo, bridged or spiro) ring system. The cycloalkyl may have 3 to 20 carbon atoms. When a certain cycloalkyl has a carbon number limit (such as C3-C20), it means that the cycloalkyl group has 3-20 carbon atoms, such as cyclopropyl, cyclobutyl, cyclopentyl, cycloheptyl, or the like. The cycloalkyl may be in the monocyclic, multiple cyclic, spiro or bridged ring form.

As used herein, the term "alkoxy" refers to an alkyl (e.g., —O-alkyl, wherein alkyl is as defined above) attached through an oxygen atom, such as, but not limited to, methoxy, ethoxy, propoxy, isopropoxy, butoxy, isobutoxy, sec-butoxy, tert-butoxy, or the like. When the alkoxy is limited by the number of carbon atoms (e.g., C1-C6), it means that the alkoxy has 1-6 carbon atoms.

The term "aryl" refers to an aromatic hydrocarbon group of monocyclic, bicyclic or fused ring which may be substituted or unsubstituted. When an aryl is defined by the number of carbon atoms (e.g., C6-C20), it means that the aryl has 6-20 carbon atoms. Examples of aryl groups are, for example (but not limited to), phenyl, biphenyl, naphthyl, or the like (each carbon atom of which may be optionally substituted).

The term "heteroaryl" refers to a aromatic group of monocyclic, bicyclic or fused ring comprising at least one heteroatom selected from N, O or S. The heteroaryl may be a 3- to 20-membered aromatic ring, having 1 to 5 heteroatoms each independently selected from N, O or S. Examples of heteroaryl are, for example (but not limited to), pyridine, pyrimidine, pyrrole, oxazole, indole, furan, benzofuran, thiophene, or the like.

The term "heterocyclyl" refers to a saturated or partially saturated substituent of a monocyclic or fused ring comprising at least one identical or different heteroatom selected from N, O or S. The heterocyclic group may be a 3- to 20-membered heterocyclic group having 1 to 5 heteroatoms each independently selected from N, O or S. Examples of the heterocyclic group are, for example, but not limited to, a nitrogen heterocyclic group, an oxaheterocyclic group, a thioheterocyclic group, an oxynitridyl group, and the like.

The term "ester group" refers to a group having the structure of "alkyl-COO—", wherein the alkyl is as defined above.

The term "acyl" refers to a group having the structure "alkyl-CO—", wherein the alkyl is as defined above.

The term "amido" refers to a group having the structure "alkyl NHC(O)—" or "aryl NHC(O)—", wherein the alkyl, aryl are as defined above.

Ligand

Unless otherwise stated, a ligand as referred herein refers to a ligand used in a copper-catalyzed coupling reaction of aryl chloride.

The ligand which can be used in the present invention has a structure as shown in the above formula (I), and in a preferred embodiment of the present invention, the ligand has the following structure (each group is as described above):

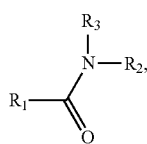

I

Wherein $R_1$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R^2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be of monocyclic, multiple-cyclic, Spiro or bridged ring structure;

$R_3$ is selected from the group consisting of hydrogen, and a substituted or unsubstituted C1-C6 alkyl;

or $R_2$ and $R_3$ together with the connected N atom to form a 3- to 20-membered saturated or unsaturated ring (e.g., a substituted or unsubstituted pyrrole, indole, azole, benzoxazole, and aromatic heterocycle).

In another preferred embodiment, in the compound, any one of $R_1$, $R_2$, and $R_3$ is the group corresponding to the group in the specific compounds in the present application.

In another preferred embodiment, the structure of the ligand is as shown in Formula II:

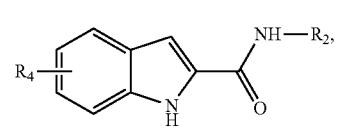

II

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

$R_4$ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure.

In another preferred embodiment, the number of $R_4$ substituent is 1-4, the substitution position may be ortho or meta, and each $R_4$ may be the same or different. When the number of $R_4$ substituent is ≤2, the adjacent $R_4$ may be linked to form a ring.

In another preferred embodiment, the structure of the ligand is as shown in Formula

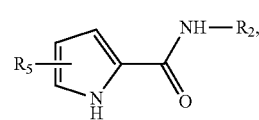

III

Wherein $R_2$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

R₅ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of R₅ substituent is 1-3, the substitution position may be ortho or meta, and each R₅ may be the same or different. When the number of R₅ substituent is ≤2, the adjacent R₅ may be linked to form a ring.

In another preferred embodiment, the structure of the ligand is as shown in Formula VI:

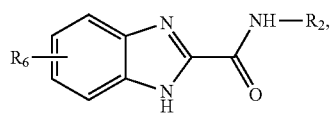

VI

Wherein R₂ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

R₆ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure.

In another preferred embodiment, the number of R₆ substituent is 1-4, the substitution position may be ortho or meta, and each R₆ may be the same or different. When the number of R₆ substituent is ≤2, the adjacent R₆ may be linked to form a ring.

In another preferred embodiment, the structure of the ligand is as shown in Formula Va, Vb, or Vc:

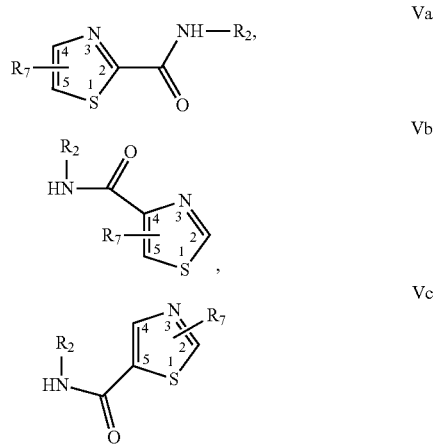

Wherein R₂ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

R₇ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of R₇ substituent is 1 or 2, and each R₇ may be the same or different. When the number of R₇ substituent is 2, the adjacent R₇ may be linked to form a ring (preferably 6-20 membered aromatic rings, such as benzene rings).

In another preferred embodiment, the structure of the compound is as shown in the formula VIa, VIb, or VIc:

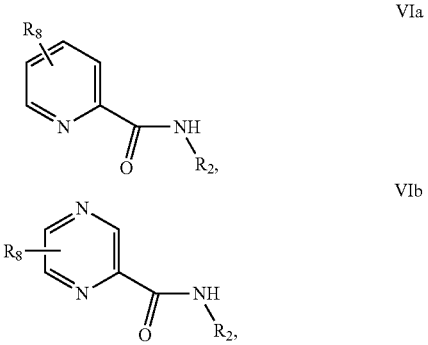

VIc

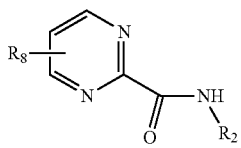

Wherein R₂ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

R₈ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure.

In another preferred embodiment, the number of R₈ substituent is 1-3, and each R₈ may be the same or different. When the number of R₈ substituent is ≤2, the adjacent R₈ may be linked to form a ring (preferably 6-20 membered saturated or unsaturated aromatic rings).

In another preferred embodiment, the structure of the ligand is as shown in Formula VII:

VII

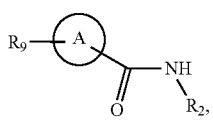

Wherein R₂ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

R₉ is selected from the group consisting of H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, Spiro or bridged ring structure;

A is 3- to 12-membered saturated or unsaturated heterocyclic group wherein the heterocyclic group contains 1 to 4 heteroatoms each independently selected from N, O, and S.

In another preferred embodiment, A is a 5-membered heterocyclic ring containing one N atom.

In another preferred embodiment, A is furan, thiophene or pyrrole.

In another preferred embodiment, the number of R₉ substituent is 1-3, and each R₉ may be the same or different. When the number of R₉ substituent is ≤2, the adjacent two R₉ may be linked to form a ring (preferably 6-20 membered saturated or unsaturated aromatic rings, such as benzene ring).

Each of the above ligands may be obtained commercially, or prepared according to the preferred methods provided herein.

It should be understood that since the bond energy of C—Br and C—I bonds is lower than that of C—Cl bond, the coupling reaction of aryl bromide and aryl iodide is more likely to occur, compared with the aryl chloride under the same conditions. Therefore, in addition to the coupling reaction of aryl chloride, the above ligand can also be used in the coupling reaction of aryl bromide or aryl iodide which is conventional in the art.

Copper-Catalyzed Coupling Reaction of Aryl Chlorides

The present invention also provides a copper-catalyzed coupling reaction method for aryl chlorides, which comprises carrying out the above reaction by using a compound of the formula (I) as described above as a ligand.

Generally, aryl iodide and aryl bromide exhibit higher reactivity, so that the corresponding coupling reaction can be better realized under the catalyzation of transition metals such as palladium, copper, nickel, etc.; compared with brominated (iodinated) aromatic hydrocarbons, chlorinated aromatic hydrocarbons are cheaper and more promising; however, due to the high energy of C—Cl bond, the aryl chlorides are difficult to react under the conventional catalytic conditions for aryl bromides and aryl iodides.

The ligands and reaction conditions can be optimized for different reactants within the scope of the present invention, thereby selecting the most suitable ligand type and reaction conditions (such as temperature, solvent, reactant ratio, reaction time, etc.). After the disclosure of the present application, the above optimization is within the skill of those skilled in the art.

Several of the most preferred copper-catalyzed coupling reactions of aryl chloride are as follows:

1. Copper-Catalyzed C—N Coupling Reaction of Aryl Chlorides Promoted by Heterocyclic Carboxylic Acid Amide Ligands In the above reaction, the selection of the coupling reagent is not particularly limited, which may be the corresponding primary or secondary amine, or may be another ammonia source such as ammonia gas, ammonium hydroxide or ammonium salt, sodium azide or the like. The specific reaction process is as follows:

In the case where the coupling reagent is a primary or secondary amine, the reaction is as follows:

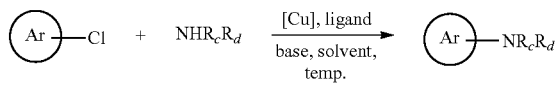

wherein the groups are defined as above.

is selected from the group consisting of a substituted or unsubstituted C6-C20 aryl, substituted or unsubstituted 3- to 20-membered heteroaryl; wherein said "substituted" refers to one or more hydrogen atoms on the aryl group are substituted by substituents selected from the group consisting of halogen, nitro, cyano, a substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 amide group (alkyl NHC(O)—, aryl NHC(O)—), —COOH, hydroxy-C1-C10 alkylene, MeS—, sulfonyl, sulfonamide group;

$R_c$, $R_d$ are each independently selected from the group consisting of H, a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure; the "substituted" means that one or more hydrogen atoms on the group are substituted by substituents selected from the group consisting of halogen, a C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 amide (alkyl NHC(O)—, aryl NHC(O)—), —COOH.

In the above reaction, the copper catalyst may be CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, preferably CuI.

The ligand is not particularly limited, and may be any of the ligands described above, preferably L53 or L103.

A preferred base may be potassium carbonate, cesium carbonate, potassium phosphate, sodium carbonate, sodium hydrogen carbonate or potassium hydrogencarbonate, preferably potassium phosphate, cesium carbonate, and most preferably potassium phosphate.

The solvent can be DMSO, DMF, DMA, NMP, acetonitrile, tert-butanol, isopropanol, THF, 1,4-dioxane, preferably DMSO, DMF, most preferably DMSO.

The reaction temperature is 50-180° C., preferably 100-130° C.

In the cases where the coupling reagent is other ammonia source, the reaction is as follows:

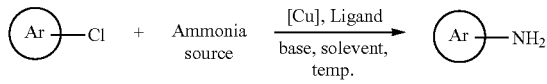

wherein the groups are defined as above.

is selected from the group consisting of a substituted or unsubstituted C6-C20 aryl, substituted or unsubstituted 3- to 20-membered heteroaryl; wherein said "substituted" means that one or more hydrogen atoms on the aryl group are substituted by substituents selected from the group consisting of halogen, nitro, cyano, a substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—, aryl NHC (O)—), C2-C10 amide group (alkyl NHC(O)—), —COOH, hydroxy-C1-C10 alkylene, MeS—, sulfonyl, sulfonamide group;

The ammonia source is selected from the group consisting of ammonia gas, ammonium hydroxide, ammonium chloride, ammonium carbonate, ammonium hydrogen carbonate, ammonium sulfate, ammonium nitrate, ammonium phosphate, diammonium hydrogen phosphate, sodium azide, preferably ammonia gas, ammonium hydroxide, ammonium chloride and diammonium hydrogen phosphate.

When the ammonia source is an ammonium salt, the reaction is carried out in the presence of a strong base (preferably in the presence of KOH).

The copper catalyst may be CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, preferably CuI.

The ligand is any one of the above, preferably L13, L15 or L31.

The base may be potassium carbonate, cesium carbonate, potassium phosphate, sodium carbonate, sodium hydrogen carbonate or potassium hydrogen carbonate, preferably cesium carbonate or potassium phosphate, most preferably potassium phosphate.

The solvent can be DMSO, DMF, DMA, NMP, acetonitrile, tert-butanol, isopropanol, THF, 1,4-dioxane, preferably DMSO, DMF, most preferably DMSO.

The reaction temperature is 50-180° C., preferably 100-130° C.

2. Copper-Catalyzed C—O Coupling Reaction of Aryl Chlorides Promoted by Heterocyclic Carboxylic Acid Amide Ligands

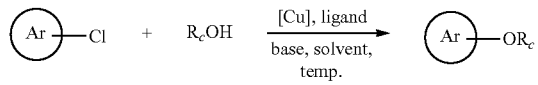

wherein the groups are defined as above.

is selected from the group consisting of a substituted or unsubstituted C6-C20 aryl, substituted or unsubstituted 3- to 20-membered heteroaryl; wherein said "substituted" means that one or more hydrogen atoms on the aryl group are substituted by substituents selected from the group consisting of halogen, nitro, cyano, a substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 amide group (alkyl NHC(O)—, aryl NHC(O)—), —COOH, hydroxy-C1-C10 alkylene, MeS—, sulfonyl, sulfonamide group;

$R_c$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkylaryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

the "substituted" means that one or more hydrogen atoms on the group are substituted by substituents selected from the group consisting of halogen, a C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 amide group (alkyl NHC(O)—, aryl NHC(O)—), —COOH, —CN, MeS—, sulfonyl, sulfonamide group.

The copper catalyst may be CuI, CuBr, CuCl, CuTc, $Cu(OAc)_2$, $CuSO_4$, $Cu_2O$, $CuBr_2$, $CuCl_2$, CuO, CuSCN, CuCN, $Cu(acac)_2$, preferably CuI.

The ligand is any one of the above, preferably L13, L15 or L35.

The base may be potassium carbonate, cesium carbonate, potassium phosphate, sodium carbonate, sodium hydrogen carbonate or potassium hydrogencarbonate, preferably potassium phosphate.

The solvent can be DMSO, DMF, DMA, NMP, acetonitrile, tert-butanol, isopropanol, THF, 1,4-dioxane, preferably DMSO.

The reaction temperature is 50-180° C., preferably 100-130° C.

3. Copper-Catalyzed C—S Coupling Reaction of Aryl Chlorides Promoted by Heterocyclic Carboxylic Acid Amide Ligands

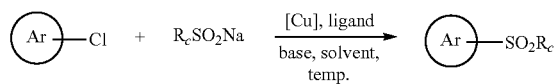

Wherein the groups are defined as above.

is selected from the group consisting of a substituted or unsubstituted C6-C20 aryl, substituted or unsubstituted 3- to 20-membered heteroaryl; wherein said "substituted" means that one or more hydrogen atoms on the aryl group are substituted by substituents selected from the group consisting of halogen, nitro, cyano, a substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 amide group (alkyl NHC(O)—, aryl NHC(O)—), —COOH, hydroxy-C1-C10 alkylene, MeS—, sulfonyl, sulfonamide group;

$R_c$ is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkylaryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of N, O and S; the cycloalkyl or heterocyclic group may be of monocyclic, multiple-cyclic, spiro or bridged ring structure;

the "substituted" means that one or more hydrogen atoms on the group are substituted by substituents selected from the group consisting of halogen, a C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 amide group (alkyl NHC(O)—, aryl NHC(O)—), —COOH, —CN, MeS—, sulfonyl, sulfonamide group.

The ligand is any one described in 1, preferably L-92 or L-105.

The base may be potassium carbonate, cesium carbonate, potassium phosphate, sodium carbonate, sodium hydrogen carbonate or potassium hydrogencarbonate, preferably potassium phosphate.

The solvent can be DMSO, DMF, DMA, NMP, acetonitrile, tert-butanol, isopropanol, THF, 1,4-dioxane, preferably DMSO.

The reaction temperature is 50-180° C., preferably 100-130° C.

Compared with the Prior Art, the Main Advantages of the Present Invention Includes:

1. A catalytic system capable of efficiently performing copper-catalyzed coupling reaction of aryl chloride is provided, which is able to promote coupling reaction of aryl chloride which are difficult to be carried out under conventional aryl bromide and aryl iodide coupling systems, and is of good substrate compatibility as well as wide application range.

2. Compared with the coupling reaction method of aryl chloride in the prior art, the method of the invention adopts a copper catalyst system with lower cost, while the ligand is of simple structure, easily to be prepared, and used in less amount, and the reaction is economical.

3. Compared with other aryl halides, the raw material, aryl chloride used in the catalytic system of the invention possesses advantages, such as low raw material cost, wide source, and good prospect of large-scale application.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are calculated by weight.

Example 1: Ligand Types 1-4, Prepared by the Acyl Chloride Method

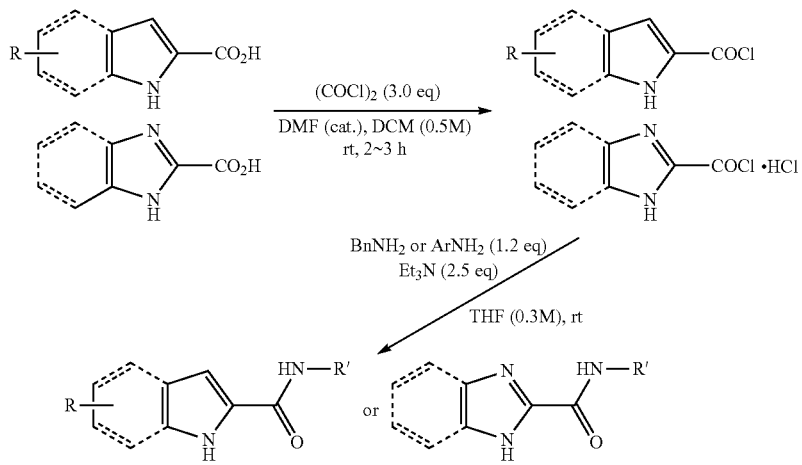

Benzimidazole-2-carboxylic acid or indol-2-carboxylic acid (1.0 eq) was added into a single-opening bottle, and DCM (0.5 M) and 1-2 drops of DMF were added and stirred (some substrates did not dissolve), the bottle was sealed with a rubber stopper, and a balloon was connected. Oxalyl chloride (3.0 eq) was added dropwise into the system, and a large amount of gas was released during the dropping process (the balloon was expanded by HCl, $CO_2$, CO gas). After the addition, the mixture was stirred at room temperature for 2-3 hours, and the stirrer was taken out after the stirring was stopped. DCM and excess oxalyl chloride were removed by rotary evaporation, dried by suction to obtain the solid, which was acid chloride (there may be some salt formed with hydrochloric acid, so the reaction with the amine in the next step requires an excess of triethylamine). In the above formula, R' corresponds to $R_2$ of the formula I of the present invention.

Benzylamine or substituted aromatic amine was dissolved in THF, and triethylamine was added, while the above acid chloride was added into the system under stirring (the solid can be directly scraped off and added in portions, or dissolved in THF and added dropwise). After the addition, the mixture was stirred at room temperature until the reaction was completed. The THF was removed by rotary distillation and dried. Water was added, suction filtered, and washed with cold diethyl ether to provide the solid.

| Structure of the ligand | Structure characterization |
|---|---|
| L-1, yield 90% | $^1$H NMR (400 MHz, CDCl$_3$) δ 9.33 (s, 1H), 7.64 (dq, J = 8.1, 1.0 Hz, 1H), 7.44 (dq, J = 8.2, 0.9 Hz, 1H), 7.41-7.34 (m, 4H), 7.34-7.27 (m, 2H), 7.18-7.11 (m, 1H), 6.84 (dd, J = 2.2, 1.0 Hz, 1H), 6.45 (s, 1H), 4.69 (d, J = 5.8 Hz, 2H); HRMS (ESI) calcd for C$_{16}$H$_{15}$N$_2$O (M + H)$^+$ 251.1179, found 251.1178. |
| L-2, yield 92% | $^1$H NMR (400 MHz, CDCl$_3$) 9.68 (s, 1H), 7.93 (s, 1H), 7.71-7.64 (m, 3H), 7.49-7.43 (m, 1H), 7.43-7.36 (m, 2H), 7.35-7.28 (m, 1H), 7.22-7.14 (m, 2H), 7.03 (dd, J = 2.1, 0.9 Hz, 1H); HRMS (ESI) calcd for C$_{15}$H$_{13}$N$_2$O (M + H)$^+$ 237.1022, found 237.1025. |
| L-3, yield 88% | $^1$H NMR (400 MHz, CDCl$_3$) δ 9.77 (s, 1H), 8.63 (s, 1H), 8.53 (dd, J = 7.9, 1.7 Hz, 1H), 7.70 (dd, J = 8.0, 1.0 Hz, 1H), 7.49 (dd, J = 8.3, 0.9 Hz, 1H), 7.35-7.27 (m, 1H), 7.20-7.14 (m, 1H), 7.14-7.07 (m, 1H), 7.07-7.01 (m, 2H), 6.95 (dd, J = 8.0, 1.5 Hz, 1H), 3.98 (s, 3H); HRMS (ESI) calcd for C$_{16}$H$_{15}$N$_2$O$_2$ (M + H)$^+$ 267.1128, found 267.1131. |

| Structure of the ligand | Structure characterization |
|---|---|
| 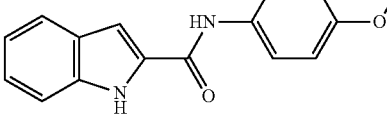<br>L-4, yield 90% | $^1$H NMR (400 MHz, d6-DMSO) δ 11.71 (s, 1H), 10.11 (s, 1H), 7.77-7.61 (m, 3H), 7.50-7.43 (m, 1H), 7.38 (d, J = 2.1 Hz, 1H), 7.21 (ddd, J = 8.1, 6.9, 1.1 Hz, 1H), 7.06 (t, J = 7.5 Hz, 1H), 7.01-6.89 (m, 2H), 3.75 (s, 3H); HRMS (ESI) calcd for C$_{16}$H$_{14}$N$_2$NaO$_2$ (M + Na)$^+$ 289.0947, found 289.0948. |
| 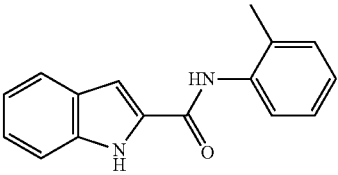 [SMILES: Cc1ccccc1NC(=O)c1cc2ccccc2[nH]1]<br>L-6, yield 95% | $^1$H NMR (500 MHz, d6-DMSO) δ 11.71 (s, 1H), 9.86 (s, 1H), 7.66 (dd, J = 8.0, 1.0 Hz, 1H), 7.46 (dd, J = 8.3, 1.0 Hz, 1H), 7.41-7.33 (m, 2H), 7.30 (dd, J = 7.5, 1.6 Hz, 1H), 7.27-7.16 (m, 3H), 7.07 (ddd, J = 8.0, 6.9, 1.0 Hz, 1H), 2.27 (s, 3H); HRMS (ESI) calcd for C$_{16}$H$_{14}$N$_2$NaO (M + Na)$^+$ 273.0998, found 273.0999. |
| 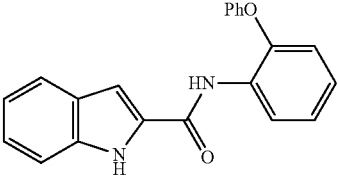 [SMILES: O=C(Nc1ccccc1Oc1ccccc1)c1cc2ccccc2[nH]1]<br>L-7, yield 85% | $^1$H NMR (400 MHz, CDCl$_3$) δ 9.32 (s, 1H), 8.64-8.51 (m, 2H), 7.65 (d, J = 8.0 Hz, 1H), 7.46 (d, J = 8.3 Hz, 1H), 7.40 (t, J = 7.8 Hz, 2H), 7.31 (t, J = 7.6 Hz, 1H), 7.22-7.14 (m, 3H), 7.13-7.09 (m, 2H), 7.06 (td, J = 7.8, 1.6 Hz, 1H), 6.92 (d, J = 8.0 Hz, 1H), 6.90-6.86 (m, 1H); HRMS (ESI) calcd for C$_{21}$H$_{17}$N$_2$O$_2$ (M + H)$^+$ 329.1285, found 329.1290. |
| 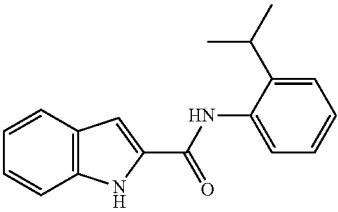 [SMILES: CC(C)c1ccccc1NC(=O)c1cc2ccccc2[nH]1]<br>L-10, yield 86% | $^1$H NMR (400 MHz, d6-DMSO) δ 11.74 (s, 1H), 9.94 (s, 1H), 7.66 (d, J = 8.0 Hz, 1H), 7.46 (d, J = 8.2 Hz, 1H), 7.43-7.34 (m, 2H), 7.34-7.17 (m, 4H), 7.11-7.03 (m, 1H), 3.23 (h, J = 6.7 Hz, 1H), 1.17 (d, J = 6.9 Hz, 6H); HRMS (ESI) calcd for C$_{18}$H$_{18}$N$_2$NaO (M + Na)$^+$ 301.1311, found 301.1310. |
| 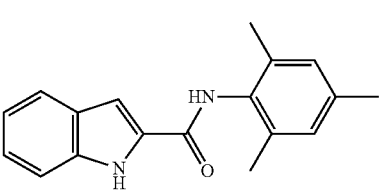 [SMILES: Cc1cc(C)c(NC(=O)c2cc3ccccc3[nH]2)c(C)c1]<br>L-12, yield 90% | $^1$H NMR (400 MHz, D6-DMSO) δ 11.71 (s, 1H), 9.73 (s, 1H), 7.65 (d, J = 7.9 Hz, 1H), 7.44 (d, J = 8.2 Hz, 1H), 7.35 (d, J = 1.3 Hz, 1H), 7.20 (t, J = 7.3 Hz, 1H), 7.06 (t, J = 7.4 Hz, 1H), 6.95 (s, 2H), 2.27 (s, 3H), 2.17 (s, 6H). $^{13}$C NMR (101 MHz, D6-DMSO) δ 159.78, 136.58, 135.74, 135.45, 132.18, 131.42, 128.39, 127.12, 123.48, 121.56, 119.85, 112.34, 103.09, 20.57, 18.06. ESI-MS m/z 279.3(M + H)$^+$; HRMS Calcd. For C$_{18}$H$_{19}$N$_2$O (M + H)$^+$ requires 279.1492 found: 279.1496. |
| 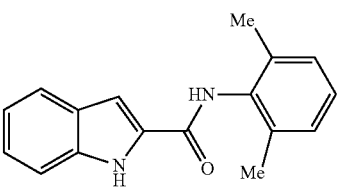 [SMILES: Cc1cccc(C)c1NC(=O)c1cc2ccccc2[nH]1]<br>L-13, yield 91% | $^1$H NMR (500 MHz, d6-DMSO) δ 11.70 (s, 1H), 9.79 (s, 1H), 7.66 (dd, J = 8.0, 1.1 Hz, 1H), 7.46 (dd, J = 8.2, 1.0 Hz, 1H), 7.37 (dd, J = 2.2, 0.9 Hz, 1H), 7.21 (ddd, J = 8.2, 7.0, 1.2 Hz, 1H), 7.14 (s, 3H), 7.07 (ddd, J = 8.0, 7.0, 1.0 Hz, 1H), 2.22 (s, 6H); HRMS (ESI) calcd for C$_{17}$H$_{17}$N$_2$O (M + H)$^+$ 265.1335, found 265.1338. |

-continued

| Structure of the ligand | Structure characterization |
|---|---|
| 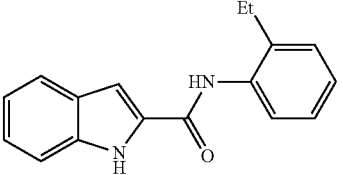 [SMILES: CCc1ccccc1NC(=O)c1cc2ccccc2[nH]1]<br>L-14, yield 89% | ¹H NMR (500 MHz, d6-DMSO) δ 11.74 (s, 1H), 9.89 (s, 1H), 7.67 (d, J = 8.0, Hz, 1H), 7.48 (dd, J = 8.2, 0.5 Hz, 1H), 7.41-7.34 (m, 2H), 7.32 (dd, J = 6.6, 2.6 Hz, 1H), 7.29-7.23 (m, 2H), 7.21 (dd, J = 8.1, 1.0 Hz, 1H), 7.11-7.05 (m, 1H), 2.67 (q, J = 7.5 Hz, 2H), 1.15 (t, J = 7.6 Hz, 3H).; ¹³C NMR (126 MHz, d6-DMSO) δ 160.23, 139.83, 136.69, 135.27, 131.43, 128.62, 127.54, 127.10, 126.50, 126.09, 123.58, 121.62, 119.86, 112.38, 103.47, 24.07, 14.18. ESI-MS m/z 265.3(M + H)⁺; HRMS Calcd. For $C_{17}H_{16}N_2O$ (M + H)⁺ requires 264.1263; found: 264.1262 |
| 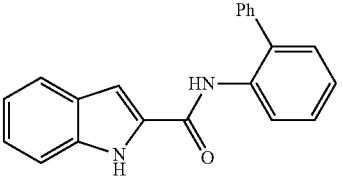<br>L-15, yield 85% | ¹H NMR (400 MHz, D6-DMSO) δ 11.63 (s, 1H), 9.81 (s, 1H), 7.61 (t, J = 7.5 Hz, 1H), 7.55 (d, J = 7.8 Hz, 1H), 7.49-7.34 (m, 8H), 7.33-7.25 (m, 1H), 7.22-7.15 (m, 1H), 7.10 (s, 1H), 7.07-7.00 (m, 1H).; ¹³C NMR (101 MHz, D6-DMSO) δ 160.21, 139.10, 137.96, 136.60, 134.38, 131.33, 130.36, 128.60, 128.30, 128.14, 127.87, 127.17, 126.98, 126.70, 123.57, 121.60, 119.82, 112.33, 103.34. ESI-MS m/z 313.3(M + H)⁺; HRMS Calcd. For $C_{21}H_{16}N_2NaO$ (M + Na)⁺ requires 335.1155; found: 335.1158. |
| 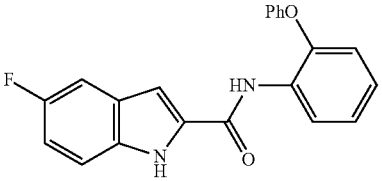 [SMILES: O=C(Nc1ccccc1Oc1ccccc1)c1cc2cc(F)ccc2[nH]1]<br>L-20, yield 90% | ¹H NMR (400 MHz, d6-DMSO) δ 11.84 (s, 1H), 9.87 (s, 1H), 7.76 (dd, J = 7.1, 2.4 Hz, 1H), 7.45-7.38 (m, 2H), 7.38-7.31 (m, 2H), 7.27-7.19 (m, 3H), 7.12-6.96 (m, 5H); HRMS (ESI) calcd for $C_{21}H_{15}FN_2NaO_2$ (M + Na)⁺ 369.1010, found 369.1010. |
| 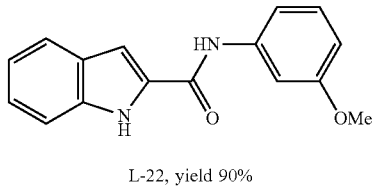<br>L-22, yield 90% | ¹H NMR (400 MHz, D6-DMSO) δ 11.74 (s, 1H), 10.14 (s, 1H), 7.68 (d, J = 8.0 Hz, 1H), 7.64 (d, J = 5.5 Hz, 2H), 7.48 (d, J = 8.3 Hz, 1H), 7.44 (s, 1H), 7.24 (dt, J = 9.8, 7.6 Hz, 2H), 7.08 (t, J = 7.4 Hz, 1H), 6.93 (d, J = 7.5 Hz, 1H), 2.33 (s, 3H); ¹³C NMR (101 MHz, D6-DMSO) δ 159.67, 138.89, 137.84, 136.81, 131.56, 128.55, 127.05, 124.25, 123.75, 121.74, 120.66, 119.91, 117.35, 112.39, 103.83, 21.25. HRMS Calcd. For $C_{16}H_{14}N_2NaO$ (M + Na)⁺ requires 273.0998; found: 273.1004. |
| 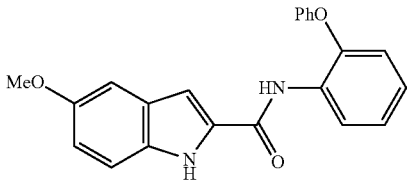 [SMILES: COc1ccc2[nH]c(C(=O)Nc3ccccc3Oc3ccccc3)cc2c1]<br>L-26, yield 93% | ¹H NMR (400 MHz, d6-DMSO) δ 11.60 (s, 1H), 9.74 (s, 1H), 7.83-7.75 (m, 1H), 7.39-7.29 (m, 3H), 7.26-7.19 (m, 2H), 7.16 (d, J = 1.4 Hz, 1H), 7.12-7.06 (m, 2H), 7.05-6.97 (m, 3H), 6.85 (dd, J = 8.9, 2.4 Hz, 1H), 3.75 (s, 3H); HRMS (ESI) calcd for $C_{22}H_{19}N_2O_3$ (M + H)⁺ 359.1390, found 359.1390. |
| 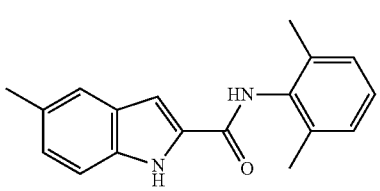 [SMILES: Cc1ccc2[nH]c(C(=O)Nc3c(C)cccc3C)cc2c1]<br>L-28, yield 80% | ¹H NMR (400 MHz, d6-DMSO) δ 11.57 (s, 1H), 9.74 (s, 1H), 7.42 (s, 1H), 7.33 (d, J = 8.4 Hz, 1H), 7.26 (d, J = 2.1 Hz, 1H), 7.14 (s, 3H), 7.04 (dd, J = 8.4, 1.7 Hz, 1H), 2.38 (s, 3H), 2.21 (s, 6H); HRMS (ESI) calcd for $C_{18}H_{19}N_2O$ (M + H)⁺ 279.1492, found 279.1494. |

| Structure of the ligand | Structure characterization |
|---|---|
| 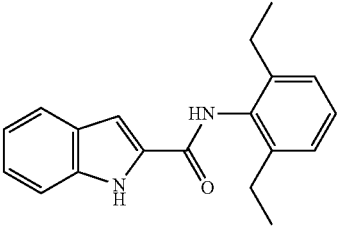 [SMILES: CCc1cccc(CC)c1NC(=O)c1cc2ccccc2[nH]1]<br>L-29, yield 92% | ¹H NMR (400 MHz, D6-DMSO) δ 11.73 (s, 1H), 9.79 (s, 1H), 7.66 (d, J = 8.0 Hz, 1H), 7.44 (d, J = 8.2 Hz, 1H), 7.36 (d, J = 1.4 Hz, 1H), 7.28-7.14 (m, 4H), 7.09-7.04 (m, 1H), 2.58 (q, J = 7.5 Hz, 4H), 1.12 (t, J = 7.6 Hz, 6H). ¹³C NMR (101 MHz, D6-DMSO) δ 160.51, 141.96, 136.61, 133.67, 131.36, 127.43, 127.11, 126.17, 123.53, 121.57, 119.88, 112.36, 103.16, 24.56, 14.58. ESI-MS m/z 293.3(M + H)⁺; HRMS Calcd. For $C_{19}H_{21}N_2O$ (M + H)⁺ requires 293.1648; found: 293.1651. |
| 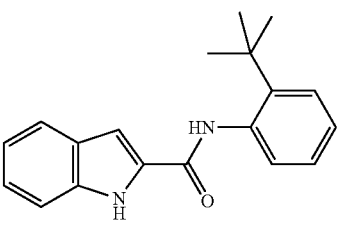 [SMILES: CC(C)(C)c1ccccc1NC(=O)c1cc2ccccc2[nH]1]<br>L-30, yield 90% | ¹H NMR (400 MHz, D6-DMSO) δ 11.72 (s, 1H), 9.79 (s, 1H), 7.66 (d, J = 8.0 Hz, 1H), 7.47 (ddd, J = 12.2, 8.1, 2.1 Hz, 2H), 7.38-7.32 (m, 1H), 7.32-7.25 (m, 2H), 7.24-7.15 (m, 2H), 7.09-7.03 (m, 1H), 1.36 (s, 9H).; ¹³C NMR (101 MHz, D6-DMSO) δ 160.93, 147.29, 136.62, 135.62, 132.07, 131.82, 127.33, 127.14, 126.88, 126.54, 121.64, 119.85, 112.37, 103.34, 34.96, 30.92. ESI-MS m/z 293.3(M + H)⁺; HRMS Calcd. For $C_{19}H_{21}N_2O$ (M + H)⁺ requires 293.1648.; found: 293.1651. |
| 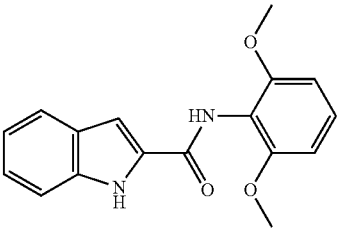 [SMILES: COc1cccc(OC)c1NC(=O)c1cc2ccccc2[nH]1]<br>L-31, yield 89% | ¹H NMR (400 MHz, D6-DMSO) δ 11.60 (s, 1H), 9.37 (s, 1H), 7.64 (d, J = 7.4 Hz, 1H), 7.45 (d, J = 7.8 Hz, 1H), 7.32 (s, 1H), 7.30-7.23 (m, 1H), 7.23-7.15 (m, 1H), 7.05 (t, J = 6.8 Hz, 1H), 6.74 (d, J = 8.2 Hz, 2H), 3.75 (s, 6H). ¹³C NMR (101 MHz, D6-DMSO) δ 159.86, 156.34, 136.46, 131.75, 127.89, 127.16, 123.36, 121.57, 119.73, 114.33, 112.31, 104.48, 103.34, 55.73. ESI-MS m/z 297.3(M + H)⁺; HRMS Calcd. For $C_{17}H_{17}N_2O_3$ (M + H)⁺ requires 297.1234 found: 297.1236. |
| 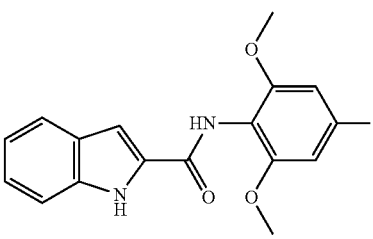<br>L-32, yield 87% | ¹H NMR (400 MHz, D6-DMSO) δ 11.56 (s, 1H), 9.21 (s, 1H), 7.63 (d, J = 1.9 Hz, 1H), 7.43 (dd, J = 8.2, 0.6 Hz, 1H), 7.29 (s, 1H), 7.22-7.14 (m, 1H), 7.04 (t, J = 7.2 Hz, 1H), 6.31 (s, 2H), 3.82 (s, 3H), 3.74 (s, 7H). ¹³C NMR (101 MHz, D6-DMSO) δ 160.12, 159.50, 156.94, 136.40, 131.86, 127.16, 123.26, 121.51, 119.68, 112.27, 107.28, 103.14, 91.07, 55.72. ESI-MS m/z 327.4(M + H)⁺; HRMS Calcd. For $C_{18}H_{19}N_2O_4$ (M + H)⁺ requires 327.1339.; found: 327.1342. |
| 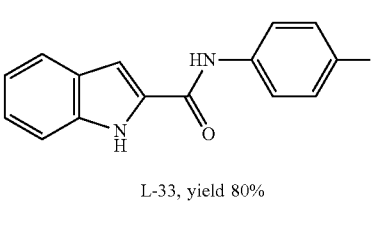<br>L-33, yield 80% | ¹H NMR (400 MHz, D6-DMSO) δ 11.91 (s, 1H), 10.63 (s, 1H), 8.00 (d, J = 8.9 Hz, 2H), 7.75 (d, J = 5.6 Hz, 1H), 7.67 (d, J = 8.0 Hz, 1H), 7.52 (d, J = 1.4 Hz, 1H), 7.47 (dd, J = 8.3, 0.7 Hz, 1H), 7.27-7.19 (m, 1H), 7.11-7.04 (m, 1H), 3.11 (s, 3H).; ¹³C NMR (101 MHz, D6-DMSO) δ 159.85, 136.92, 131.15, 126.96, 123.99, 121.83, 121.01, 119.99, 112.41, 104.68, 45.29. ESI-MS m/z 280.2(M + H)⁺; HRMS Calcd. For $C_{17}H_{17}N_3O$ (M + H)⁺ requires 279.1372; found: 279.1375. |
| 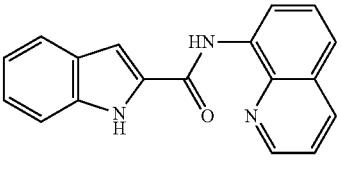 [SMILES: O=C(Nc1cccc2cccnc12)c1cc2ccccc2[nH]1]<br>L-34, yield 81% | ¹H NMR (400 MHz, D6-DMSO) δ 12.04 (s, 1H), 10.63 (s, 1H), 9.02 (dd, J = 4.2, 1.6 Hz, 1H), 8.72 (dd, J = 7.6, 1.2 Hz, 1H), 8.47 (dd, J = 8.3, 1.6 Hz, 1H), 7.77-7.72 (m, 2H), 7.72-7.64 (m, 2H), 7.51 (dd, J = 8.3, 0.6 Hz, 1H), 7.34 (d, J = 1.6 Hz, 1H), 7.30-7.23 (m, 1H), 7.15-7.08 (m, 1H).; ¹³C NMR (101 MHz, D6-DMSO) δ 159.19, 149.23, 138.07, 137.24, 136.80, 133.93, 131.25, 127.90, 127.13, 127.10, 124.17, 122.43, 122.19, 121.95, 120.21, 116.56, 112.54, 103.35. ESI-MS m/z 288.3(M + H)⁺; HRMS Calcd. For $C_{18}H_{14}N_3O$ (M + H)⁺ requires 288.1131.; found: 288.1135. |

| Structure of the ligand | Structure characterization |
|---|---|
| L-35, yield 90% | $^1$H NMR (400 MHz, D6-DMSO) δ 11.78 (s, 1H), 10.31 (s, 1H), 8.00-7.82 (m, 3H), 7.70 (d, J = 8.0 Hz, 1H), 7.57-7.41 (m, 5H), 7.23 (t, J = 7.6 Hz, 1H), 7.09 (t, J = 7.5 Hz, 1H), 2.40 (s, 3H). $^{13}$C NMR (101 MHz, D6-DMSO) δ 160.33, 136.72, 133.24, 132.32, 131.25, 130.97, 130.90, 128.72, 127.86, 127.15, 126.85, 126.31, 125.25, 123.61, 123.06, 121.65, 119.89, 112.39, 103.61, 18.29. ESI-MS m/z 301.3(M + H)$^+$; HRMS Calcd. For C$_{20}$H$_{17}$N$_2$O (M + H)$^+$ requires 301.1335.; found: 301.1339. |
| L-36, yield 94% | $^1$H NMR (400 MHz, D6-DMSO) δ 11.74 (s, 1H), 9.81 (s, 1H), 7.66 (d, J = 8.0 Hz, 1H), 7.46 (d, J = 8.2 Hz, 1H), 7.37 (d, J = 1.4 Hz, 1H), 7.21 (dd, J = 11.3, 4.0 Hz, 1H), 7.07 (t, J = 7.4 Hz, 1H), 7.01 (d, J = 9.4 Hz, 2H), 2.22 (s, 6H).; $^{13}$C NMR (101 MHz, D6-DMSO) δ 161.49, 159.88, 159.09, 138.44, 138.35, 136.65, 131.14, 131.10, 127.08, 123.59, 121.59, 119.89, 114.15, 113.94, 112.36, 103.38, 18.18. ESI-MS m/z 283.2(M + H)$^+$; HRMS Calcd. For C$_{17}$H$_{16}$FN$_2$O (M + H)$^+$ requires 283.1241.; found: 283.1246. |
| L-37, yield 90% | $^1$H NMR (400 MHz, D6-DMSO) δ 11.73 (s, 1H), 9.79 (s, 1H), 7.66 (d, J = 8.0 Hz, 1H), 7.44 (d, J = 8.2 Hz, 1H), 7.36 (d, J = 1.4 Hz, 1H), 7.28-7.14 (m, 4H), 7.09-7.04 (m, 1H), 2.58 (q, J = 7.5 Hz, 4H), 1.12 (t, J = 7.6 Hz, 6H). $^{13}$C NMR (101 MHz, D6-DMSO) δ 160.51, 141.96, 136.61, 133.67, 131.36, 127.43, 127.11, 126.17, 123.53, 121.57, 119.88, 112.36, 103.16, 24.56, 14.58. ESI-MS m/z 293.3(M + H)$^+$; HRMS Calcd. For C$_{19}$H$_{21}$N$_2$O (M + H)$^+$ requires 293.1648; found: 293.1651. |
| L-38, yield 92% | $^1$H NMR (400 MHz, d6-DMSO) δ 11.70 (s, 1H), 9.78 (s, 1H), 7.86-7.74 (m, 1H), 7.36 (t, J = 7.9 Hz, 2H), 7.32-7.17 (m, 4H), 7.17-6.94 (m, 5H), 6.83 (d, J = 7.0 Hz, 1H), 2.48 (s, 3H); HRMS (ESI) calcd for C$_{22}$H$_{19}$N$_2$O$_2$ (M + H)$^+$ 343.1441, found 343.1445. |
| L-39, yield 81% | $^1$H NMR (400 MHz, d6-DMSO) δ 11.72 (s, 1H), 9.76 (s, 1H), 7.81-7.72 (m, 1H), 7.39-7.30 (m, 3H), 7.26-7.16 (m, 2H), 7.10 (dt, J = 9.0, 7.7 Hz, 2H), 7.05-6.94 (m, 4H), 6.51 (d, J = 7.6 Hz, 1H), 3.87 (s, 3H); HRMS (ESI) calcd for C$_{22}$H$_{19}$N$_2$O$_3$ (M + H)$^+$ 359.1390, found 359.1390. |
| L-40, yield 90% | $^1$H NMR (400 MHz, d6-DMSO) δ 11.60 (s, 1H), 9.74 (s, 1H), 7.83-7.75 (m, 1H), 7.39-7.29 (m, 3H), 7.26-7.19 (m, 2H), 7.16 (d, J = 1.4 Hz, 1H), 7.12-7.06 (m, 2H), 7.05-6.97 (m, 3H), 6.85 (dd, J = 8.9, 2.4 Hz, 1H), 3.75 (s, 3H); HRMS (ESI) calcd for C$_{22}$H$_{19}$N$_2$O$_3$ (M + H)$^+$ 359.1390, found 359.1390. |

| Structure of the ligand | Structure characterization |
|---|---|
| L-42, yield 90% | ¹H NMR (400 MHz, d6-DMSO) δ 11.68 (s, 1H), 9.79 (s, 1H), 7.42 (d, J = 2.1 Hz, 1H), 7.27 (d, J = 8.2 Hz, 1H), 7.14 (s, 3H), 7.10 (dd, J = 8.2, 7.1 Hz, 1H), 6.86 (d, J = 7.0 Hz, 1H), 2.52 (s, 3H), 2.22 (s, 6H); HRMS (ESI) calcd for C₁₈H₁₉N₂O (M + H)⁺ 279.1492, found 279.1491. |
| L-43, yield 86% | ¹H NMR (400 MHz, d6-DMSO) δ 11.56 (s, 1H), 9.75 (s, 1H), 7.33 (d, J = 8.8 Hz, 1H), 7.27 (d, J = 2.1 Hz, 1H), 7.14 (s, 3H), 7.12 (d, J = 2.4 Hz, 1H), 6.86 (dd, J = 8.9, 2.5 Hz, 1H), 3.77 (s, 3H), 2.21 (s, 6H); HRMS (ESI) calcd for C₁₈H₁₉N₂O₂ (M + H)⁺ 295.1441, found 295.1447. |
| L-44, yield 81% | ¹H NMR (400 MHz, d6-DMSO) δ 12.06 (s, 1H), 9.95 (s, 1H), 7.73 (dd, J = 7.4, 2.2 Hz, 1H), 7.40-7.30 (m, 3H), 7.30-7.12 (m, 4H), 7.12-7.05 (m, 1H), 7.05-6.95 (m, 3H), 6.82 (dd, J = 10.7, 7.6 Hz, 1H); HRMS (ESI) calcd for C₂₁H₁₆FN₂O₂ (M + H)⁺ 347.1190, found 347.1188. |
| L-45, yield 80% | ¹H NMR (400 MHz, d6-DMSO) δ 11.34 (s, 1H), 10.37 (s, 1H), 8.25 (td, J = 7.9, 1.0 Hz, 2H), 8.21 (d, J = 7.8 Hz, 1H), 8.13 (dd, J = 7.8, 1.0 Hz, 1H), 8.11 (s, 1H), 7.69 (t, J = 7.9 Hz, 1H), 7.56-7.27 (m, 7H); HRMS (ESI) calcd for C₂₁H₁₆N₃O₃ (M + H)⁺ 358.1186, found 358.1188. |
| L-46, yield 90% | ¹H NMR (500 MHz, d6-DMSO) δ 11.45 (s, 1H), 9.55 (s, 1H), 7.85-7.79 (m, 1H), 7.38-7.32 (m, 2H), 7.24-7.17 (m, 2H), 7.11 (dd, J = 2.2, 0.8 Hz, 1H), 7.09 (tt, J = 7.4, 1.1 Hz, 1H), 7.06 (s, 1H), 7.05-6.97 (m, 3H), 6.87 (s, 1H), 3.77 (s, 3H), 3.75 (s, 3H); HRMS (ESI) calcd for C₂₃H₂₁N₂O₄ (M + H)⁺ 389.1496, found 389.1494. |
| L-47, yield 92% | ¹H NMR (400 MHz, d6-DMSO) δ 11.55 (s, 1H), 9.64 (s, 1H), 7.83-7.78 (m, 1H), 7.48 (d, J = 8.8 Hz, 1H), 7.39-7.32 (m, 2H), 7.24-7.17 (m, 3H), 7.12-7.06 (m, 1H), 7.05-6.95 (m, 3H), 6.86 (d, J = 2.3 Hz, 1H), 6.70 (dd, J = 8.8, 2.3 Hz, 1H), 3.76 (s, 3H); HRMS (ESI) calcd for C₂₂H₁₉N₂O₃ (M + H)⁺ 359.1390, found 359.1394. |

| Structure of the ligand | Structure characterization |
| --- | --- |
| L-48, yield 90% | ¹H NMR (400 MHz, d6-DMSO) δ 12.44 (s, 1H), 10.20 (s, 1H), 8.31 (s, 1H), 7.94-7.87 (m, 2H), 7.54-7.25 (m, 10H); HRMS (ESI) calcd for $C_{21}H_{16}N_3O_3$ (M + H)⁺ 358.1186, found 358.1179. |
| L-49 | ¹H NMR (400 MHz, d6-DMSO) δ 11.60 (s, 1H), 9.74 (s, 1H), 7.84-7.73 (m, 1H), 7.41-7.28 (m, 4H), 7.26-7.18 (m, 2H), 7.15 (d, J = 2.1 Hz, 1H), 7.13-7.06 (m, 1H), 7.06-6.95 (m, 4H), 2.36 (s, 3H); HRMS (ESI) calcd for $C_{22}H_{19}N_2O_2$ (M + H)⁺ 343.1441, found 343.1445. |
| L-51, yield 95% | ¹H NMR (400 MHz, D6-DMSO) δ 11.59 (s, 1H), 9.31 (s, 1H), 7.11 (s, 3H), 7.02 (d, J = 3.5 Hz, 1H), 6.92 (d, J = 1.1 Hz, 1H), 6.15 (dd, J = 5.7, 2.4 Hz, 1H), 2.18 (s, 6H). ¹³C NMR (101 MHz, D6-DMSO) δ 159.15, 135.85, 135.18, 127.66, 126.44, 125.95, 121.77, 110.68, 108.72, 18.19.. ESI-MS m/z 215.2(M + H)⁺; HRMS Calcd. For $C_{13}H_{15}N_2O$ (M + H)⁺ requires 215.1179; found: 215.1180 |
| L-115, yield 90% | ¹H NMR (500 MHz, CDCl₃) δ 9.53 (s, 1H), 7.92 (d, J = 8.3 Hz, 1H), 7.85 (d, J = 7.7 Hz, 1H), 7.77 (d, J = 8.4 Hz, 1H), 7.55-7.38 (m, 4H), 7.00 (s, 1H), 6.88 (s, 1H), 6.36 (dd, J = 6.0, 2.7 Hz, 1H), 2.47 (s, 3H). ¹³C NMR (126 MHz, d6-DMSO) δ 160.21, 133.66, 132.75, 131.79, 131.55, 129.14, 128.23, 126.99, 126.57, 126.30, 125.58, 123.62, 122.47, 111.46, 109.29, 18.80. ESI-MS m/z 251.1 (M + H)⁺ |
| L-53, yield 92% | ¹H NMR (400 MHz, CDCl₃) δ 8.47 (s, 1H), 7.62 (s, 2H), 7.44-7.28 (m, 7H), 4.73 (d, J = 6.1 Hz, 2H); HRMS (ESI) calcd for $C_{15}H_{14}N_3O$ (M + H)⁺ 252.1131, found 252.1131. |
| L-54, yield 88% | ¹H NMR (400 MHz, CDCl₃) δ 9.77 (s, 1H), 7.91-7.84 (m, 2H), 7.75 (s, 2H), 7.51-7.40 (m, 4H), 7.29-7.24 (m, 1H); HRMS (ESI) calcd for $C_{14}H_{12}N_3O$ (M + H)⁺ 238.0975, found 238.0975. |
| L-55, yield 85% | ¹H NMR (400 MHz, CDCl₃) δ 7.98 (s, 1H), 7.72-7.64 (m, 2H), 7.40-7.32 (m, 2H), 3.12 (d, J = 5.1 Hz, 3H); HRMS (ESI) calcd for $C_9H_{10}N_3O$ (M + H)⁺ 176.0818, found 176.0817. |

| Structure of the ligand | Structure characterization |
|---|---|
| L-56, yield 90% | $^1$H NMR (400 MHz, CDCl$_3$) δ 9.21 (s, 1H), 7.64 (s, 2H), 7.41-7.35 (m, 2H), 7.25-7.12 (m, 3H), 2.30 (s, 6H); HRMS (ESI) calcd for C$_{16}$H$_{16}$N$_3$O (M + H)$^+$ 266.1288, found 266.1290. |
| L-57, yield 94% | $^1$H NMR (400 MHz, d6-DMSO) δ 13.42 (s, 1H), 10.12 (s, 1H), 7.98 (dd, J = 8.0, 1.2 Hz, 1H), 7.66 (d, J = 7.8 Hz, 1H), 7.54-7.43 (m, 6H), 7.42-7.23 (m, 5H); $^{13}$C NMR (100 MHz, d6-DMSO) δ 157.1, 145.2, 142.3, 138.3, 135.4, 134.7, 134.0, 130.4, 128.9, 128.7, 128.1, 127.6, 125.9, 124.4, 124.4, 122.8, 120.0, 112.6; HRMS (ESI) calcd for C$_{20}$H$_{16}$N$_3$O (M + H)$^+$ 314.1288, found 314.1286. |
| L-58, yield 85% | $^1$H NMR (400 MHz, CDCl$_3$) δ 11.31 (br s, 1H), 9.21 (s, 1H), 7.76-7.66 (m, 2H), 7.42-7.33 (m, 2H), 7.23 (s, 2H), 7.19-7.14 (m, 1H); HRMS (ESI) calcd for C$_{10}$H$_{10}$N$_3$O (M + H)$^+$ 188.0818, found 188.0817. |
| L-112, yield 90% | $^1$H NMR (500 MHz, d6-DMSO) δ 9.63 (s, 1H), 8.44 (s, 1H), 8.08 (d, J = 8.0 Hz, 1H), 7.51-7.37 (m, 6H), 7.31 (m, J = 14.8, 7.4 Hz, 2H). $^{13}$C NMR (126 MHz, d6-DMSO) δ 157.23, 147.30, 138.48, 134.83, 134.70, 130.74, 129.37, 129.25, 129.18, 128.56, 128.17, 125.77, 123.71. |

Example 2 Ligand Types 5-8, Prepared by Active Acid Anhydride Method

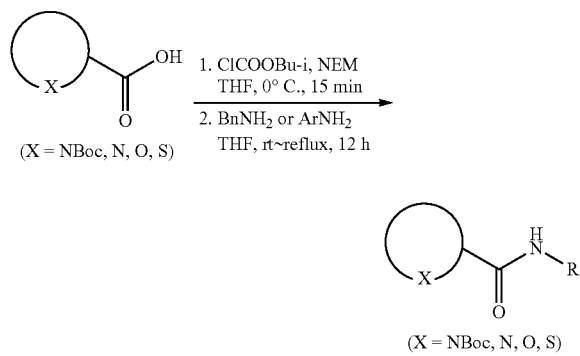

Heterocyclic-2-carboxylic acid (1.0 eq.) was dissolved in THF (0.2 M), N-ethylmorpholine (NEM, 2.5 eq.) was added, and isobutyl chloroformate (1.0 eq.) was added dropwise under ice-water bath. After the addition was completed, the system was stirred for 15 minutes in an ice water bath, and the corresponding amine (1.2 eq.) was slowly added to the system. After the addition, the ice water bath was removed, and the mixture was warmed at room temperature and stirred overnight (part of weak nucleophilic and poorly reactive amines need to be heated to reflux). The obtained suspension was concentrated under reduced pressure, and then water was added. Ethyl acetate was added for extraction, and the organic phases were combined, washed with saturated brine, dried over anhydrous sodium sulfate, and then vacuum concentrated and purified by silica gel chromatography to provide the amide of the corresponding heterocyclic-2-carboxylic acid, wherein R' in the above formula corresponds to R$_2$ of the formula I of the present invention. (Note: The Boc protecting groups on N in part of ligands need to be further removed, and the methods for removing the protecting groups are conventional Boc group deprotecting methods in the art, such as TFA deprotecting method)

| Structure of the ligand | Structure characterization |
|---|---|
| L-63, yield 90% | ¹H NMR (400 MHz, Chloroform-d) δ 9.94 (s, 1H), 8.76 (s, 1H), 8.64 (dd, J = 8.1, 1.5 Hz, 1H), 8.27 (d, J = 2.1 Hz, 1H), 7.48-7.32 (m, 2H), 7.20-7.08 (m, 4H), 7.05 (td, J = 7.8, 1.5 Hz, 1H), 6.89 (dd, J = 8.1, 1.5 Hz, 1H) |
| L-70, yield 85% | ¹H NMR (500 MHz, d6-DMSO) δ 10.61 (s, 1H), 8.23 (dd, J = 28.2, 8.0 Hz, 2H), 7.64 (m, J = 26.0, 7.6 Hz, 2H), 7.19-7.09 (m, 3H), 2.20 (s, 6H). ¹³C NMR (126 MHz, d6-DMSO) δ 158.61, 153.23, 135.99, 128.24, 128.16, 127.66, 127.50, 124.55, 123.53, 18.52. |
| L-71, yield 82% | ¹H NMR (400 MHz, Chloroform-d) δ 10.32 (s, 1H), 8.65 (dd, J = 8.3, 1.2 Hz, 1H), 8.37 (ddd, J = 4.7, 1.7, 0.9 Hz, 1H), 8.26 (dt, J = 7.8, 1.1 Hz, 1H), 7.85 (td, J = 7.7, 1.7 Hz, 1H), 7.54-7.41 (m, 6H), 7.37 (ddd, J = 7.5, 4.7, 1.2 Hz, 1H), 7.34 (dd, J = 7.6, 1.7 Hz, 1H), 7.22 (td, J = 7.5, 1.2 Hz, 1H). |
| L-73, yield 81% | ¹H NMR (400 MHz, Chloroform-d) δ 9.48 (s, 1H), 8.64 (dt, J = 4.8, 1.2 Hz, 1H), 8.30 (dt, J = 7.7, 1.2 Hz, 1H), 7.91 (td, J = 7.7, 1.8 Hz, 1H), 7.50 (ddd, J = 7.7, 4.8, 1.3 Hz, 1H), 7.19-7.06 (m, 3H), 2.30 (s, 6H). |
| L-77, yield 90% | ¹H NMR (500 MHz, CDCl₃) δ 7.58-7.53 (m, 1H), 7.49-7.43 (m, 1H), 7.39-7.23 (m, 5H), 7.04 (dq, J = 8.0, 3.9 Hz, 1H), 6.74 (m, 1H), 4.57 (dd, J = 8.1, 3.7 Hz, 2H). ¹³C NMR (126 MHz, CDCl₃) δ 161.92, 138.91, 138.16, 130.07, 128.70, 128.24, 127.84, 127.66, 127.52, 43.91. |
| L-78, yield 86% | ¹H NMR (500 MHz, CDCl₃) δ 7.69 (d, J = 3.1 Hz, 1H), 7.55 (d, J = 4.8 Hz, 1H), 7.29 (s, 1H), 7.13 (dd, J = 13.6, 5.8 Hz, 5H), 2.29 (s, 7H). |
| L-79, yield 82% | ¹H NMR (500 MHz, CDCl₃) δ 8.55 (d, J = 8.1 Hz, 1H), 8.36 (s, 1H), 7.52 (d, J = 5.0 Hz, 1H), 7.49 (d, J = 3.7 Hz, 1H), 7.39 (t, J = 7.7 Hz, 2H), 7.17 (dd, J = 13.4, 7.2 Hz, 2H), 7.11-7.03 (m, 4H), 6.91 (d, J = 8.1 Hz, 1H). |

| Structure of the ligand | Structure characterization |
|---|---|
| L-80, yield 90% | ¹H NMR (500 MHz, CDCl₃) δ 8.50 (d, J = 8.2 Hz, 1H), 7.88 (s, 1H), 7.54 (t, J = 7.6 Hz, 2H), 7.50-7.39 (m, 5H), 7.31 (d, J = 7.5 Hz, 1H), 7.22 (t, J = 7.5 Hz, 1H), 7.17 (d, J = 3.7 Hz, 1H), 7.02 (t, J = 4.3 Hz, 1H). |
| L-83, yield 95% | ¹H NMR (500 MHz, CDCl₃) δ 9.03 (s, 1H), 8.64 (dd, J = 8.1, 1.2 Hz, 1H), 7.69 (d, J = 7.8 Hz, 1H), 7.59 (s, 1H), 7.53 (d, J = 8.3 Hz, 1H), 7.47-7.38 (m, 3H), 7.31 (t, J = 7.4 Hz, 1H), 7.23-7.12 (m, 4H), 7.12-7.05 (m, 1H), 6.92 (dd, J = 8.1, 0.9 Hz, 1H). ¹³C NMR (126 MHz, CDCl₃) δ 156.55, 156.33, 154.85, 148.59, 146.19, 130.04, 129.05, 127.65, 127.17, 124.48, 124.18, 123.98, 123.83, 122.75, 120.96, 119.10, 117.55, 112.00, 111.38. |
| L-88, 83% | ¹H NMR (500 MHz, DMSO-d6) δ = 9.92 (s, 1H), 7.90 (d, J = 7.8, 1H), 7.23-7.13 (m, 2H), 7.01 (t, J = 7.4, 1H), 3.73 (dd, J = 9.1, 5.2, 1H), 3.28 (s, 1H), 2.96 (M, 1H), 2.85 (M, 1H), 2.21 (s, 3H), 2.10-1.99 (m, 1H), 1.87-1.76 (m, 1H), 1.70-1.60 (m, 2H). ¹³C NMR (125 MHz, DMSO-d6) δ 172.99, 136.19, 130.16, 127.94, 126.26, 123.82, 120.82, 60.83, 46.71, 30.39, 26.05, 17.21. MS-ESI: 205.1 (M + H⁺); HRMS (ESI) Calcd. for C₁₂H₁₇ON₂ (M + H⁺): 205.1335, Found: 205.1335. |
| L-89, 79% | ¹H NMR (500 MHz, DMSO-d6) δ = 9.39 (s, 1H), 7.05 (s, 3H), 3.73 (dd, J = 8.8, 5.4, 1H), 2.92 (t, J = 6.6, 2H), 2.12 (s, 6H), 2.08-2.01 (m, 1H), 1.87-1.78 (m, 1H), 1.74-1.65 (m, 2l1). ¹³C NMR (125 MHz, DMSO-d6) δ 172.94, 135.05, 134.88, 127.57, 126.15, 60.44, 46.81, 30.73, 25.82, 18.04. MS-ESI: 219.1 (M + H⁺); HRMS (ESI) Calcd. for C₁₃H₁₉ON₂ (M + H⁺): 219.1492, Found: 219.1491. |
| L-90, 82% | ¹H NMR (500 MHz, DMSO-d6) δ = 10.03 (s, 1H), 7.94 (dd, J = 8.0, 0.9, 1H), 7.23-7.13 (m, 2H), 7.04 (dt, J = 7.5, 1.2, 1H), 3.74 (dd, J = 9.1, 5.1, 1H), 3.01-2.93 (m, 1H), 2.87-2.80 (m, 1H), 2.58 (q, J = 7.5, 2H), 2.10-1.99 (m, 1H), 1.86-1.76 (m, 1H), 1.70-1.61 (m, 2H), 1.16 (t, J = 7.6, 3H). ¹³C NMR (125 MHz, DMSO-d6) δ 173.04, 135.55, 133.58, 128.58, 126.29, 124.05, 121.03, 60.82, 46.74, 30.36, 26.09, 23.93, 13.88. MS-ESI: 219.1 (M + H⁺); HRMS (ESI) Calcd. for C₁₃H₁₉ON₂ (M + H⁺): 219.1492, Found: 221.1490. |
| L-91, 88% | ¹H NMR (500 MHz, DMSO-d6) δ = 10.19 (s, 1H), 8.28 (d, J = 7.4, 1H), 7.05-6.99 (m, 2H), 6.92-6.88 (m, 1H), 3.85 (s, 3H), 3.73 (dd, J = 9.2, 5.3, 1H), 3.30 (s, 1H), 2.97 (dt, J = 10.2, 6.6, 1H), 2.77 (dt, J = 10.2, 6.5, 1H), 2.08-1.99 (m, 1H), 1.85-1.75 (m, 1H), 1.63 (p, J = 6.9, 2H). ¹³C NMR (125 MHz, DMSO-d6) δ 173.15, 148.06, 127.24, 123.37, 120.46, 118.34, 110.79, 60.97, 55.86, 46.70, 30.29, 26.07. MS-ESI: 221.1 (M + H⁺); HRMS (ESI) Calcd. for C₁₂H₁₇O₂N₂ (M + H⁺): 221.1285, Found: 221.1283. |
| L-96, 81% | ¹H NMR (500 MHz, DMSO-d6) δ = 10.09 (s, 1H), 8.30 (dd, J = 8.2, 1.0, 1H), 7.50 (t, J = 7.3, 2H), 7.43 (t, J = 7.4, 1H), 7.40-7.32 (m, 3H), 7.25 (dd, J = 7.6, 1.6, 1H), 7.16 (dt, J = 7.5, 1.2, 1H), 3.60 (dd, J = 9.2, 4.7, 1H), 3.01 (s, 1H), 2.77-2.68 (m, 1H), 2.48-2.42 (m, 1H), 1.99-1.89 (m, 1H), 1.78-1.70 (m, 1H), 1.59-1.43 (m, 2H). ¹³C NMR (125 MHz, DMSO-d6) δ 173.25, 137.89, 134.97, 131.96, 129.96, 129.07, 128.75, 128.04, 127.66, 123.70, 120.00, 60.55, 46.35, 30.32, 25.81. MS-ESI: 267.1 (M + H⁺); HRMS (ESI) Calcd. for C₁₇H₁₉ON₂ (M + H⁺); 267.1492, Found: 267.1490. |

| Structure of the ligand | Structure characterization |
|---|---|
| L-110, yield 93% | ¹H NMR (500 MHz, CDCl₃) δ 8.01 (s, 1H), 7.93 (d, J = 8.4 Hz, 1H), 7.85 (d, J = 7.9 Hz, 1H), 7.78 (d, J = 8.4 Hz, 1H), 7.60 (dd, J = 1.7, 0.8 Hz, 1H), 7.53-7.40 (m, 3H), 7.30 (dd, J = 3.5, 0.7 Hz, 1H), 6.62 (dd, J = 3.5, 1.8 Hz, 1H), 2.48 (s, 3H). ¹³C NMR (126 MHz, CDCl₃) δ 156.93, 147.88, 144.30, 133.67, 132.80, 130.69, 128.79, 128.17, 127.83, 126.71, 125.35, 122.18, 115.32, 112.52, 109.99, 18.80. ESI-MS m/z 252.1 (M + H)⁺ |
| L-92, yield 70% | ¹H NMR (400 MHz, Chloroform-d) δ 9.59 (s, 1H), 7.81 (d, J = 8.3 Hz, 2H), 7.70 (d, J = 8.4 Hz, 1H), 7.48 (ddd, J = 8.5, 6.8, 1.4 Hz, 1H), 7.42 (ddd, J = 7.9, 6.8, 1.3 Hz, 1H), 7.36 (d, J = 8.4 Hz, 1H), 4.06-3.98 (m, 1H), 3.18-3.07 (m, 2H), 2.39 (s, 3H), 2.34-2.24 (m, 2H), 2.24-2.12 (m, 1H), 1.98-1.76 (m, 2H); ¹³C NMR (101 MHz, Chloroform-d) δ 174.12, 132.82, 132.53, 130.41, 130.12, 128.91, 128.13, 127.01, 126.38, 125.18, 122.28, 61.01, 47.64, 31.19, 26.49, 18.80. MS-ESI: 255.1 (M + H⁺); HRMS (ESI) Calcd. for C₁₆H₁₉ON₂ (M + H⁺): 255.1492, Found: 255.1490. |
| L-101, yield 75% | ¹H NMR (400 MHz, Chloroform-d) δ 7.43 (s, 1H), 7.34-7.21 (m, 5H), 7.13-7.01 (m, 2H), 6.80 (t, J = 7.3 Hz, 1H), 6.68 (d, J = 7.8 Hz, 1H), 4.55-4.35 (m, 3H), 4.17 (s, 1H), 3.59 (dd, J = 16.3, 10.7 Hz, 1H), 3.10 (dd, J = 16.3, 8.9 Hz, 1H); ¹³C NMR (101 MHz, Chloroform-d) δ 173.84, 149.58, 138.26, 128.81, 128.14, 127.87, 127.74, 127.61, 124.91, 120.72, 111.04, 61.45, 43.16, 35.74. |
| L-102, yield 64% | ¹H NMR (400 MHz, Chloroform-d) δ 9.56 (s, 1H), 8.51 (dd, J = 8.1, 1.4 Hz, 1H), 7.34-7.27 (m, 2H), 7.18 (td, J = 7.8, 1.5 Hz, 1H), 7.14-7.04 (m, 4H), 7.01-6.93 (m, 3H), 6.85 (t, J = 7.2 Hz, 1H), 6.71 (d, J = 8.0 Hz, 1H), 4.43 (ddd, J = 10.8, 8.5, 5.9 Hz, 1H), 4.20 (d, J = 5.8 Hz, 1H), 3.59 (dd, J = 16.3, 10.8 Hz, 1H), 3.10 (dd, J = 16.3, 8.5 Hz, 1H); ¹³C NMR (101 MHz, Chloroform-d) δ 172.11, 156.71, 149.17, 145.62, 129.84, 129.53, 128.08, 127.62, 124.73, 124.45, 124.38, 123.48, 121.02, 120.78, 118.97, 117.88, 111.33, 61.89, 35.53. |
| L-104, yield 75% | ¹H NMR (500 MHz, CDCl₃) δ 9.13 (s, 1H), 6.62 (s, 2H), 4.82 (t, J = 7.7 Hz, 1H), 3.19 (m, J = 18.7, 11.5, 7.3 Hz, 2H), 2.33 (m, J = 15.3, 7.1 Hz, 1H), 2.04 (s, 3H), 1.94-1.78 (m, 8H). ¹³C NMR (126 MHz, dmso) δ 167.18, 136.55, 135.13, 131.48, 128.94, 59.82, 46.00, 30.20, 23.98, 20.94, 18.27. ESI-MS m/z 233.2 (M + H)⁺ |
| L-105, yield 60% | ¹H NMR (500 MHz, d6-DMSO) δ 9.80 (s, 1H), 7.87 (t, J = 7.9 Hz, 1H), 7.81-7.73 (m, 2H), 7.54-7.37 (m, 3H), 4.76 (s, 1H), 4.27 (d, J = 26.7 Hz, 1H), 4.02 (t, J = 8.1 Hz, 1H), 3.03 (dd, J = 11.4, 4.2 Hz, 1H), 2.86 (d, J = 11.4 Hz, 1H), 2.34-2.22 (m, 3H), 2.10 (dd, J = 13.0, 8.1 Hz, 1H), 1.92 (ddd, J = 13.0, 8.1, 5.1 Hz, 1H), 1.22 (s, 1H). ¹³C NMR (126 MHz, dmso) δ 174.22, 132.80, 132.67, 131.60, 130.89, 129.09, 128.23, 126.81, 126.56, 125.53, 123.24, 71.91, 60.20, 55.77, 40.64, 18.64. ESI-MS m/z 271.2 (M + H)⁺ |

| Structure of the ligand | Structure characterization |
|---|---|
| L-106, yield 80% | ¹H NMR (400 MHz, Chloroform-d) δ 8.85 (s, 1H), 7.83-7.66 (m, 3H), 7.47-7.39 (m, 2H), 7.31 (d, J = 8.4 Hz, 1H), 7.22-7.11 (m, 2H), 6.90 (t, J = 7.4 Hz, 1H), 6.74 (d, J = 7.8 Hz, 1H), 4.68-4.45 (m, 2H), 3.64 (dd, J = 16.3, 10.5 Hz, 1H), 3.32 (dd, J = 16.2, 8.3 Hz, 1H), 2.32 (s, 3H). ¹³C NMR (101 MHz, Chloroform-d) δ 173.01, 149.54, 132.92, 132.74, 130.34, 129.32, 128.79, 128.18, 128.15, 127.78, 127.44, 126.54, 125.28, 124.89, 122.06, 120.83, 111.35, 61.66, 35.99, 18.66. |
| L-107, yield 72% | ¹H NMR (400 MHz, Chloroform-d) δ 9.40 (s, 1H), 8.45 (d, J = 8.2 Hz, 1H), 7.42-7.34 (m, 4H), 7.31-7.23 (m, 3H), 7.21-7.15 (m, 1H), 7.12-7.02 (m, 2H), 6.87-6.80 (m, 1H), 6.51 (d, J = 7.8 Hz, 1H), 4.43-4.32 (m, 1H), 3.96 (s, 1H), 3.62 (dd, J = 16.6, 11.1 Hz, 1H), 3.19 (dd, J = 16.6, 7.2 Hz, 1H). ¹³C NMR (101 MHz, Chloroform-d) δ 172.19, 148.72, 138.11, 134.67, 132.42, 130.07, 129.37, 128.93, 128.53, 128.39, 127.77, 127.62, 124.79, 124.34, 121.10, 120.54, 111.79, 61.13, 35.79. |
| L-108, yield 71% | ¹H NMR (500 MHz, d6-DMSO) δ 9.49 (s, 1H), 7.86 (dd, J = 14.0, 7.9 Hz, 2H), 7.76 (d, J = 8.4 Hz, 1H), 7.51-7.38 (m, 4H), 3.41 (dd, 10.3, 3.0 Hz, 1H), 3.04 (d, J = 12.6 Hz, 1H), 2.68-2.58 (m, 1H), 2.33-2.25 (m, 4H), 2.02-1.92 (m, 2H), 1.87-1.79 (m, 1H), 1.67-1.33 (m, 7H). ¹³C NMR (126 MHz, dmso) δ 173.04, 133.06, 132.67, 131.64, 131.08, 129.08, 128.15, 126.89, 126.49, 125.51, 123.54, 60.44, 45.76, 30.53, 26.21, 24.50, 18.67. ESI-MS m/z 269.2 (M + H)⁺ |
| L-109, yield 90% | 1H NMR (500 MHz, CDCl3) δ 9.89 (s, 1H), 8.71 (ddd, J = 4.7, 1.6, 0.9 Hz, 1H), 8.36 (dt, J = 7.8, 1.0 Hz, 1H), 7.96 (td, J = 7.8, 1.7 Hz, 2H), 7.86 (d, J = 7.5 Hz, 1H), 7.78 (d, J = 8.4 Hz, 1H), 7.55 (ddd, J = 7.6, 4.8, 1.2 Hz, 1H), 7.51-7.42 (m, 3H), 2.50 (s, 3H). 13C NMR (126 MHz, dmso) δ 163.87, 150.45, 149.13, 138.45, 133.37, 132.72, 131.81, 131.11, 129.10, 128.24, 127.33, 127.21, 126.67, 125.59, 123.48, 122.84, 18.77. ESI-MS m/z 263.2 (M + H)+ |
| L-111, yield 92% | ¹H NMR (500 MHz, CDCl₃) δ 7.92 (d, J = 8.3 Hz, 1H), 7.85 (d, J = 7.8 Hz, 1H), 7.82-7.76 (m, 2H), 7.60 (d, J = 5.0 Hz, 2H), 7.47 (m, 3H), 7.24-7.18 (m, 1H), 2.48 (d, J = 8.6 Hz, 3H). ¹³C NMR (126 MHz, dmso) δ 160.78, 139.99, 133.66, 132.74, 131.95, 131.33, 131.23, 129.50, 129.12, 128.61, 128.32, 127.39, 126.82, 125.70, 123.40, 18.69. ESI-MS m/z 268.2 (M + H)⁺ |
| L-115, yield 90% | ¹H NMR (500 MHz, d6-DMSO) δ 9.53 (s, 1H), 7.92 (d, J = 8.3 Hz, 1H), 7.85 (d, J = 7.7 Hz, 1H), 7.77 (d, J = 8.4 Hz, 1H), 7.55-7.38 (m, 4H), 7.00 (s, 1H), 6.88 (s, 1H), 6.36 (dd, J = 6.0, 2.7 Hz, 1H), 2.47 (s, 3H). ¹³C NMR (126 MHz, d6-DMSO) δ 160.21, 133.66, 132.75, 131.79, 131.55, 129.14, 128.23, 126.99, 126.57, 126.30, 125.58, 123.62, 122.47, 111.46, 109.29, 18.80. ESI-MS m/z 251.1 (M + H)⁺ |

| Structure of the ligand | Structure characterization |
|---|---|
| (pyrrolidine-2-carboxamide with naphthalen-1-yl) yield 77% | $^1$H NMR (500 MHz, DMSO-d6) δ = 10.62 (s, 1H), 8.09-8.03 (m, 1H), 8.00-7.94 (m, 1H), 7.84 (d, J = 8.2, 1H), 7.67 (d, J = 7.2, 1H), 7.61-7.49 (m, 3H), 4.62 (t, J = 7.8, 1H), 3.37 (s, 1H), 3.35-3.26 (m, 2H), 2.58-2.50 (m, 1H), 2.13 (td, J = 14.8, 7.3, 1H), 2.00 (p, J = 7.2, 2H). $^{13}$C NMR (125 MHz, DMSO-d6) δ 168.34, 134.17, 132.76, 128.68, 128.25, 126.64, 126.63, 126.00, 122.98, 122.60, 60.08, 46.25, 30.34, 24.10. MS-ESI: 241.1 (M + H$^+$); HRMS (ESI) Calcd. for $C_{15}H_{17}ON_2$ (M + H$^+$): 241.1335, Found: 241.1335. |
| (4-hydroxypyrrolidine-2-carboxamide with naphthalen-1-yl) yield 79% | $^1$H NMR (500 MHz, DMSO-d6) δ = 10.58 (s, 1H), 8.01 (d, J = 7.4, 1H), 7.95 (d, J = 7.6, 1H), 7.89 (d, J = 8.4, 1H), 7.72 (d, J = 8.2, 1H), 7.63-7.54 (m, 2H), 7.49 (t, J = 7.9, 1H), 4.78 (s, 1H), 4.27 (s, 1H), 4.04 (t, J = 8.3, 1H), 3.00-2.88 (m, 2H), 2.11 (dd, J = 13.2, 8.4, 1H), 1.93-1.83 (m, 1H). $^{13}$C NMR (126 MHz, DMSO-d6) δ 173.43, 133.62, 132.88, 128.48, 126.23, 126.07, 125.76, 124.31, 120.80, 118.29, 71.61, 60.21, 55.04, 40.02, 39.85, 39.78, 39.69, 39.52, 39.35, 39.19, 39.02. MS-ESI: 257.1 (M + H$^+$); HRMS (ESI) Calcd. for $C_{15}H_{17}O_2N_2$ (M + H$^+$): 257.1285, Found: 257.1285. |

Example 3. Synthesis of N-benzyl-4-methylaniline by Coupling Reaction of 1-chloro-4-methylbenzene with Benzylamine

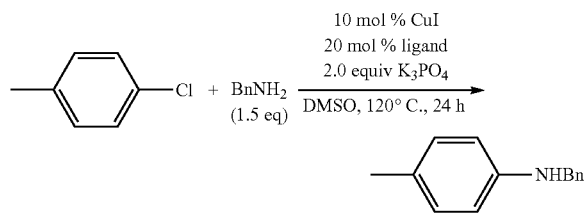

Copper (I) iodide (0.05 mmol), ligand (0.1 mmol) and potassium phosphate (1.0 mmol) were added into a 10 mL Schlenk tube. The tube was then evacuated and filled with argon for three times, and then 1-chloro-4-methylbenzene (0.5 mmol), benzylamine (0.75 mmol) and 1 mL of DMSO were added. The reaction mixture was homogeneously stirred at 120° C. for 24 hours. After cooling, water and ethyl acetate were added and the mixture was separated. The aqueous phase was extracted twice with ethyl acetate. The combined organic phase was dried over anhydrous sodium sulfate. After concentration, the residue was purified by column chromatography (petroleum ether:ethyl acetate=50:1) to give the product N-benzyl-4-methylaniline. $^1$H NMR (400 MHz, CDCl$_3$) δ 7.34-7.21 (m, 5H), 6.96 (d, J=8.0 Hz, 2H), 6.54 (d, J=8.4 Hz, 2H), 4.28 (s, 2H), 3.88 (br s, 1H), 2.22 (s, 3H); $^{13}$C NMR (100 MHz, CDCl$_3$) δ 20.6, 48.8, 113.2, 126.9, 127.3, 127.7, 128.8, 130.0, 139.8, 146.1; HRMS (ESI) calcd. for $C_{14}H_{16}N$ (M+H)$^+$: 198.1283, Found: 198.1287.

Experimental results for different heterocyclic carboxylic acid amide ligands are listed in the following table.

| No. of ligand | yield/% | No. of ligand | yield/% | No. of ligand | yield/% |
|---|---|---|---|---|---|
| L-1 | 17 | L-2 | 12 | L-3 | 21 |
| L-7 | 21 | L-32 | 23 | L-53 | 24 |

-continued

| No. of ligand | yield/% | No. of ligand | yield/% | No. of ligand | yield/% |
|---|---|---|---|---|---|
| L-54 | 10 | L-55 | 5 | L-96 | 9 |
| L-103 | 31 | L-102 | 26 | L-106 | 34 |
| L-107 | 29 | | | | |

Example 4. Synthesis of the Corresponding Aniline Derivatives by the Coupling Reaction of 1-chloro-4-methylbenzene with Various Primary and Secondary Amines

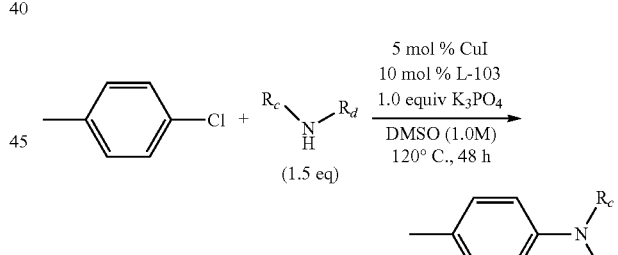

Copper iodide (0.05 mmol), ligand L-103 (0.05 or 0.1 mmol), potassium phosphate (1.0 mmol) were added into a 10 mL Schlenk tube. The tube was then evacuated and filled with argon for three times, and then 1-chloro-4-methylbenzene (1.0 mmol), amine (1.5 mmol) and 1 mL of DMSO were added. The reaction mixture was homogeneously stirred at 120° C. for 24 or 48 hours. After cooling, water and ethyl acetate were added and separated. The aqueous phase was extracted twice with ethyl acetate. The combined organic phase was dried over anhydrous sodium sulfate. After concentration, the residue was purified by column chromatography to give the product N-p-methylphenyl amine.

Different amines were used in this example, and the obtained results are shown in the table below.

| Product and yield | Characterization data of products |
|---|---|
| 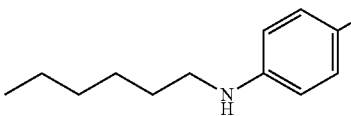<br>35% | ¹H NMR (500 MHz, CDCl₃) δ 7.07 (d, J = 8.1 Hz, 2H), 6.61 (d, J = 8.4 Hz, 2H), 3.42 (br s, 1H), 3.16 (t, J = 7.2 Hz, 2H), 2.33 (s, 3H), 1.68 (p, J = 7.2 Hz, 2H), 1.53-1.34 (m, 6H), 1.00 (t, J = 6.8 Hz, 3H); ¹³C NMR (125 MHz, CDCl₃) δ 146.25, 129.60, 126.11, 112.81, 44.31, 31.62, 29.54, 26.82, 22.58, 20.28, 13.98; LC-MS (ESI, m/z): 192.1 (M + H)⁺. |
| 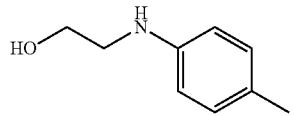<br>25% | ¹H NMR (400 MHz, CDCl₃) δ 7.00 (d, J = 7.9 Hz, 1H), 6.60 (d, J = 8.4 Hz, 2H), 3.83 (t, J = 5 Hz, 2H), 3.29 (t, J= 5 Hz, 2H), 2.25 (s, 3H); ¹³C NMR (100 MHz, CDCl₃) δ 145.67, 129.68, 127.15, 113.46, 61.02, 46.42, 20.30; LC-MS (ESI, m/z): 152.1 (M + H)⁺. |
| 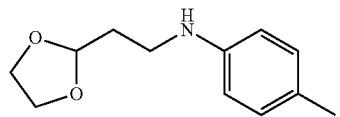<br>30% | ¹H NMR (400 MHz, CDCl₃) δ 6.99 (d, J = 8.0 Hz, 2H), 6.56 (d, J = 8.0 Hz, 2H), 4.99 (t, J = 4.5 Hz, 1H), 4.06-3.95 (m, 2H), 3.92-3.80 (m, 2H), 3.25 (t, J = 6.5 Hz, 2H), 2.23 (s, 3H), 2.01 (td, J = 6.5, 4.5 Hz, 2H); ¹³C NMR (100 MHz, CDCl₃) δ 146.00, 129.55, 126.27, 112.90, 103.59, 64.77, 39.45, 32.92, 20.26; HRMS (DART) calcd. for C₁₂H₁₈NO₂ (M + H)⁺: 208.1332, Found: 208.1333. |
| 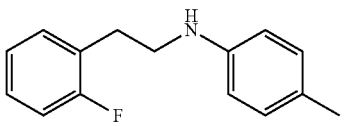<br>40% | ¹H NMR (400 MHz, CDCl₃) δ 7.27-7.17 (m, 2H), 7.13-7.00 (m, 2H), 7.00 (d, J = 8.1 Hz, 2H), 6.57 (d, J = 8.4 Hz, 2H), 3.60 (br s, 1H), 3.39 (t, J = 7.1 Hz, 2H), 2.95 (td, J = 7.1, 1.1 Hz, 2H), 2.25 (s, 3H); ¹³C NMR (100 MHz, CDCl₃) δ 161.18 (d, J = 244.8 Hz), 145.50, 130.94 (d, J = 5.0 Hz), 129.66, 127.98 (d, J = 8.1 Hz), 126.41, 126.24 (d, J = 16.0 Hz), 123.96 (d, J = 3.6 Hz), 115.21 (d, J = 22.2 Hz), 112.96, 44.04, 28.99 (d, J = 1.8 Hz), 20.26; HRMS (DART) calcd. for C₁₅H₁₇NF (M + H)⁺: 230.1340, Found: 230.1340. |
| 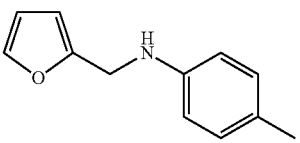<br>38% | ¹H NMR (400 MHz, CDCl₃) δ 7.36 (dd, J = 1.9, 0.9 Hz, 1H), 7.00 (d, J = 7.8 Hz, 2H), 6.61 (d, J = 8.4 Hz, 2H), 6.32 (dd, J = 3.2, 1.8 Hz, 1H), 6.23 (dd, J = 3.2, 0.9 Hz, 1H), 4.30 (s, 2H), 3.89 (br s, 1H), 2.25 (s, 3H); ¹³C NMR (100 MHz, CDCl₃) δ 152.89, 145.26, 141.70, 129.60, 127.08, 113.24, 110.21, 106.77, 41.63, 20.31; LC-MS (ESI, m/z): 188.1 (M + H)⁺. |
| 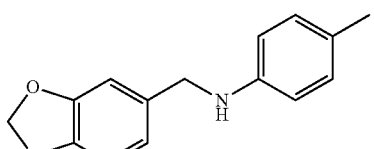<br>36% | ¹H NMR (400 MHz, CDCl₃) δ 6.99 (d, J = 8.3 Hz, 2H), 6.90-6.74 (m, 3H), 6.56 (d, J = 8.3 Hz, 2H), 5.95 (s, 2H), 4.22 (s, 2H), 3.86 (br s, 1H), 2.25 (s, 3H); ¹³C NMR (100 MHz, CDCl₃) δ 147.78, 146.57, 145.74, 133.52, 129.66, 126.68, 120.46, 112.94, 108.18, 107.96, 100.88, 48.34, 20.32; HRMS (DART) calcd. for C₁₅H₁₆NO₂ (M + H)⁺: 242.1176, Found: 242.1175. |

Example 5. Synthesis of (4-aminophenyl)methanol

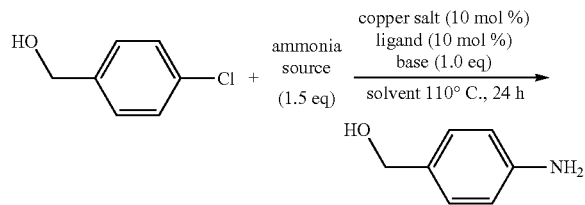

Chlorobenzyl alcohol (0.5 mmol), ammonia source (0.75 mmol), copper salt catalyst (0.05 mmol), ligand (0.05 mmol) and base (0.5 mmol) were added into a 10 mL Schlenk tube. The tube was then evacuated and filled with argon for three times, and then 0.5 mL of solvent was added. The reaction mixture was homogeneously stirred at 110° C. for 24 hours. After cooling, the mixture was filtered through silica gel and diatomite plug. The filtrate was concentrated and purified by column chromatography to give the product (4-aminophenyl) methanol (light yellow solid).

¹H NMR (400 MHz, CDCl₃) δ 7.11 (d, J=8.3 Hz, 2H), 6.62 (d, J=8.3 Hz, 2H), 4.49 (s, 2H), 3.22 (br s, 2H); ¹³C NMR (100 MHz, CDCl₃) δ 145.9, 131.0, 128.7, 115.1, 65.1; LC-MS (ESI, m/z): 124.1 (M+H)⁺.

Different ammonia sources, copper salt catalysts, ligands, bases and solvents were used in the example, and the obtained results are listed in the following table.

| No. | ammonia source | copper salt catalyst | ligand | base | solvent | yield/% |
|---|---|---|---|---|---|---|
| 1 | NH$_3$•H$_2$O | CuI | L-1 | K$_3$PO$_4$ | DMSO | 27 |
| 2 | NH$_3$•H$_2$O | CuI | L-2 | K$_3$PO$_4$ | DMSO | 42 |
| 3 | NH$_3$•H$_2$O | CuI | L-3 | K$_3$PO$_4$ | DMSO | 44 |
| 4 | NH$_3$•H$_2$O | CuI | L-4 | K$_3$PO$_4$ | DMSO | 35 |
| 5 | NH$_3$•H$_2$O | CuI | L-5 | K$_3$PO$_4$ | DMSO | 35 |
| 6 | NH$_3$•H$_2$O | CuI | L-6 | K$_3$PO$_4$ | DMSO | 64 |
| 7 | NH$_3$•H$_2$O | CuI | L-7 | K$_3$PO$_4$ | DMSO | 66 |
| 8 | NH$_3$•H$_2$O | CuI | L-8 | K$_3$PO$_4$ | DMSO | 39 |
| 9 | NH$_3$•H$_2$O | CuI | L-9 | K$_3$PO$_4$ | DMSO | 38 |
| 10 | NH$_3$•H$_2$O | CuI | L-11 | K$_3$PO$_4$ | DMSO | 34 |
| 11 | NH$_3$•H$_2$O | CuI | L-12 | K$_3$PO$_4$ | DMSO | 78 |
| 12 | NH$_3$•H$_2$O | CuI | L-13 | K$_3$PO$_4$ | DMSO | 84 |
| 13 | NH$_3$•H$_2$O | CuI | L-14 | K$_3$PO$_4$ | DMSO | 77 |
| 14 | NH$_3$•H$_2$O | CuI | L-15 | K$_3$PO$_4$ | DMSO | 89 |
| 15 | NH$_3$•H$_2$O | CuI | L-20 | K$_3$PO$_4$ | DMSO | 46 |
| 16 | NH$_3$•H$_2$O | CuI | L-25 | K$_3$PO$_4$ | DMSO | 67 |
| 17 | NH$_3$•H$_2$O | CuI | L-26 | K$_3$PO$_4$ | DMSO | 49 |
| 18 | NH$_3$•H$_2$O | CuI | L-28 | K$_3$PO$_4$ | DMSO | 71 |
| 19 | NH$_3$•H$_2$O | CuI | L-29 | K$_3$PO$_4$ | DMSO | 60 |
| 20 | NH$_3$•H$_2$O | CuI | L-30 | K$_3$PO$_4$ | DMSO | 45 |
| 21 | NH$_3$•H$_2$O | CuI | L-31 | K$_3$PO$_4$ | DMSO | 91 |
| 22 | NH$_3$•H$_2$O | CuI | L-32 | K$_3$PO$_4$ | DMSO | 78 |
| 23 | NH$_3$•H$_2$O | CuI | L-33 | K$_3$PO$_4$ | DMSO | 21 |
| 24 | NH$_3$•H$_2$O | CuI | L-38 | K$_3$PO$_4$ | DMSO | 55 |
| 25 | NH$_3$•H$_2$O | CuI | L-39 | K$_3$PO$_4$ | DMSO | 57 |
| 26 | NH$_3$•H$_2$O | CuI | L-42 | K$_3$PO$_4$ | DMSO | 69 |
| 27 | NH$_3$•H$_2$O | CuI | L-44 | K$_3$PO$_4$ | DMSO | 34 |
| 28 | NH$_3$•H$_2$O | CuI | L-46 | K$_3$PO$_4$ | DMSO | 41 |
| 29 | NH$_3$•H$_2$O | CuI | L-47 | K$_3$PO$_4$ | DMSO | 43 |
| 30 | NH$_3$•H$_2$O | CuI | L-48 | K$_3$PO$_4$ | DMSO | 25 |
| 31 | NH$_3$•H$_2$O | CuI | L-49 | K$_3$PO$_4$ | DMSO | 60 |
| 32 | NH$_3$•H$_2$O | CuI | L-51 | K$_3$PO$_4$ | DMSO | 24 |
| 33 | NH$_3$•H$_2$O | CuI | L-54 | K$_3$PO$_4$ | DMSO | 14 |
| 34 | NH$_3$•H$_2$O | CuI | L-96 | K$_2$CO$_3$ | DMSO | 10 |
| 35 | NH$_3$•H$_2$O | Cu$_2$O | L-15 | K$_3$PO$_4$ | DMSO | 52 |
| 36 | NH$_3$•H$_2$O | CuTc | L-15 | K$_3$PO$_4$ | DMSO | 80 |
| 37 | NH$_3$•H$_2$O | CuI | L-15 | K$_3$PO$_4$ | DMSO | 60 |
| 38 | NH$_3$•H$_2$O | CuI | L-15 | K$_3$PO$_4$ | DMSO | 57 |
| 39 | NH$_3$•H$_2$O | CuI | L-43 | K$_3$PO$_4$ | DMSO | 67 |
| 40 | NH$_3$•H$_2$O | CuI | L-45 | K$_3$PO$_4$ | DMSO | 14 |
| 41 | NH$_4$Cl + KOH | CuI | L-15 | K$_3$PO$_4$ | DMSO | 60 |
| 42 | NH$_3$ (gas, 5 atm) | CuI | L-15 | K$_3$PO$_4$ | DMSO | 79 |
| 43 | NaN$_3$ | CuI | L-15 | K$_3$PO$_4$ | DMSO | 46 |
| 44 | (NH$_4$)$_2$CO$_3$ + KOH | CuI | L-15 | K$_3$PO$_4$ | DMSO | 39 |
| 45 | (NH$_4$)$_2$SO$_4$ + KOH | CuI | L-15 | K$_3$PO$_4$ | DMSO | 55 |
| 46 | (NH$_4$)$_2$HPO$_4$ + KOH | CuI | L-15 | K$_3$PO$_4$ | DMSO | 72 |

Example 6. Synthesis of Aromatic Amines

Copper iodide (0.05 mmol), ligand L-15 (0.05 or 0.1 mmol), potassium phosphate (1.1 mmol) were added into a 10 mL Schlenk tube. The tube was then evacuated and filled with argon for three times, and then aryl chloride (1.0 mmol), 1 mL of DMSO and ammonium hydroxide (2.0 mmol) were added. The reaction mixture was homogeneously stirred at 110° C. or 120° C. for 24 hours. After cooling, water and ethyl acetate were added and separated. The aqueous phase was extracted twice with ethyl acetate. The combined organic phase was dried over anhydrous sodium sulfate. After concentration, the residue was purified by column chromatography to give the product aromatic amines.

Different aryl chlorides were used in the example, and the obtained results are listed in the following table.

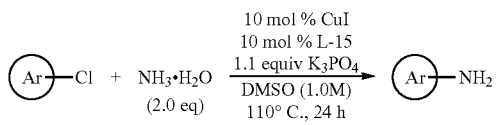

| Product and yield | Characterization data of products |
|---|---|
| $^t$BuO—C$_6$H$_4$—NH$_2$  75% | $^1$H NMR (400 MHz, CDCl$_3$) δ 6.84-6.75 (m, 2H), 6.63-6.55 (m, 2H), 3.51 (s, 2H), 1.28 (s, 9H); $^{13}$C NMR (100 MHz, CDCl$_3$) δ 147.05, 142.38, 125.34, 115.39, 77.71, 28.68.; LC-MS (ESI, m/z): 166.2 (M + H)$^+$. |
| H$_2$N-(3-methylbenzothiophen-5-yl)  89% | $^1$H NMR (400 MHz, CDCl$_3$) δ 7.50 (dd, J = 8.5, 0.6 Hz, 1H), 6.92 (t, J = 1.3 Hz, 1H), 6.89 (dd, J = 2.3, 0.6 Hz, 1H), 6.69 (dd, J = 8.5, 2.3 Hz, 1H), 3.60 (br, 1H), 2.26 (d, J = 1.3 Hz, 3H).; $^{13}$C NMR (100 MHz, CDCl$_3$) δ 143.35, 140.78, 131.17, 130.53, 123.10, 122.19, 114.54, 106.62, 13.80; HRMS (ESI) calcd. for C$_9$H$_{10}$NS (M + H)$^+$: 164.0528. Found; 164.0532. |
| 3,5-dimethoxyaniline  85% | $^1$H NMR (400 MHz, CDCl$_3$) δ 5.93 (t, J = 2.1 Hz, 1H), 5.87 (d, J = 2.1 Hz, 2H), 3.74 (s, 6H); $^{13}$C NMR (100 MHz, CDCl$_3$) δ 161.59, 148.53, 93.63, 90.77, 55.02; LC-MS (ESI, m/z): 154.1 (M + H)$^+$. |

-continued

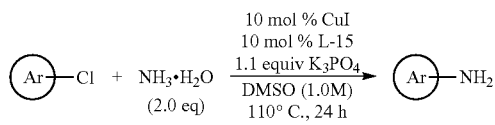

| Product and yield | Characterization data of products |
|---|---|
| 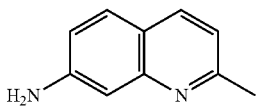 98% | $^1$H NMR (400 MHz, CDCl$_3$) δ 7.87 (d, J = 8.3 Hz, 1H), 7.56 (d, J = 8.6 Hz, 1H), 7.15 (d, J = 2.3 Hz, 1H), 7.02 (d, J = 8.2 Hz, 1H), 6.91 (dd, J = 8.6, 2.3 Hz, 1H), 4.04 (br s, 2H), 2.67 (s, 3H); $^{13}$C NMR (100 MHz, CDCl$_3$) δ 158.95, 149.34, 148.01, 135.91, 128.53, 120.22, 118.34, 117.62, 108.34, 25.04; HRMS (ESI) calcd, for C$_{10}$H$_{11}$N$_2$ (M + H)$^+$: 159.0917. Found: 159.0919. |
| 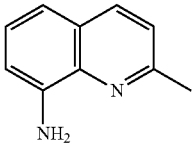 83% | $^1$H NMR (500 MHz, CDCl$_3$) δ 7.95 (d, J = 8.4 Hz, 1H), 7.29-7.21 (m, 2H), 7.11 (dd, J = 8.1, 1.3 Hz, 1H), 6.90 (dd, J = 7.5, 1.2 Hz, 1H), 4.95 (s, 2H), 2.71 (s, 3H); $^{13}$C NMR (100 MHz, CDCl$_3$) δ 156.10, 143.44, 137.85, 136.04, 126.89, 126.31, 122.11, 115.84, 110.10, 25.22; LC-MS (ESI, m/z): 159.1 (M + H)$^+$. |
| 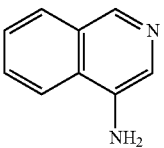 75% | $^1$H NMR (500 MHz, CDCl$_3$) δ 8.74 (s, 1H), 8.03 (s, 1H), 7.95-7.87 (m, 1H), 7.84-7.75 (m, 1H), 7.71-7.62 (m, 1H), 7.62-7.53 (m, 1H), 4.11 (s, 2H); $^{13}$C NMR (100 MHz, CDCl$_3$) δ 142.97, 137.12, 128.96, 128.63, 127.99, 127.73, 127.03, 126.05, 120.12; LC-MS (ESI, m/z): 145.1 (M + H)$^+$. |
| 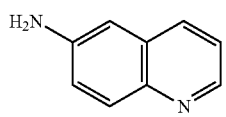 93% | $^1$H NMR (400 MHz, CDCl$_3$) δ 8.65 (dd, J = 4.2, 1.6 Hz, 1H), 7.94-7.86 (m, 2H), 7.27 (dd, J = 8.2, 4.3 Hz, 1H), 7.16 (dd, J = 8.9, 2.6 Hz, 1H), 6.90 (d, J = 2.7 Hz, 1H), 3.96 (s, 2H).; $^{13}$C NMR (100 MHz, CDCl$_3$) δ 146.50, 144.85, 143.14, 133.75, 130.19, 129.74, 121.60, 121.29. 107.20; LC-MS (ESI, m/z): 145.1 (M + H)$^+$. |
| 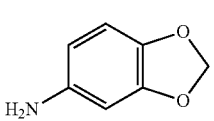 72% | $^1$H NMR (400 MHz, CDCl$_3$) δ 6.62 (d, J = 8.1 Hz, 1H), 6.29 (d, J = 2.3 Hz, 1H), 6.13 (dd, J = 8.1, 2.3 Hz, 1H), 5.86 (s, 2H), 3.45 (s, 2H); $^{13}$C NMR (100 MHz, CDCl$_3$) δ 148.18, 141.46, 140.30, 108.58, 106.89, 100.65, 98.08; LC-MS (ESI, m/z): 138.1 (M + H)$^+$. |
| 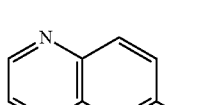 92% | $^1$H NMR (500 MHz, CDCl$_3$) δ 8.66 (d, J = 2.0 Hz, 1H), 8.55 (d, J = 1.9 Hz, 1H), 7.88 (d, J = 8.9 Hz, 1H), 7.19 (dd, J = 9.0, 2.6 Hz, 1H), 7.14 (d, J = 2.5 Hz, 1H), 4.23 (s, 2H); $^{13}$C NMR (100 MHz, CDCl$_3$) δ 148.27, 145.09, 144.97, 141.02, 138.09, 130.47, 122.23, 107.93; LC-MS (ESI, m/z): 146.1 (M + H)$^+$. |
| 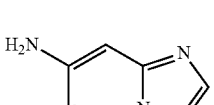 71% | $^1$H NMR (500 MHz, d6-DMSO) δ 8.17-8.10 (m, 1H), 7.50 (br s, 1H), 7.19 (d, J = 1.4 Hz, 1H), 6.42-6.36 (m, 2H), 5.65 (br s, 2H); $^{13}$C NMR (125 MHz, d6-DMSO) δ 147.05, 146.47, 131.18, 126.71, 110.36, 106.49, 92.25; LC-MS (ESI, m/z): 134.1 (M + H)$^+$. |
| 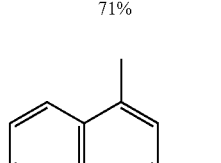 88% | $^1$H NMR (400 MHz, CDCl$_3$) δ 7.79 (dd, J = 8.3, 1.4 Hz, 1H), 7.67 (dd, J = 8.3, 1.2 Hz, 1H), 7.56 (d, J = 1.5 Hz, 0H), 7.35-7.23 (m, 1H), 6.59 (s, 1H), 4.94 (br s, 2H), 2.58 (d, J = 1.0 Hz, 3H); $^{13}$C NMR (125 MHz, CDCl$_3$) δ 155.88, 148.30, 142.39, 130.38, 123.91, 123.22, 122.70, 122.58, 112.40, 18.80; LC-MS (ESI, m/z): 159.1 (M + H)$^+$. |

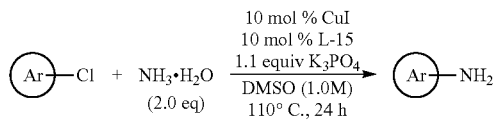

| Product and yield | Characterization data of products |
|---|---|
| 4-tert-butylaniline, 80% | ¹H NMR (400 MHz, CDCl₃) δ 7.16 (d, J = 8.0 Hz, 2 H), 6.60 (d, J = 8.0 Hz, 2 H), 3.49 (br s, 2 H), 1.27 (s, 9 H); ¹³C NMR (100 MHz, CDCl₃) δ 143.9, 141.3, 126.1, 115.0, 33.9, 31.6; LC-MS (ESI, m/z): 150.2 (M + H)⁺. |
| 2,5-dichloro-CF₃-benzene → 4-chloro-3-CF₃-aniline, 78% | ¹H NMR (400 MHz, CDCl₃) δ 7.25 (d, J = 7.1 Hz, 1H), 6.96 (d, J = 2.8 Hz, 1H), 6.73 (dd, J = 8.6, 2.7 Hz, 1H), 3.84 (br s, 2H); ¹³C NMR (125 MHz, CDCl₃) δ 145.26, 132.18, 128.81 (q, J = 31.0 Hz), 122.98 (q, J = 273.1 Hz), 120.34 (q, J = 1.9 Hz), 118.80, 113.76 (q, J = 5.6 Hz); LC-MS (ESI, m/z): 195.9 (M + H)⁺. |
| 3,5-dichloroanisole → 3-chloro-5-methoxyaniline, 78% | ¹H NMR (500 MHz, CDCl₃) δ 6.32 (t, J = 2.0 Hz, 1H), 6.28 (t, J = 1.9 Hz, 1H), 6.09 (t, J = 2.1 Hz, 1H), 3.73 (s, 3H), 3.63 (s, 2H); ¹³C NMR (125 MHz, CDCl₃) δ 161.28, 148.47, 135.41, 108.05, 104.53, 99.41, 55.39; LC-MS (ESI, m/z): 158.1 (M + H)⁺. |
| 4-(methylthio)aniline, 81% | ¹H NMR (400 MHz, CDCl₃) δ 7.18 (d, J = 8.5 Hz, 2H), 6.63 (d, J = 8.5 Hz, 2H), 3.53 (s, 2H), 2.41 (s, 3H); ¹³C NMR (125 MHz, CDCl₃) δ 145.17, 131.02, 125.65, 115.74, 18.77; LC-MS (ESI, m/z): 140.1 (M + H)⁺. |
| 4-morpholinoaniline, 80% | ¹H NMR (400 MHz, CDCl₃) δ 6.83-6.76 (m, 2H), 6.70-6.63 (m, 2H), 3.89-3.81 (m, 4H), 3.43 (s, 2H), 3.08-2.95 (m, 4H); ¹³C NMR (125 MHz, CDCl₃) δ 144.57, 140.44, 118.33, 116.36, 67.22, 51.25. |
| 4-(1H-pyrrol-1-yl)aniline, 63% | ¹H NMR (400 MHz, CDCl₃) δ 7.15-7.06 (m, 2H), 6.94-6.86 (m, 2H), 6.69-6.60 (m, 2H), 6.27-6.18 (m, 2H), 3.60 (s, 2H); ¹³C NMR (125 MHz, CDCl₃) δ 144.65, 133.04, 122.49, 119.81, 115.78, 109.56. |
| 2-chloroaniline → 1,2-phenylenediamine, 50% | ¹H NMR (400 MHz, CDCl₃) δ 6.76-6.68 (m, 4H), 3.33 (br s, 4H); ¹³C NMR (100 MHz, CDCl₃) δ 134.8, 120.3, 116.7; LC-MS (ESI, m/z): 109.2 (M + H)⁺. |
| 4-aminobenzonitrile, 88% | ¹H NMR (400 MHz, CDCl₃) δ 4.40 (br s, 2H), 6.60 (d, J = 8.8 Hz, 2H), 7.33 (d, J = 8.8 Hz, 2H); ¹³C NMR (100 MHz, CDCl₃) δ 99.7, 114.3, 120.2, 133.6, 150.5; LC-MS (ESI, m/z): 119.1 (M + H)⁺. |

Example 7. Synthesis of 1-methyl-4-phenoxybenzene

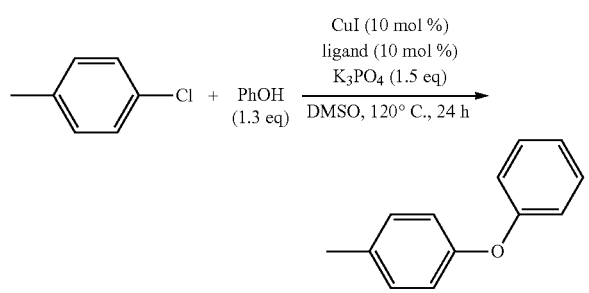

Phenol (1.5 mmol), copper iodide (0.1 mmol), ligand (0.1 mmol) and potassium phosphate (1.5 mmol) were added into a 10 mL Schlenk tube. The tube was then evacuated and filled with argon for three times, and then 1-chloro-4-methylbenzene (1.0 mmol) and 1 mL of DMSO were added. The reaction mixture was homogeneously stirred at 120° C. for 24 hours. After cooling, the contents of the of Schlenk tube were washed with ethyl acetate, and filtrated through silica gel and diatomite plug. The filtrate was concentrated and purified by column chromatography to give the product 1-methyl-4-phenoxybenzene.

$^1$H NMR (400 MHz, CDCl$_3$) δ 7.40-7.31 (m, 2H), 7.21-7.15 (m, 2H), 7.14-7.08 (m, 1H), 7.06-7.01 (m, 2H), 7.00-6.93 (m, 2H), 2.38 (s, 3H); $^{13}$C NMR (100 MHz, CDCl$_3$) δ 158.02, 154.91, 133.06, 130.45, 129.83, 122.98, 119.32, 118.53, 20.89

The results obtained by using different ligands are listed in the following table.

| No. of ligand | yield/% | No. of ligand | yield/% | No. of ligand | yield/% |
|---|---|---|---|---|---|
| L-1 | 19 | L-2 | 38 | L-3 | 30 |
| L-6 | 58 | L-7 | 45 | L-10 | 44 |
| L-13 | 68 | L-14 | 62 | L-15 | 64 |
| L-17 | 44 | L-21 | 26 | L-29 | 42 |
| L-30 | 32 | L-31 | 29 | L-32 | 22 |
| L-35 | 69 | L-37 | 59 | L-40 | 48 |
| L-57 | 37 | L-96 | 26 | L-103 | 19 |
| L-16 | 14 | L-18 | 10 | L-19 | 7 |
| L-22 | 21 | L-23 | 32 | L-24 | 11 |
| L-27 | 8 | L-34 | 17 | L-36 | 58 |
| L-50 | 11 | L-52 | 28 | L-56 | 54 |
| L-58 | 10 | L-59 | 9 | L-60 | 19 |

Example 8. Synthesis of Diaryl Ether and Aryl Alkyl Ether Via Coupling Reaction of Aryl Chloride and R$_c$OH

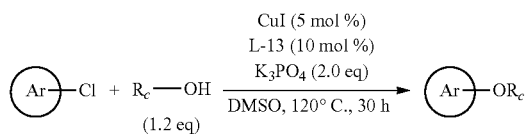

Aryl halide substrate (1.0 mmol), phenol (1.2 mmol), copper iodide (0.05 mmol), ligand L-13 (0.1 mmol), and potassium phosphate (2.0 mmol) were added into a 10 mL Schlenk tube. The tube was then evacuated and filled with argon for three times, and then 1 mL of DMSO was added. The reaction mixture was homogeneously stirred at 120° C. for 30 hours. After cooling, the contents of the of Schlenk tube were washed with ethyl acetate, and filtrated through silica gel and diatomite plug. The filtrate was concentrated and purified by column chromatography to give the product diaryl ether. The obtained results are shown in the following table.

| aryl chloride and phenol | product and yield | Characterization data of the product |
|---|---|---|
| NC—⟨⟩—Cl<br>MeO—⟨⟩—OH | MeO—⟨⟩—O—⟨⟩—CN<br>75% | $^1$H NMR (400 MHz, CDCl$_3$) δ 3.83 (s, 3H), 6.94 (m, 4H), 7.01 (m, 2H), 7.58 (m, 2H); $^{13}$C NMR (100 MHz, CDCl$_3$) δ 55.9, 105.4, 115.5, 117.3, 119.2, 122.1, 134.3, 148.1, 157.3, 162.8; GC-MS (EI, m/z): 225.1 (M$^+$). |
| CH$_3$C(O)—⟨⟩—Cl<br>MeO—⟨⟩—OH | MeO—⟨⟩—O—⟨⟩—C(O)CH$_3$<br>60% | $^1$H NMR (400 MHz, CDCl$_3$) δ 7.90 (2H, d, J = 8.8 Hz), 7.00 (2H, d, J = 9.0 Hz), 6.92-6.88 (4H, m), 3.80 (3H, s), 2.55 (3H, s); $^{13}$C NMR (100 MHz, CDCl$_3$) δ 196.6, 162.9, 156.6, 148.4, 131.3, 130.5, 121.6, 116.3, 115.0, 55.6, 26.3; GC-MS (EI, m/z): 242.1 (M$^+$). |

| aryl chloride and phenol | product and yield | Characterization data of the product |
|---|---|---|
| 2-chloronaphthalene; MeO-C6H4-OH | 2-naphthyl 4-methoxyphenyl ether, 72% | $^1$H NMR (400 MHz, CDCl$_3$) δ 7.80 (2H, d, J = 9.0 Hz), 7.66 (1H, d, J = 8.0 Hz), 7.42 (2H, m), 7.26 (1H, m), 7.18 (1H, m), 7.06 (2H, d, J = 8.9 Hz), 6.92 (2H, d, J = 9.0 Hz); $^{13}$C NMR (100 MHz, CDCl$_3$) δ 156.4, 156.0, 140.0, 134.3, 129.7, 127.6, 126.9, 126.4, 124.3, 121.0, 119.3, 114.9, 112.2, 55.6; GC-MS (EI, m/z): 250.1 (M$^+$). |
| 4-chloroacetanilide; 4-methylphenol | 4-acetamidophenyl 4-methylphenyl ether, 70% | $^1$H NMR (400 MHz, CDCl$_3$) δ 7.69 (1H, s), 7.43-7.45 (2H, d, J = 8.8), 7.13-7.14 (2H, d, J = 8.2), 6.94-6.95 (2H, d, J = 8.8), 6.89-6.91 (2H, d, J = 8.4), 2.34 (3H, s), 2.17 (3H, s); $^{13}$C NMR (100 MHz, CDCl$_3$) δ 168.8, 155.2, 154.4, 135.9, 133.3, 133.0, 130.5, 129.0, 122.1, 119.2, 118.9, 24.6, 20.9; LC-MS (ESI, m/z): 242.1 (M + H)$^+$. |
| 4-chlorobenzotrifluoride; 3-methylphenol | 4-trifluoromethylphenyl 3-methylphenyl ether, 68% | $^1$H NMR (400 MHz, CDCl$_3$) δ 7.56 (d, J = 8.6 Hz, 2H), 7.29-7.25 (m, 1H), 7.04-6.99 (m, 1H), 7.03 (d, J = 8.7 Hz, 2H), 6.87-6.84 (m, 2H), 2.36 (s, 3H); $^{13}$C NMR (100 MHz, CDCl$_3$) δ 160.7, 155.7, 140.4, 129.8, 127.0, 125.3, 124.6, 122.9, 120.6, 117.9, 117.0, 21.4; GC-MS (EI, m/z): 252.1 (M$^+$). |
| 4-chlorobenzotrifluoride; 3,5-dimethylphenol | 4-fluorophenyl 3,5-dimethylphenyl ether, 76% | $^1$H NMR (400 MHz, CDCl$_3$) δ 2.27 (3H, s), 6.58 (2H, s), 6.73 (1H, s), 6.9-7.1 (4H, m); $^{13}$C NMR (100 MHz, CDCl$_3$) δ 21.7, 116.4, 116.6 (d, J = 23 Hz), 120.9 (d, J = 8.6 Hz), 120.9, 125.3, 140.0, 153.5 (d, J = 2.6 Hz), 158.0, 1159.1 (d, J = 241 Hz); GC-MS (EI, m/z): 216.1 (M$^+$). |

Example 9. Coupling of 4-chloroanisole with Sodium Methylsulfinate

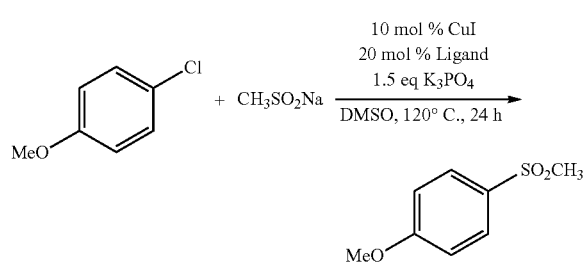

Sodium methanesulfinate (0.6 mmol), copper iodide (0.05 mmol), ligand (0.1 mmol) and potassium phosphate (1.5 mmol) were added into a 10 mL of Schlenk tube. The tube was evacuated and filled with argon for three times, and then 4-chloroanisole (0.5 mmol) and 1 mL of DMSO were added. The reaction mixture was homogeneously stirred at 120° C. for 24 hours. After cooling, the contents of the of Schlenk tube were washed with ethyl acetate, and filtered through silica gel and diatomite plug. The filtrate was concentrated and purified by column chromatography to give the product 4-methoxy phenyl methyl sulfone.

$^1$H NMR (400 MHz, CDCl$_3$) δ 3.05 (s, 3H), 3.90 (s, 3H), 7.04 (dd, J=7.5, 2.1 Hz, 2H), 7.88 (dd, J=7.5, 2.1 Hz, 2H); EI-MS (m/z) 186 (M+)

The results obtained by using different ligands are listed in the following table.

| Ligand | yield/% | Ligand | yield/% | Ligand | yield/% |
|---|---|---|---|---|---|
| L-54 | 24 | L-88 | 50 | L-89 | 52 |
| L-90 | 31 | L-91 | 26 | L-92 | 80 |
| L-95 | 45 | L-96 | 40 | L-104 | 47 |
| L-105 | 50 | L-108 | 36 | L-109 | 44 |
| L-115 | 53 | L-35 | 52 | | |

Example 10. Coupling of 4-chloroanisole with Sodium Methylsulfinate

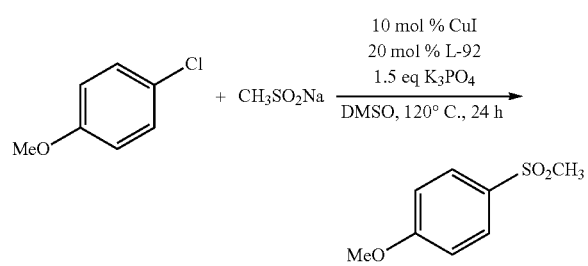

The operation of this example was the same as that of Example 9 except that different copper catalysts, bases, solvents and reaction temperatures were used. The experiment results are shown in the following table:

| No. | Copper salt | base | solvent | temperature | yield/% |
|---|---|---|---|---|---|
| 1 | CuI | Cs$_2$CO$_3$ | DMSO | 120 | 31 |
| 2 | CuI | K$_2$CO$_3$ | DMSO | 120 | 60 |
| 3 | CuI | K$_3$PO$_4$ | DMSO | 120 | 80 |
| 4 | CuBr | K$_3$PO$_4$ | DMSO | 120 | 50 |
| 5 | CuCl$_2$ | K$_3$PO$_4$ | DMSO | 120 | 18 |
| 6 | Cu$_2$O | K$_3$PO$_4$ | DMSO | 120 | 22 |
| 7 | CuCl | K$_3$PO$_4$ | DMSO | 120 | 45 |
| 8 | CuSCN | K$_3$PO$_4$ | DMSO | 120 | 35 |
| 9 | Cu$_2$S | K$_3$PO$_4$ | DMSO | 120 | 18 |
| 10 | CuI | K$_3$PO$_4$ | DMF | 120 | 65 |
| 11 | CuI | K$_3$PO$_4$ | NMP | 120 | 73 |
| 12 | CuI | K$_3$PO$_4$ | toluene | 120 | 36 |

Example 11. Coupling of Aryl Chloride with Sodium Alkylsulfinate or Sodium Arylsulfinate

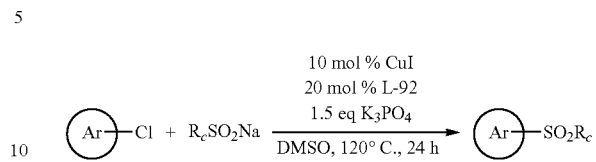

Sodium alkylsulfinate or sodium arylsulfinate (0.6 mmol), copper iodide (0.05 mmol), ligand (0.1 mmol) and potassium phosphate (1.5 mmol) were added into a 10 mL Schlenk tube. The tube was evacuated and filled with argon for three times, and then aryl chloride (0.5 mmol) and 1 mL of DMSO were added. The reaction mixture was homogeneously stirred at 120° C. for 24 hours. After cooling, the contents of the of Schlenk tube were washed with ethyl acetate, and filtered through silica gel and diatomite plug. The filtrate was concentrated and purified by column chromatography to give the corresponding product.

| Product and yield | Characterization data of products |
|---|---|
| MeO–C$_6$H$_4$–SO$_2$Ph  50% | $^1$H NMR (400 MHz, CDCl$_3$) δ 3.84 (s, 3H), 6.96 (m, 2H), 7.51 (m, 3H), 7.90 (m, 4H); EI-MS (m/z) 248 (M$^+$) |
| Ph–C$_6$H$_4$–SO$_2$CH$_3$  92% | $^1$H NMR (400 MHz, CDCl$_3$) δ 7.99 (d, J = 8.4 Hz, 2H), 7.76 (d, J = 8.5 Hz, 2H), 7.60 (d, J = 7.0 Hz, 2H), 7.48 (t, J = 7.3 Hz, 2H), 7.42 (t, J = 7.2 Hz, 1H), 3.08 (s, 3H) |
| AcHN–C$_6$H$_4$–SO$_2$CH$_3$  80% | $^1$H NMR (500 MHz, CDCl$_3$) δ 7.94-7.85 (m, 2H), 7.71 (t, J = 8.9 Hz, 2H), 7.46 (d, J = 8.9 Hz, 1H), 3.04 (s, 3H), 2.23 (s, 3H) |

Example 12. Synthesis of Aromatic Amines by Reaction of Aryl Bromides/Iodides and Amines Aryl bromide/iodide substrates (1.0 mmol), amine (1.2 mmol), copper iodide (0.05 mmol), ligand (0.05 mmol) and potassium phosphate (1.0 mmol) were added into a 10 mL of Schlenk tube. The tube was then evacuated and filled with argon for three times, and then 1 mL of DMSO was added. The reaction mixture was homogeneously stirred at 80° C. for 48 hours. After cooling, the contents of the of Schlenk tube were washed with ethyl acetate, and filtrated through silica gel and diatomite plug. The filtrate was concentrated and purified by column chromatography to give the product aromatic amines. The obtained results are shown in the following table.

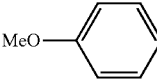
| aryl halide | ligand | yield | ligand | yield |
| --- | --- | --- | --- | --- |
| 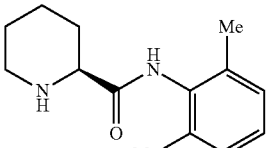 | 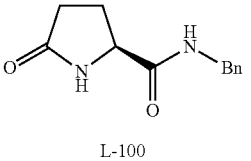 [SMILES: O=C1CC[C@@H](C(=O)NCc2ccccc2)N1] L-98 | 61% | 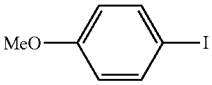 L-100 | 20% |
| | 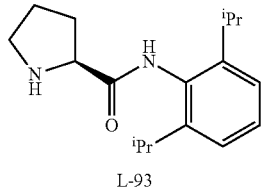 [SMILES: CC(C)c1cccc(C(C)C)c1NC(=O)[C@@H]1CCCN1] L-93 | 16% | 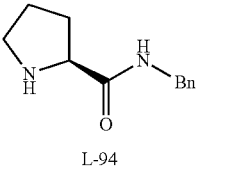 [SMILES: O=C(NCc1ccccc1)[C@@H]1CCCN1] L-94 | 37% |
| 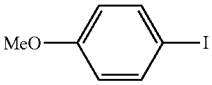 | 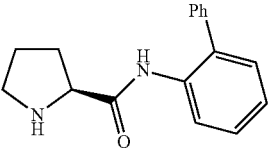 L-96 | 75% | 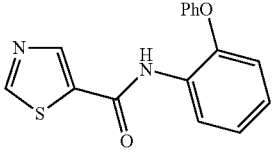 L-67 | 10% |
| | 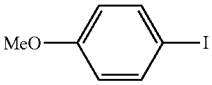 L-71 | 48% | 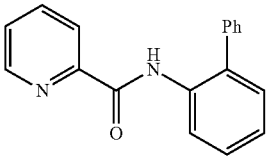 L-97 | 54% |
| | 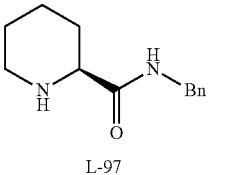 [SMILES: O=C(NCc1ccccc1)[C@@H]1CCCCN1] L-99 | 74% | 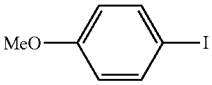 L-101 | 43% |
| | 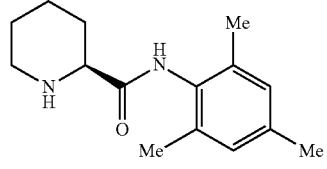 L-72 | 51% |  L-73 | 58% |

Example 13. Synthesis of Arylsulfide by Reaction of 4-methyl iodobenzene and 4-methoxy thiophenol

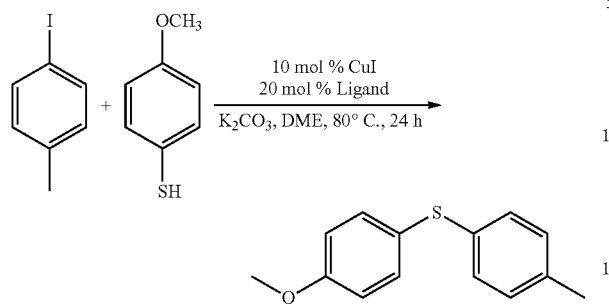

Copper iodide (0.1 mmol), ligand (0.1 mmol) and potassium phosphate (1.5 mmol) were added into a 10 mL Schlenk tube. The tube was then evacuated and filled with argon for three times, and then 4-methyl iodobenzene (0.5 mmol), 4-methoxy thiophenol (0.6 mmol), and 1 mL of DME were added. The reaction mixture was homogeneously stirred at 80° C. for 24 hours. After cooling, water and ethyl acetate were added and separated. The aqueous phase was extracted twice with ethyl acetate. The combined organic phase was dried over anhydrous sodium sulfate. After concentration, the residue was purified by column chromatography to give the product (N-4'-methoxyphenyl)-4-methoxy thiophenol.

$^{1}$H NMR (500 MHz, CDCl$_3$) δ 7.38 (d, J=8.6 Hz, 2H), 7.16 (d, J=8.1 Hz, 2H), 7.08 (d, J=8.0 Hz, 2H), 6.88 (d, J=8.6 Hz, 2H), 3.81 (s, 2H), 2.32 (s, 2H). $^{13}$C NMR (126 MHz, CDCl$_3$) δ 159.47, 136.12, 134.34, 129.79, 129.39, 125.63, 114.89, 55.35, 45.84, 21.01, 8.66. ESI-MS m/z 231.4 (M+H)$^+$

The results obtained by using different ligands are listed in the following table.

| Ligand | yield/% | Ligand | yield/% | Ligand | yield/% |
|---|---|---|---|---|---|
| L-13 | 70 | L-62 | 50 | L-63 | 56 |
| L-65 | 65 | L-54 | 60 | L-71 | 56 |
| L-79 | 48 | L-82 | 50 | L-84 | 44 |
| L-96 | 63 | L-112 | 72 | L-113 | 61 |
| L-114 | 70 | L-74 | 31 | L-75 | 42 |
| L-76 | 36 | L-61 | 37 | L-64 | 57 |
| L-68 | 39 | L-69 | 53 | L-70 | 61 |
| L-66 | 36 | L-67 | 45 | L-77 | 71 |
| L-78 | 65 | L-86 | 31 | L-80 | 43 |
| L-81 | 52 | L-83 | 54 | L-85 | 43 |
| L-87 | 26 | | | | |

Example 14. Synthesis of Arylsulfide by Reaction of Iodobenzene and Thiophenol

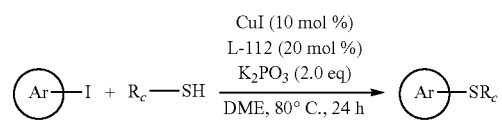

Copper iodide (0.05 mmol), ligand (0.1 mmol) and potassium phosphate (1.0 mmol) were added into a 10 mL Schlenk tube. The tube was then evacuated and filled with argon for three times, and then substituted iodobenzene (0.5 mmol), substituted thiophenol (0.6 mmol), and 1 mL of DME were added. The reaction mixture was homogeneously stirred at 80° C. for 24 hours. After cooling, water and ethyl acetate were added and separated. The aqueous phase was extracted twice with ethyl acetate. The combined organic phase was dried over anhydrous sodium sulfate. After concentration, the residue was purified by column chromatography to give the product arylsulfide.

| Product and yield | Characterization data of products |
|---|---|
| 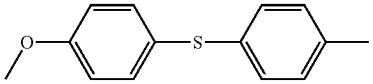 72% | $^{1}$H NMR (500 MHz, CDCl$_3$) δ 7.38 (d, J = 8.6 Hz, 2H), 7.16 (d, J = 8.1 Hz, 2H), 7.08 (d, J = 8.0 Hz, 2H), 6.88 (d, J = 8.6 Hz, 2H), 3.81 (s, 2H), 2.32 (s, 2H). $^{13}$C NMR (126 MHz, CDCl$_3$) δ 159.47, 136.12, 134.34, 129.79, 129.39, 125.63, 114.89, 55.35, 45.84, 21.01, 8.66. ES1-MS m/z 231.4 (M + H)$^+$ |
| 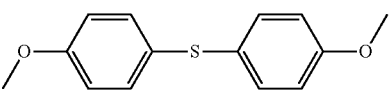 90% | $^{1}$H NMR (500 MHz, CDCl$_3$) δ 7.42 (d, J = 8.5 Hz, 1H), 7.31 (d, J = 8.6 Hz, 3H), 6.86 (d, J = 9.0 Hz, 4H), 3.80 (d, J = 4.0 Hz, 7H). $^{13}$C NMR (101 MHz, CDCl$_3$) δ 159.97, 159.02, 132.77, 132.69, 128.46, 127.48, 114.81, 114.67, 55.37. ESI-MS m/z 247.1 (M + H)$^+$ |
| 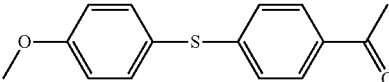 82% | $^{1}$H NMR (500 MHz, CDCl$_3$) δ 7.78 (d, J= 8.5 Hz, 1H), 7.50-7.44 (m, 1H), 7.09 (d, J = 8.5 Hz, 1H), 6.99-6.92 (m, 1H), 3.85 (s, 2H), 2.53 (s, 2H). $^{13}$C NMR (101 MHz, CDCl$_3$) δ 197.12, 160.69, 146.88, 136.83, 133.90, 128.81, 125.83, 121.41, 115.39, 55.44, 26.44. ESI-MS m/z 259.4 (M + H)$^+$ |
| 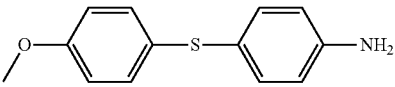 70% | $^{1}$H NMR (500 MHz, CDCl$_3$) δ 7.23 (dd, J = 8.6, 2.6 Hz, 1H), 6.82 (d, 8.5 Hz, 1H), 6.63 (d, J = 8.2 Hz, 1H), 3.76 (d, J = 23.4 Hz, 5H).$^{13}$C NMR (101 MHz, CDCl$_3$) δ 158.54, 146.24, 134.00, 131.47, 128.86, 123.49, 115.81, 114.66, 55.38. ESI-MS m/z 232.1 (M + H)$^+$ |

| Product and yield | Characterization data of products |
|---|---|
| 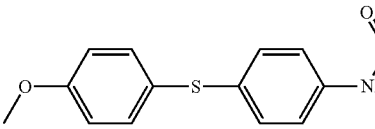 92% | $^1$H NMR (500 MHz, CDCl$_3$) δ 8.16 (s, 1H), 7.36 (dd, J = 28.9, 8.7 Hz, 4H), 7.14 (d, J = 8.6 Hz, 2H), 6.86 (d, J = 8.7 Hz, 2H), 3.79 (s, 3H), 2.11 (s, 3H). $^{13}$C NMR (101 MHz, CDCl$_3$) δ 169.03, 159.58, 136.49, 134.39, 133.09, 129.95, 125.29, 120.88, 115.00, 55.41, 24.39. ESI-MS m/z 274.1 (M + H)$^+$ |

Example 15. Reaction of 4-Methoxy Bromobenzene and Other Coupling Reagent

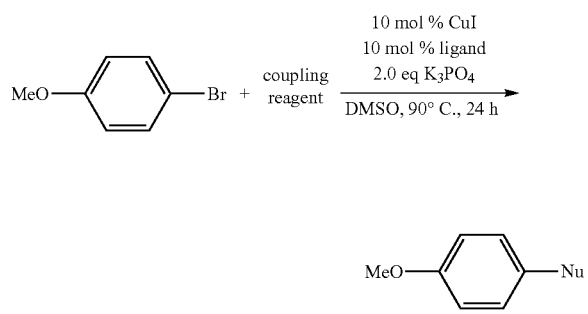

Copper salt catalyst (0.1 mmol), ligand (0.1 mmol) and potassium phosphate (1.0 mmol) were added into a 10 mL Schlenk tube. The tube was then evacuated and filled with argon for three times, and then aryl chloride (1.0 mmol), 1 mL of DMSO and nucleophile (2.0 mmol) were added. The reaction mixture was homogeneously stirred at 90° C. for 24 hours. After cooling, water and ethyl acetate were added and separated. The aqueous phase was extracted twice with ethyl acetate. The combined organic phase was dried over anhydrous sodium sulfate. After concentration, the residue was purified by column chromatography to give the coupling product.

| Coupling reagent | Copper catalyst | ligand | Product and yield |
|---|---|---|---|
| NH$_3$·H$_2$O | CuI | L-15 | 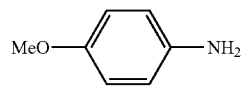 90% |
| PhOH | CuI | L-13 | 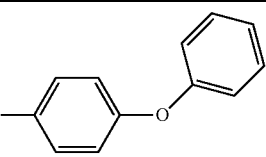 74% |
| MeSO$_2$Na | CuI | L-92 | 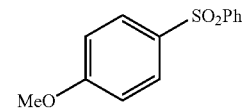 83% |

Example 16. Coupling of Aryl Chloride with Sodium Alkylsulfinate or Sodium Arylsulfinate (Gram-Level Reaction)

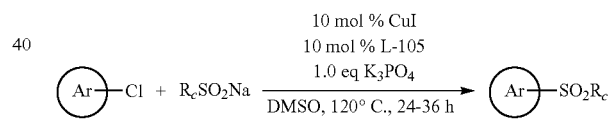

Sodium alkylsulfinate or sodium arylsulfinate (6.5 mmol), copper iodide (0.5 mmol), ligand (0.5 mmol) and potassium phosphate (5.0 mmol) were added into a 10 mL Schlenk tube. The tube was evacuated and filled with argon for three times, and then aryl chloride (5 mmol) and 3 mL of DMSO were added. The reaction mixture was homogeneously stirred at 120° C. for 24-36 hours. After cooling, the contents of the of Schlenk tube were washed with ethyl acetate, and filtered through silica gel and diatomite plug. The filtrate was concentrated and purified by column chromatography to give the corresponding product.

| Product and yield | Characterization data of products |
|---|---|
| 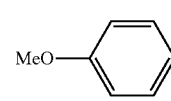 75% | $^1$H NMR (500 MHz, CDCl$_3$) δ 7.87 (d, J = 8.9 Hz, 2H), 7.02 (d, J = 8.9 Hz, 2H), 3.89 (s, 3H), 3.03 (s, 3H). $^{13}$C NMR (125 MHz, CDCl$_3$) δ 163.68, 132.26, 129.49, 114.51, 55.73, 44.82. MS-EI: 186 (M$^+$) |

| Product and yield | Characterization data of products |
|---|---|
| <br>80% | $^1$H NMR (500 MHz, CDCl3) δ 7.83 (d, J = 8.3 Hz, 2H), 7.37 (d, J = 8.1 Hz, 2H), 3.03 (s, 3H), 2.46 (s, 3H). $^{13}$C NMR (125 MHz, CDCl$_3$) δ 144.80, 137.87, 130.09, 127.53, 44.77, 21.77; MS-EI: 170 (M$^+$). |
| <br>81% | $^1$H NMR (500 MHz, CDCl3) δ 8.01 (d, J = 8.4 Hz, 2H), 7.78 (d, J = 8.4 Hz, 2H), 7.64-7.59 (m, 3H), 7.49 (t, J = 7.4 Hz, 3H), 7.46-7.41 (m, 1H), 3.10 (s, 3H). $^{13}$C NMR (125 MHz, CDCl$_3$) δ 146.87, 139.26, 139.21, 129.25, 128.83, 128.14, 128.05, 127.53, 44.78; MS-EI: 232 (M$^+$). |
| <br>83% | $^1$H NMR (500 MHz, CDCl3) δ 7.82 (d, J = 8.5 Hz, 2H), 7.35 (d, J = 8.5 Hz, 2H), 3.03 (s, 3H), 2.53 (s, 3H). $^{13}$C NMR (125 MHz, CDCl$_3$) δ 147.34. 136.35, 127.79, 125.62, 44.83, 14.91; MS-EI: 202 (M$^+$). |
| <br>76% | $^1$H NMR (500 MHz, CDCl3) δ 7.69 (d, J = 8.7 Hz, 2H), 6.71 (d, J = 8.7 Hz, 2H), 4.19 (s, 2H), 3.00 (s, 3H). $^{13}$C NMR (125 MHz, CDCl$_3$) δ 151.57, 129.53, 129.75, 114.19, 45.12; MS-EI: 171 (M$^+$). |
| <br>70% | $^1$H NMR (500 MHz, DMSO-d6) δ = 8.17 (d, J = 8.2, 2H), 8.05 (d, J = 8.3, 2H), 3.32 (s, 3H). |
| <br>96% | $^1$H NMR (500 MHz, DMSO-d6) δ = 7.71 (d, J = 9.0, 2H), 7.08 (d, J = 9.0, 2H), 3.73 (t, J = 5.0, 4H), 3.28 (t, J = 5.0, 4H), 3.10 (s, 3H). $^{13}$C NMR (126 MHz, DMSO-d6) δ 154.01, 128.97, 128.49, 113.48, 65.78, 46.82, 44.19. |
| <br>74% | $^1$H NMR (500 MHz, CDCl3) δ 7.52 (d, J = 7.8 Hz, 1H), 7.47 (t, J = 7.9 Hz, 1H), 7.44-7.42 (m, 1H), 7.18-7.15 (m, 1H), 3.87 (s, 3H), 3.05 (s, 3H). $^{13}$C NMR (125 MHz, CDCl$_3$) δ 160.22, 141.86, 130.62, 120.29, 119.58, 111.95, 55.86, 44.58; MS-EI: 186 (M$^+$); |
| <br>74% | $^1$H NMR (500 MHz, DMSO-d6) δ = 7.49 (dd, J = 11.1, 2.0, 1H), 7.42 (dd, J = 8.4, 2.0, 1H), 6.88 (t, J = 8.5, 1H), 6.16 (s, 2H), 3.10 (s, 3H). $^{13}$C NMR (125 MHz, DMSO-d6) δ 149.71, 147.80, 141.90, 141.80, 126.04, 126.00, 124.69, 124.67, 114.93, 114.89, 114.24, 114.08, 44.21. |
| <br>72% | $^1$H NMR (500 MHz, CDCl$_3$) δ 7.50 (dd, J = 8.2, 1.8 Hz, 1H), 7.33 (d, J = 1.8 Hz, 1H), 6.93 (d, J = 8.2 Hz, 1H), 6.10 (s, 2H), 3.02 (s, 3H). $^{13}$C NMR (125 MHz, CDCl$_3$) δ 152.31, 148.49, 134.13, 123.43, 108.71, 107.65, 102.60, 44.90; MS-EI: 200 (M$^+$); HRMS (EI) Calcd. for C$_8$H$_8$O$_4$S (M$^+$): 200.0143, Found: 200.0146. |
| <br>75% | $^1$H NMR (500 MHz, DMSO-d6) δ = 8.86 (d, J = 2.0, 1H), 8.46 (dd, J = 8.1, 0.9, 1H), 8.22 (dd, J = 8.5, 2.1, 1H), 8.11 (d, J = 8.5, 1H), 7.88 (d, J = 7.7, 1H), 7.84-7.78 (m, 1H), 7.66-7.60 (m, 1H), 3.34 (s, 3H). $^{13}$C NMR (126 MHz, DMSO-d6) δ 178.03, 142.33, 138.87, 135.86, 133.57, 129.89, 129.15, 128.26, 128.21, 128.06, 128.00, 127.53, 126.77, 43.44. |

| Product and yield | Characterization data of products |
|---|---|
| 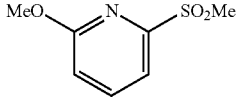<br>82% | $^1$H NMR (500 MHz, DMSO-d6) δ = 8.00 (t, 1H), 7.62 (d, J = 7.2, 1H), 7.15 (d, J = 8.3, 1H), 3.94 (s, 3H), 3.28 (s, 3H). $^{13}$C NMR (126 MHz, DMSO-d6) δ 163.42, 154.85, 141.14, 115.65, 113.90, 53.90, 39.56. |
| 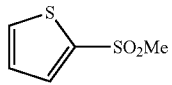<br>75% | $^1$H NMR (500 MHz, CDCl3) δ 7.71-7.68 (m, 2H), 7.15-7.12 (m, 1H), 3.17 (s, 3H). $^{13}$C NMR (125 MHz, CDCl$_3$) δ 141.82, 133.78, 133.55, 128.0, 46.20; MS-EI: 162 (M$^+$); HRMS (EI) Calcd. for C$_5$H$_6$O$_2$S$_2$ (M$^+$): 161.9809, Found: 161.9806. |
| 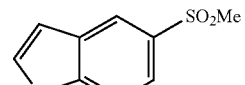<br>76% | $^1$H NMR (500 MHz, CDCl3) δ 8.28 (d, J = 1.8 Hz, 1H), 7.68 (dd, J = 8.7, 1.8 Hz, 1H), 7.39 (d, J = 8.7 Hz, 1H), 7.32-7.27 (m, 4H), 7.10 (d, J = 6.3 Hz, 2H), 6.69 (d, J = 2.9 Hz, 2H), 5.36 (s, 2H), 3.04 (s, 3H). $^{13}$C NMR (125 MHz, CDCl$_3$) δ 138.42, 136.49, 131.60, 131.06, 128.96, 128.30, 128.03, 126.78, 121.83, 120.15, 110.46, 103.49, 50.48, 45.21; MS-EI: 285 (M$^+$); HRMS (EI) Calcd. for C$_{16}$H$_{15}$NO$_2$S (M$^+$): 285.0824, Found: 285.0831. |
| 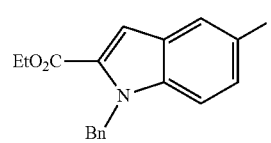<br>72% | $^1$H NMR (500 MHz, DMSO-d6) δ = 8.40 (d, J = 0.9, 1H), 7.89-7.78 (m, 2H), 7.61 (s, 1H), 7.27 (t, J = 7.4, 2H), 7.21 (t, J = 7.3, 1H), 7.04 (d, J = 7.2, 2H), 4.31 (q, J = 7.1, 2H), 3.21 (s, 3H), 1.29 (t, J = 7.1, 3H). $^{13}$C NMR (126 MHz, DMSO-d6) δ 160.72, 140.58, 137.83, 133.44, 129.69, 128.55, 127.20, 126.16, 124.79, 123.16, 122.90, 112.37, 112.01, 60.91, 47.53, 44.12, 14.02. MS-ESI: 358 (M + H)$^+$ |

Example 17. Coupling of Aryl Iodide or Aryl Bromide with Sodium Alkylsulfinate or Sodium Arylsulfinate (Gram-Level Reaction)

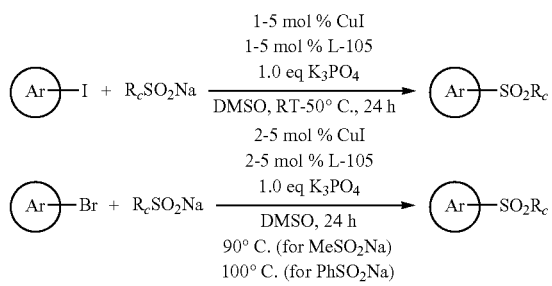

Sodium alkylsulfinate or sodium arylsulfinate (6.5 mmol), copper iodide (of which the dosage was shown in the following table), ligand (of which the dosage was shown in the following table) and potassium phosphate (5.0 mmol) were added into a 10 mL Schlenk tube. The tube was evacuated and filled with argon for three times, and then aryl chloride (5 mmol) and 4 mL of DMSO were added. The reaction mixture was homogeneously stirred at corresponding temperature for 24 hours. After cooling, the contents of the of Schlenk tube were washed with ethyl acetate, and filtered through silica gel and diatomite plug. The filtrate was concentrated and purified by column chromatography to give the corresponding product.

| Product and yield | Characterization data of products |
|---|---|
| 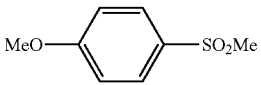<br>iodide: 1 mol %CuI/<br>1 mol %L-150,<br>RT. yield: 95% | $^1$H NMR (500 MHz, CDCl$_3$) δ 7.87 (d, J = 8.9 Hz, 2H), 7.02 (d, J = 8.9 Hz, 2H), 3.89 (s, 3H), 3.03 (s, 3H). $^{13}$C NMR (125 MHz, CDCl$_3$) δ 163.68, 132.26, 129.49, 114.51, 55.73, 44.82. MS-EI: 186 (M$^+$) |

| Product and yield | Characterization data of products |
|---|---|
| 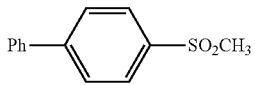<br>Ph—⟨C₆H₄⟩—SO₂CH₃<br>iodide: 1 mol %CuI/<br>1 mol %L-105,<br>RT. yield: 90%<br>bromide: 2 mol %CuI/<br>2 mol %L-105,<br>90° C.<br>yield: 95% | ¹H NMR (500 MHz, CDCl3) δ 8.01 (d, J = 8.4 Hz, 2H), 7.78 (d, J = 8.4 Hz, 2H), 7.64-7.59 (m, 3H), 7.49 (t, J = 7.4 Hz, 3H), 7.46-7.41 (m, 1H), 3.10 (s, 3H). ¹³C NMR (125 MHz, CDCl₃) δ 146.87, 139.26, 139.21, 129.25, 128.83, 128.14, 128.05, 127.53, 44.78; MS-EI: 232 (M⁺). |
| 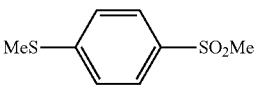<br>MeS—⟨C₆H₄⟩—SO₂Me<br>iodide: 1 mol %CuI/<br>1 mol %L-150,<br>RT. yield: 94%<br>bromide: 2 mol %CuI/<br>2 mol %L-150,<br>90° C. yield: 95% | ¹H NMR (500 MHz, CDCl3) δ 7.82 (d, J = 8.5 Hz, 2H), 7.35 (d, J = 8.5 Hz, 2H), 3.03 (s, 3H), 2.53 (s, 3H). ¹³C NMR (125 MHz, CDCl₃) δ 147.34, 136.35, 127.79, 125.62, 44.83, 14.91; MS-EI: 202 (M⁺). |
| 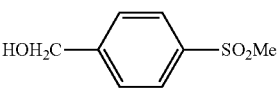<br>HOH₂C—⟨C₆H₄⟩—SO₂Me<br>iodide: 1 mol %CuI/<br>1 mol %L-105,<br>RT. yield: 71%<br>bromide: 2 mol %CuI/<br>2 mol %L-105, 90° C.<br>yield: 86% | ¹H NMR (500 MHz, CDCl3) δ 7.83 (d, J = 8.4 Hz, 2H), 7.51 (d, J = 8.4 Hz, 2H), 4.77 (s, 2H), 3.01 (s, 3H), 2.64 (s, 1H). ¹³C NMR (125 MHz, CDCl₃) δ 147.43, 139.44, 127.67, 127.34, 64.24, 44.69; MS-EI: 186 (M⁺); HRMS (EI) Calcd. for $C_8H_{10}O_3S$ (M⁺): 186.0351, Found: 186.0347. |
| 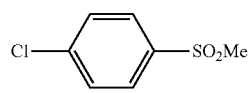<br>Cl—⟨C₆H₄⟩—SO₂Me<br>iodide: 1 mol %CuI/<br>1 mol %L-150,<br>RT. yield: 85% | ¹H NMR (500 MHz, CDCl3) δ 7.69 (d, J = 8.7 Hz, 2H), 6.71 (d, J = 8.7 Hz, 2H), 4.19 (s, 2H), 3.00 (s, 3H). ¹³C NMR (125 MHz, CDCl₃) δ 151.57, 129.53, 129.75, 114.19, 45.12; MS-EI: 171 (M⁺). |
| 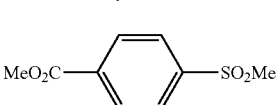<br>MeO₂C—⟨C₆H₄⟩—SO₂Me<br>iodide: 1 mol %CuI/<br>1 mol %L-150,<br>RT. yield: 65%<br>iodide: 2 mol %CuI/<br>2 mol %L-105, 50° C.,<br>yield: 73% | ¹H NMR (500 MHz, CDCl3) δ 8.23 (d, J = 8.5 Hz, 2H), 8.03 (d, J = 8.5 Hz, 2H), 3.98 (s, 3H), 3.08 (s, 3H). ¹³C NMR (125 MHz, CDCl₃) δ 165.54, 144.39, 134.99, 130.66, 127.61, 52.87, 44.44; MS-EI: 214 (M⁺). |
| 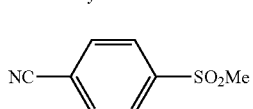<br>NC—⟨C₆H₄⟩—SO₂Me<br>iodide: 1 mol %CuI/<br>1 mol %L-150,<br>RT. yield: 62%<br>iodide: 2 mol %CuI/<br>2 mol %L-150,<br>50° C., yield: 81% | ¹H NMR (500 MHz, CDCl3) δ 8.06 (d, J = 8.4 Hz, 2H), 7.88 (d, J = 8.6 Hz, 2H), 3.08 (s, 3H). ¹³C NMR (125 MHz, CDCl₃) δ 144.48, 133.27, 128.24, 117.58, 117.14, 44.25; MS-EI: 181 (M⁺); |
| 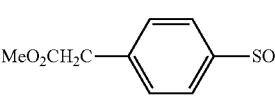<br>MeO₂CH₂C—⟨C₆H₄⟩—SO₂Me<br>bromide: 2 mol %CuI/<br>2 mol %L-105, 90° C.<br>yield: 87% | ¹H NMR (500 MHz, DMSO-d6) δ = 7.89 (d, J = 8.3 Hz, 2H), 7.55 (d, J = 8.3 Hz, 2H), 3.85 (s, 2H), 3.63 (s, 3H), 3.21 (s, 3H). ¹³C NMR (126 MHz, DMSO-d6) δ 171.40, 140.84, 139.86, 130.89, 127.44, 52.35, 43.97. MS-ESI: 228.9 (M + H)⁺ |

-continued

| Product and yield | Characterization data of products |
|---|---|
| 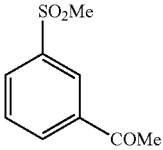<br>iodide: 1 mol %CuI/<br>1 mol %L-105, RT.<br>yield: 72% | $^1$H NMR (500 MHz, CDCl3) δ 8.46 (s, 1H), 8.21 (d, J = 7.6 Hz, 1H), 8.12 (d, J = 7.6 Hz, 1H), 7.69 (t, J = 7.7 Hz, 1H), 3.08 (s, 3H), 2.65 (s, 3H). $^{13}$C NMR (125 MHz, CDCl$_3$) δ 196.21, 141.52, 138.15, 133.21, 131.53, 130.09, 127.32, 44.51, 26.86; MS-EI: 198 (M$^+$). |
| 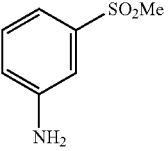<br>bromide: 5 mol %CuI/<br>5 mol %L-105, 90° C.<br>yield: 92% | $^1$H NMR (500 MHz, DMSO-d6) δ = 7.25 (t, J = 7.9, 1H), 7.08 (t, J = 2.0, 1H), 7.02-6.96 (m, 1H), 6.87-6.81 (m, 1H), 5.65 (s, 2H), 3.10 (s, 3H). $^{13}$C NMR (126 MHz, DMSO-d6) δ 150.01, 141.84, 130.32, 118.62, 113.76, 111.41, 44.12. MS-ESI: 171.9 (M + H)$^+$. |
| 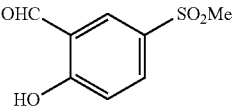<br>iodide: 5 mol %CuI/<br>5 mol %L-105, 50° C.<br>yield: 80% | $^1$H NMR (500 MHz, CDCl3) δ 11.48 (s, 1H), 9.96 (s, 1H), 8.23 (d, J = 2.3 Hz, 1H), 8.02 (dd, J = 8.8, 2.3 Hz, 1H), 7.14 (d, J = 8.8 Hz, 1H), 3.06 (s, 3H). $^{13}$C NMR (125 MHz, CDCl$_3$) δ 195.87, 165.41, 135.28, 134.12, 132.27, 120.10, 119.36, 44.75; MS-EI; 200 (M$^+$); HRMS (EI) Calcd. for C$_8$H$_8$N$_3$O$_4$S (M$^+$): 200.0143, Found: 200.0146. |
| 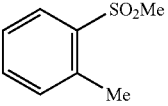<br>iodide: 2 mol %CuI/<br>2 mol %L-105, 50° C.,<br>yield: 12% | $^1$H NMR (500 MHz, CDCl3) δ 8.02 (dd, J = 7.9, 1.4 Hz, 1H), 7.51 (td, J = 7.5, 1.4 Hz, 1H), 7.36 (t, J = 7.7 Hz, 1H), 7.33 (d, J = 7.6 Hz, 1H), 3.06 (s, 3H), 2.70 (s, 3H). $^{13}$C NMR (125 MHz, CDCl$_3$) δ 138.79, 137.62, 133.77, 132.80, 129.30, 126.80, 43.76, 20.35; MS-EI: 170 (M$^+$). |
| 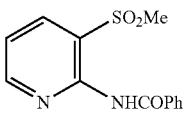<br>iodide: 1 mol %CuI/<br>1 mol %L-105, RT.<br>yield: 95% | $^1$H NMR (500 MHz, CDCl3) δ 9.55 (s, 1H), 8.77 (dd, J = 4.7, 1.5 Hz, 1H), 8.60 (dd, J = 8.1, 1.4 Hz, 1H), 7.70 (d, J = 7.7 Hz, 2H), 7.64 (dd, J = 8.1, 4.7 Hz, 1H), 7.35 (t, J = 7.9 Hz, 2H), 7.15 (t, J = 7.4 Hz, 1H), 3.64 (s, 3H). $^{13}$C NMR (125 MHz, CDCl$_3$) δ 161.38, 151.52, 149.93, 139.71, 138.03, 137.16, 129.14, 126.27, 125.04, 120.24, 45.15; MS-EI: 276 (M$^+$). |
| 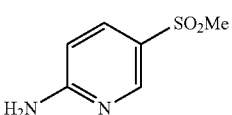<br>iodide: 2 mol %CuI/<br>2 mol %L-105, 50° C.,<br>yield: 79% | $^1$H NMR (500 MHz, d6-DMSO) δ 8.35 (s, 1H), 7.75 (d, J = 8.7 Hz, 1H), 6.99 (s, 2H), 6.52 (d, J = 8.9 Hz, 1H), 3.11 (s, 3H). $^{13}$C NMR (125 MHz, CDCl$_3$) δ 162.49, 148.66, 135.80, 123.77, 107.18, 44.51; MS-EI: 172 (M$^+$); HRMS (EI) Calcd. for C$_6$H$_8$N$_2$O$_2$S (M$^+$): 172.0306, Found: 172.0312. |
| 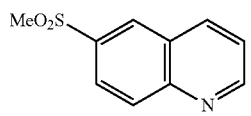<br>iodide: 1 mol %CuI/<br>1 mol %L-105,<br>RT. yield: 87%<br>bromide: 2 mol %CuI/<br>2 mol %L-105,<br>90° C. yield: 92% | $^1$H NMR (400 MHz, CDCl3) δ 9.09 (d, J = 3.8 Hz, 1H), 8.53 (s, 1H), 8.34-8.27 (m, 2H), 8.14 (d, J = 8.8 Hz, 1H), 7.57 (dd, J = 8.2, 4.2 Hz, 1H), 3.14 (s, 3H). $^{13}$C NMR (125 MHz, CDCl$_3$) δ 153.68, 149.88, 138.32, 137.49, 131.64, 129.36, 127.44, 126.05, 122.92, 44.62; MS-EI: 207 (M$^+$); |

-continued

| Product and yield | Characterization data of products |
|---|---|
| 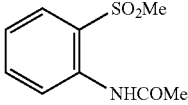<br>bromide: 5 mol %CuI/<br>25 mol %L-150, 90° C.<br>yield: 69% | $^1$H NMR (500 MHz, DMSO-d6) δ = 9.57 (s, 1H), 7.99 (d, J = 8.2, 1H), 7.90 (dd, J = 7.9, 1.4, 1H), 7.74-7.68 (m, 1H), 7.44-7.38 (m, 1H), 3.26 (s, 3H), 2.13 (s, 3H). $^{13}$C NMR (126 MHz, DMSO-d6) δ 168.87, 136.49, 134.66, 129.18, 125.61, 125.19, 43.42, 24.07. MS-ESI: 214 (M + H)$^+$ |
| 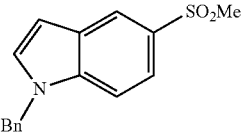<br>iodide: 1 mol %CuI/<br>1 mol %L-105, RT.<br>yield: 89%<br>bromide: 2 mol %CuI/<br>2 mol %L-105, 90° C.<br>yield: 92% | $^1$H NMR (500 MHz, CDCl3) δ 8.28 (d, J = 1.8 Hz, 1H), 7.68 (dd, J = 8.7, 1.8 Hz, 1H), 7.39 (d, J = 8.7 Hz, 1H), 7.32-7.27 (m, 4H), 7.10 (d, J = 6.3 Hz, 2H), 6.69 (d, J = 2.9 Hz, 2H), 5.36 (s, 2H), 3.04 (s, 3H). $^{13}$C NMR (125 MHz, CDCl$_3$) δ 138.42, 136.49, 131.60, 131.06, 128.96, 128.30, 128.03, 126.78, 121.83, 120.15, 110.46, 103.49, 50.48, 45.21; MS-EI: 285 (M$^+$); HRMS (EI) Calcd. for C$_{16}$H$_{15}$NO$_2$S (M$^+$): 285.0824, Found: 285.0831. |
| 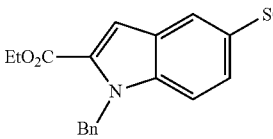<br>bromide: 2 mol %CuI/<br>2 mol %L-105, 90° C.<br>yield: 92% | $^1$H NMR (500 MHz, DMSO-d6) δ = 8.40 (d, J = 0.9, 1H), 7.89-7.78 (m, 2H), 7.61 (s, 1H), 7.27 (t, J = 7.4, 2H), 7.21 (t, J = 7.3, 1H), 7.04 (d, J = 7.2, 2H), 4.31 (q, J = 7.1, 2H), 3.21 (s, 3H), 1.29 (t, J = 7.1, 3H). $^{13}$C NMR (126 MHz, DMSO-d6) δ 160.72, 140.58, 137.83, 133.44, 129.69, 128.55, 127.20, 126.16, 124.79, 123.16, 122.90, 112.37, 112.01, 60.91, 47.53, 44.12, 14.02. MS-ESI: 357 (M$^+$) |
| 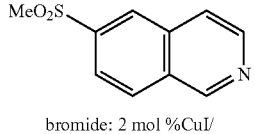<br>bromide: 2 mol %CuI/<br>2 mol %L-105, 90° C.<br>yield: 85% | $^1$H NMR (500 MHz, DMSO-d6) δ = 9.47 (s, 1H), 8.67 (d, J = 5.7, 1H), 8.65 (s, 1H), 8.36 (d, J = 8.6, 1H), 8.13 (dd, J = 8.6, 1.6, 1H), 8.07 (d, J = 5.7, 1H), 3.37 (s, 3H). $^{13}$C NMR (126 MHz, DMSO-d6) δ 152.59, 144.37, 142.01, 134.25, 129.55, 129.09, 126.81, 123.78, 121.36, 43.21. |
| 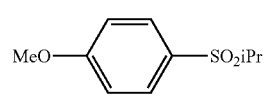<br>iodide: 1 mol %CuI/<br>1 mol %L-150, RT.<br>yield: 53%<br>iodide: 3 mol %CuI/<br>3 mol %L-105, 50° C.<br>yield: 83% | $^1$H NMR (500 MHz, CDCl3) δ 7.79 (d, J = 8.9 Hz, 2H), 7.01 (d, J = 8.9 Hz, 2H), 3.88 (d, J = 1.2 Hz, 3H), 3.19-3.11 (m, 1H), 1.27 (d, J = 6.9 Hz, 6H). $^{13}$C NMR (125 MHz, CDCl$_3$) δ 163.79, 131.30, 128.48, 114.37, 55.86, 55.79. 15.97; MS-EI: 214 (M$^+$); HRMS (EI) Calcd. for C$_{10}$H$_{14}$O$_3$S (M$^+$): 214.0664, Found: 214.0657. |
| 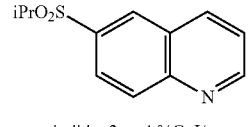<br>iodide: 3 mol %CuI/<br>3 mol %L-105, 50° C.<br>yield: 78% | $^1$H NMR (500 MHz, CDCl3) δ 9.06-9.01 (m, 1H), 8.43 (d, J = 1.7 Hz, 1H), 8.29 (d, J = 8.1 Hz, 1H), 8.21 (d, J = 8.8 Hz, 1H), 8.05 (dd, J = 8.8, 1.9 Hz, 1H), 7.52 (dd, J = 8.3, 4.2 Hz, 1H), 3.33-3.21 (m, 1H), 1.29 (d, J = 6.9 Hz, 6H). $^{13}$C NMR (125 MHz, CDCl$_3$) δ 153.51, 149.73, 137.35, 134.83, 131.0, 130.98, 127.37, 127.24, 122.72, 55.67, 15.73; MS-EI: 235 (M$^+$); HRMS (EI) Calcd. for C$_{12}$H$_{13}$NO$_2$S (M$^+$): 235.0667, Found: 235.0663. |
| 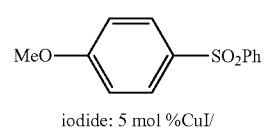<br>iodide: 5 mol %CuI/<br>5 mol %L-150, RT.<br>yield: 92% | $^1$H NMR (500 MHz, CDCl$_3$) δ 7.93-7.90 (m, 2H), 7.88 (d, J = 9.0 Hz, 2H), 7.56-7.51 (m, 1H), 7.51-7.46 (m, 2H), 6.96 (d, J = 9.0 Hz, 2H), 3.84 (s, 3H). $^{13}$C NMR (125 MHz, CDCl$_3$) δ 163.50, 142.50, 133.26, 132.97, 130.03, 129.33, 127.45, 114.64, 55.78; MS-EI: 248 (M$^+$) |

-continued

| Product and yield | Characterization data of products |
|---|---|
| 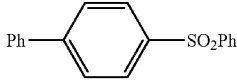<br>Ph—⟨⟩—SO₂Ph<br>iodide: 5 mol %CuI/<br>5 mol %L-150, RT.<br>yield: 83%<br>bromide: 2 mol %CuI/<br>2 mol %L-105, 100° C.<br>yield: 95% | $^1$H NMR (500 MHz, CDCl3) δ 8.03-7.97 (m, 4H), 7.70 (d, J = 8.5 Hz, 2H), 7.60-7.55 (m, 3H), 7.52 (t, J = 7.5 Hz, 2H), 7.46 (t, J = 7.4 Hz, 2H), 7.43-7.38 (m, 1H). $^{13}$C NMR (125 MHz, CDCl$_3$) δ 146.31, 141.86, 140.24, 139.29, 133.32, 129.45, 129.18, 128.72, 128.33, 128.07, 127.78, 127.48; MS-EI: 294 (M⁺); HRMS (EI) Calcd. for C$_{18}$H$_{14}$O$_2$S (M⁺): 294.0715, Found: 294.0718. |
| <br>MeOC—⟨⟩—SO₂Ph<br>iodide: 5 mol %CuI/<br>5 mol %L-105, 50° C.,<br>yield: 80%<br>bromide: 2 mol %CuI/<br>2 mol %L-105, 100° C.<br>yield: 81% | $^1$H NMR (500 MHz, CDCl3) δ 8.06-8.01 (m, 4H), 7.95 (d, J = 7.8 Hz, 2H), 7.61-7.57 (m, 1H), 7.54-7.50 (m, 2H), 2.61 (s, 3H). $^{13}$C NMR (125 MHz, CDCl$_3$) δ 196.80, 145.54, 140.88, 140.45, 133.78, 129.60, 129.19, 128.10, 127.97, 27.02; MS-EI: 260 (M⁺); HRMS (EI) Calcd. for C$_{14}$H$_{12}$O$_3$S (M⁺): 260.0507, Found: 260.0513. |
| 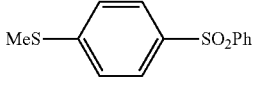<br>MeS—⟨⟩—SO₂Ph<br>bromide: 2 mol %CuI/<br>2 mol %L-105, 100° C.<br>yield: 95% | $^1$H NMR (500 MHz, DMSO-d6) δ = 7.93 (d, J = 7.6, 2H), 7.83 (d, J = 8.5 Hz, 2H), 7.65 (t, J = 7.3, 1H), 7.59 (t, J = 7.6, 2H), 7.42 (d, J = 8.5, 2H), 2.49 (s, 3H). $^{13}$C NMR (126 MHz, DMSO-d6) δ 146.56, 141.44, 136.55, 133.48, 129.67, 127.70, 127.08, 125.63, 13.85. |
| 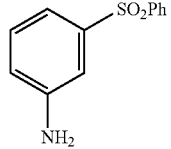<br>bromide: 5 mol %CuI/<br>5 mol %L-105, 100° C.<br>yield: 82% | $^1$H NMR (500 MHz, DMSO-d6) δ = 7.94 (d, J = 7.4, 2H), 7.70 (dd, J = 8.1, 1.3, 1H), 7.66 (t, J = 7.4, 2H), 7.58 (t, J = 7.6, 2H), 7.33-7.26 (m, 1H), 6.79 (d, J = 8.3, 1H), 6.70-6.65 (m, 1H), 6.17 (s, 2H). $^{13}$C NMR (126 MHz, DMSO-d6) δ 147.23, 141.39, 134.97, 133.30, 129.29, 129.09, 126.64, 119.65, 117.28, 115.87. |
| 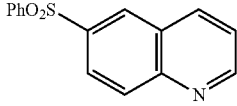<br>iodide: 5 mol %CuI/<br>5 mol %L-105, RT.<br>yield: 84% | $^1$H NMR (500 MHz, CDCl3) δ 9.04 (dd, J = 4.2, 1.7 Hz, 1H), 8.58 (d, J = 2.0 Hz, 1H), 8.30 (d, J = 8.4 Hz, 1H), 8.19 (d, J = 8.9 Hz, 1H), 8.09 (dd, J = 8.9, 2.1 Hz, 1H), 8.03-8.00 (m, 2H), 7.59-7.56 (m, 1H), 7.54-7.50 (m, 3H). $^{13}$C NMR (125 MHz, CDCl$_3$) δ 153.48, 149.63, 141.25, 139.44, 137.47, 133.62, 131.51, 129.56, 129.22, 127.96, 127.48, 126.59, 122.78; MS-EI: 269 (M⁺); HRMS (EI) Calcd. for C$_{15}$H$_{11}$NO$_2$S (M⁺): 269.0511, Found: 269.0521. |
| 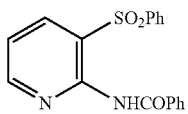<br>iodide: 5 mol %CuI/<br>5 mol %L-105, RT.<br>yield: 88% | $^1$H NMR (500 MHz, CDCl3) δ 9.20 (s, 1H), 8.81 (dd, J = 8.1, 1.6 Hz, 1H), 8.77 (dd, J = 4.8, 1.6 Hz, 1H), 8.05-8.02 (m, 2H), 7.70-7.67 (m, 1H), 7.64 (d, J = 1.1 Hz, 2H), 7.58 (t, J = 7.4 Hz, 1H), 7.51 (t, J = 7.6 Hz, 2H), 7.34 (t, J = 7.9 Hz, 2H), 7.13 (t, J = 7.4 Hz, 1H). $^{13}$C NMR (125 MHz, CDCl$_3$) δ 160.87, 151.64, 150.14, 141.12, 139.97, 138.13, 137.40, 133.39, 129.13, 128.75, 128.50, 126.06, 124.84, 102.14; MS-EI: 338 (M⁺); HRMS (EI) Calcd. for C$_{18}$H$_{14}$N$_2$O$_3$S (M⁺): 338.0725, Found: 338.0721 |
| 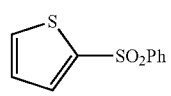<br>iodide: 5 mol %CuI/<br>5 mol %L-105, RT.<br>yield: 63% | $^1$H NMR (500 MHz, CDCl3) δ 7.98 (d, J = 7.6 Hz, 2H), 7.69 (d, J = 3.7 Hz, 1H), 7.63 (d, J = 4.9 Hz, 1H), 7.57 (t, J = 7.3 Hz, 1H), 7.51 (t, J = 7.6 Hz, 2H), 7.09-7.06 (m, 1H). $^{13}$C NMR (125 MHz, CDCl$_3$) δ 143.12, 142.17, 134.01, 133.49, 133.41, 129.42, 127.97, 127.40; MS-EI: 224 (M⁺); HRMS (EI) Calcd. for C$_{10}$H$_8$O$_2$S$_2$ (M⁺): 223.9966, Found: 223.9967. |

| Product and yield | Characterization data of products |
|---|---|
| 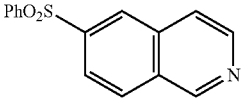<br>bromide: 2 mol %CuI/<br>2 mol %L-105, 100° C.<br>yield: 80% | $^1$H NMR (500 MHz, DMSO-d6) δ = 9.42 (s, 1H), 8.77 (s, 1H), 8.64 (d, J = 5.7, 1H), 8.30 (d, J = 8.7, 1H), 8.12-8.01 (m, 4H), 7.68 (t, J = 7.3, 1H), 7.62 (t, J = 7.5, 2H). $^{13}$C NMR (126 MHz, DMSO-d6) δ 152.57, 144.49, 142.22, 140.30, 134.33, 134.01, 129.98, 129.81, 128.86, 127.64, 127.32, 123.92, 121.34. |
| 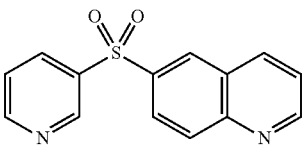<br>iodide: 5 mol %CuI/<br>5 mol %L-105, 50° C.,<br>yield: 62% | $^1$H NMR (500 MHz, CDCl3) δ 9.19 (d, J = 2.3 Hz, 1H), 9.03 (d, J = 2.8 Hz, 1H), 8.76 (d, J = 3.8 Hz, 1H), 8.60-8.56 (m, 1H), 8.29 (d, J = 8.3 Hz, 1H), 8.25 (d, J = 8.0 Hz, 1H), 8.19 (d, J = 8.9 Hz, 1H), 8.07 (dd, J = 8.9, 1.7 Hz, 1H), 7.52 (dd, J = 8.3, 4.2 Hz, 1H), 7.44 (dd, J = 8.1, 4.8 Hz, 1H). $^{13}$C NMR (125 MHz, CDCl$_3$) δ 154.0, 153.79, 149.72, 148.88, 138.44, 137.92, 137.44, 135.46, 131.85, 129.65, 127.45, 126.20, 124.03, 122.94; MS-EI: 270 (M$^+$); HRMS (EI) Calcd. for C$_{14}$H$_{10}$N$_2$O$_2$S (M$^+$): 270.0463, Found: 270.0466. |
| 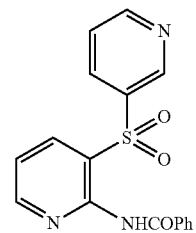<br>iodide: 5 mol %CuI/<br>5 mol %L-105, 50° C.,<br>yield: 71% | $^1$H NMR (500 MHz, CDCl3) δ 9.41 (s, 1H), 9.12 (d, J = 1.7 Hz, 1H), 8.93 (d, J = 8.1 Hz, 1H), 8.83 (d, J = 4.6 Hz, 1H), 8.77 (d, J = 4.7 Hz, 1H), 8.47 (d, J = 8.1 Hz, 1H), 7.76 (dd, J = 8.1, 4.7 Hz, 1H), 7.64 (d, J = 7.9 Hz, 2H), 7.49 (dd, J = 8.1, 4.9 Hz, 1H), 7.35 (t, J = 7.8 Hz, 2H), 7.15 (t, J = 7.4 Hz, 1H). $^{13}$C NMR (125 MHz, CDCl$_3$) δ 160.32, 153.51, 151.88, 149.64, 149.36, 140.26, 138.26, 137.99, 137.23, 136.83, 129.20, 126.42, 125.02, 123.24, 120.08; MS-EI: 339 (M$^+$); HRMS (EI) Calcd. for C$_{17}$H$_{13}$N$_3$O$_3$S (M$^+$): 339.0678, Found: 339.0673. |
| 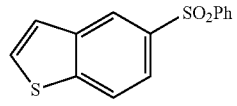<br>bromide: 2 mol %CuI/<br>2 mol %L-105, 100° C.<br>yield: 94% | $^1$H NMR (500 MHz, DMSO-d6) δ = 8.60 (s, 1H), 8.24 (d, J = 8.5, 1H), 8.00 (d, J = 7.9, 2H), 7.96 (d, J = 5.5, 1H), 7.86 (d, J = 8.6, 1H), 7.68-7.61 (m, 2H), 7.59 (t, J = 7.6, 2H). $^{13}$C NMR (126 MHz, DMSO-d6) δ 143.91, 141.49, 139.35, 137.27, 133.46, 130.71, 129.63, 127.20, 124.52, 124.08, 123.31, 121.82. |

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A method for coupling reaction of an aryl halide, comprising: carrying out the coupling reaction by using copper as a catalyst and a compound of following formula I as a ligand:

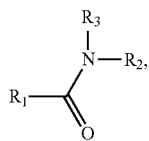

wherein $R_1$ is selected from the group consisting of: a substituted or unsubstituted pyrrole and a substituted or unsubstituted indole;

$R^2$ is selected from the group consisting of: a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein the heteroaryl or heterocyclic group has 1 to 5 hetero atoms selected from the group consisting of: N, O and S; the cycloalkyl or heterocyclic group may be of monocyclic, multiple-cyclic, Spiro or bridged ring structure;

$R_3$ is selected from the group consisting of: hydrogen, and a substituted or unsubstituted C1-C6 alkyl;

or $R_2$ and $R_3$ together with the connected N atom to form a substituted or unsubstituted pyrrole or a substituted or unsubstituted indole;

wherein the aryl halide is an aryl chloride.

2. The method of claim 1, wherein in the coupling reaction, the molar ratio of the ligand to the reactant aryl halide is 1-50:100; and/or the molar ratio of the ligand to the copper catalyst is 1-5:1.

3. The method of claim 1, wherein the reaction comprises:

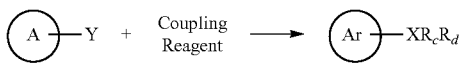

in an inert solvent, reacting

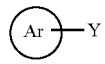

with a coupling reagent to obtain compound

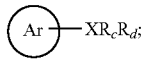

wherein X is selected from the group consisting of: N, O and S;
Y is selected from the group consisting of: Cl, Br, and I;

is selected from the group consisting of: a substituted or unsubstituted C6-C20 aryl, substituted or unsubstituted 3- to 20-membered heteroaryl; wherein the "substituted" means that one or more hydrogen atoms on the aryl group is substituted by a substituent selected from the group consisting of: halogen, nitro, cyano, amino which is unsubstituted or substituted with 1 or 2 C1-C6 alkyl or C2-C10 acyl (alkyl-CO—), hydroxy, unsubstituted or halogenated C1-C6 alkyl, C1-C6 alkoxy, C6-C10 aryl, 3- to 20-membered heteroaryl, C6-C10 aryl-oxy, C2-C10 ester group (alkyl-COO—), C2-C10 acyl group (alkyl-CO—), C2-C10 acyl-alkoxy group (alkyl-OOC—), C2-C10 amide group (alkyl-NHC(O)—, aryl-NHC(O)—), —COOH, hydroxy-C1-C10 alkylene, MeS—, sulfonyl, sulfamine; wherein two hydrogen atoms on adjacent carbon atoms of the aryl may be substituted by —(CH2)n- (n is 1, 2, 3, 4, 5 or 6);
the coupling reagent is selected from the group consisting of: ammonia water, ammonia gas, ammonium salt/hydroxide solution,

(number of carbon atom is 2-20), $R_eC(O)NHR_d$, $R_cSO_2M$, sodium azide, $NHR_cR_d$, $R_cOH$, $R_cSH$, hydroxide, and salts that can be hydrolyzed to form hydroxide, wherein M is sodium or potassium;
$R_c$, $R_d$, $R_e$ are each independently selected from the group consisting of: H, a substituted or unsubstituted C1-C6 alkyl, substituted or unsubstituted C1-C6 alkenyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl group, substituted or unsubstituted C1-C5 alkyl-(C3-C20 cycloalkyl group), substituted or unsubstituted 3- to 20-membered heterocyclic group, and substituted or unsubstituted C1-C5 alkyl-(3- to 20-membered heterocyclic group);
or $R_c$ and $R_d$ together form a substituted or unsubstituted C3-C20 cycloalkyl, substituted or unsubstituted 3- to 20-membered heterocyclic group;
or $R_e$ and $R_d$ together form a substituted or unsubstituted C3-C20 cycloalkyl, substituted or unsubstituted 3- to 20-membered heterocyclic group;
wherein the heteroaryl or heterocyclic group has 1 to 5 heteroatoms selected from the group consisting of: N, O and S; the cycloalkyl or heterocyclic group may be of monocyclic, multiple cyclic, spiral or bridged ring structure;
the "substituted" means that one or more hydrogen atoms on the group are substituted by a substituent selected from the group consisting of: halogen, cyano, oxygen (i.e., two hydrogen atoms on the same carbon atom on the group are replaced by =O), a C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 amide group (alkyl/aryl NHC(O)—), —COOH, nitro, hydroxy, amino, amino substituted by 1 or 2 C1-C6 alkyl groups, C1-C6 alkyl-S—.

4. The method of claim 1, wherein the reaction temperature is 50-180° C.

5. The method of claim 1, wherein the reaction comprises (1), (2), (3), (4) or (5):
(1) reacting

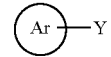

with $NHR_cR_d$ in an inert solvent to give

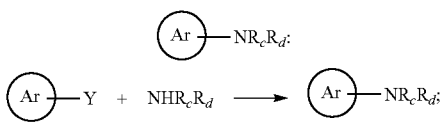

wherein the groups are defined as above;
(2) reacting

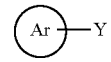

with ammonia source in an inert solvent to obtain

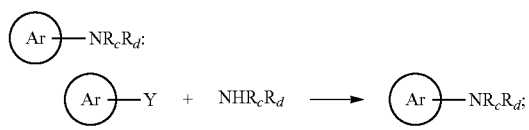

wherein the groups are defined as above;
the ammonia source is selected from the group consisting of: ammonia gas, ammonium hydroxide, ammonium chloride, ammonium carbonate, ammonium hydrogen carbonate, ammonium sulfate, ammonium nitrate, ammonium phosphate, diammonium hydrogen phosphate, and sodium azide;

(3) in an inert solvent, reacting

with $R_cOH$ to provide

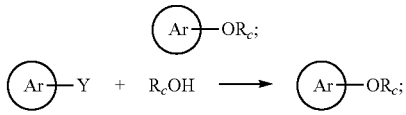

wherein the groups are defined as above;

(4) in an inert solvent, reacting

with $R_cSO_2M$ to provide

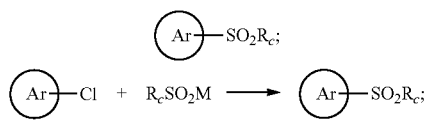

wherein the groups are defined as above;

(5) in an inert solvent, reacting

with $R_cSH$ to provide

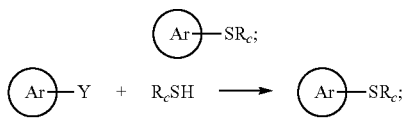

wherein the groups are defined as above.

6. The method of claim 1 wherein the copper catalyst is selected from the group consisting of: CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, and combinations thereof.

7. The method of claim 1, wherein the reaction is carried out in the presence of a base selected from the group consisting of: potassium carbonate, cesium carbonate, potassium phosphate, sodium bicarbonate, potassium bicarbonate, sodium carbonate, sodium hydroxide, potassium hydroxide, lithium hydroxide, sodium acetate, and combinations thereof.

8. The method of claim 5, wherein,
in the reaction (1), the ligand is

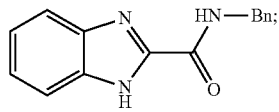 [SMILES: O=C(NCc1ccccc1)c1nc2ccccc2[nH]1]

in the reaction (2), the ligand is selected from the group consisting of:

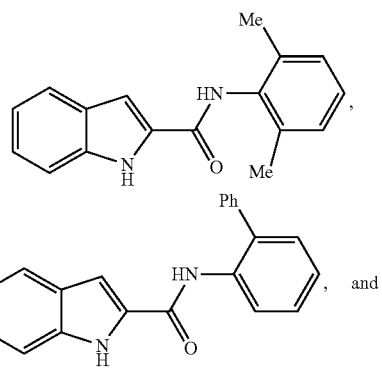

in the reaction (3), the ligand is selected from the group consisting of:

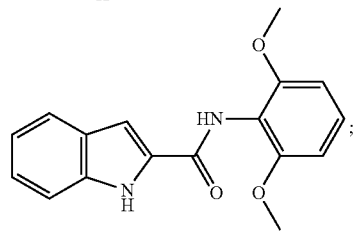

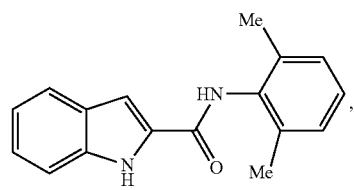 [SMILES: Cc1cccc(C)c1NC(=O)c1cc2ccccc2[nH]1]

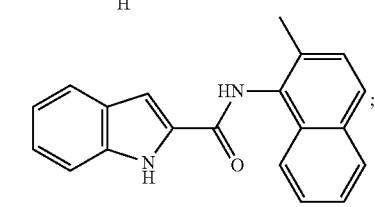

or
in the reaction (5), the ligand is

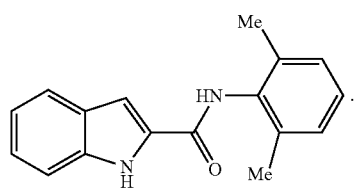

9. The method of claim 1, wherein the compound is of following formula II structure:

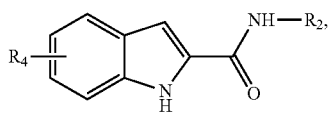

wherein R₂ is selected from the group consisting of: a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of: N, O and S; the cycloalkyl or heterocyclic group may be of monocyclic, multiple-cyclic, spiro or bridged ring structure;

R₄ is selected from the group consisting of: H, nitro, halogen, a substituted or unsubstituted C1-C6 alkyl, alkoxy (such as C1-C6 alkoxy), substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, and substituted or unsubstituted 3- to 20-membered heterocyclic group; wherein said heteroaryl or heterocyclic group has 1-5 heteroatoms selected from the group consisting of: N, O and S; the cycloalkyl or heterocyclic group may be of monocyclic, multiple-cyclic, Spiro or bridged ring structure;

or, the compound is of following formula III structure:

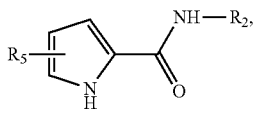

wherein R₂ is selected from the group consisting of: a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of: N, O and S; the cycloalkyl or heterocyclic group may be of monocyclic, multiple-cyclic, spiro or bridged ring structure;

R₅ is selected from the group consisting of: H, nitro, halogen, a substituted or unsubstituted C1-C6 alkyl, C1-C6 alkoxy, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-(3- to 20-membered heteroaryl), substituted or unsubstituted C3-C20 cycloalkyl, or substituted or unsubstituted 3- to 20-membered heterocyclic group; wherein said heteroaryl or heterocyclic group has 1-5 heteroatoms selected from the group consisting of: N, O and S; the cycloalkyl or heterocyclic group may be of monocyclic, multiple-cyclic, spiro or bridged ring structure; wherein the number of R₅ substituent is 1-3, wherein the substitution position may be ortho or meta, and wherein each R₅ may be the same or different; where the number of R₅ substituent is ≤2, the adjacent R₅ may be linked to form a ring.

10. The method of claim 1, wherein the ligand is selected from the group consisting of:

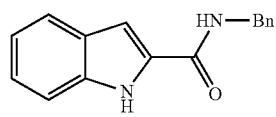

L-1

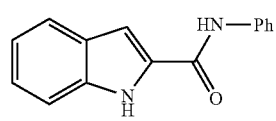

L-2

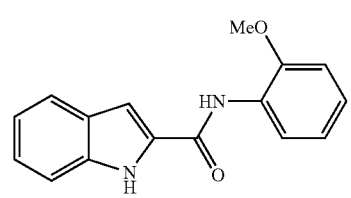

L-3

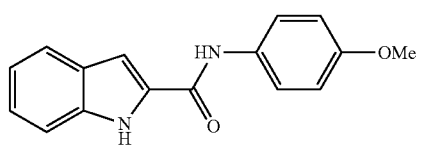

L-4

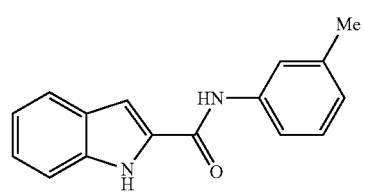

L-5

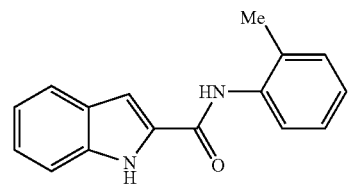

L-6

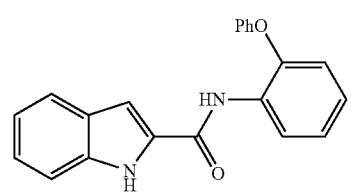

L-7

L-8
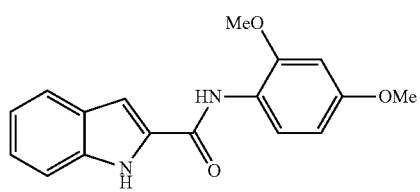
L-9
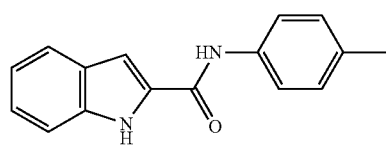
L-10
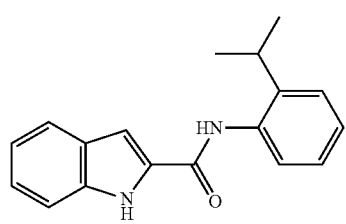
L-11
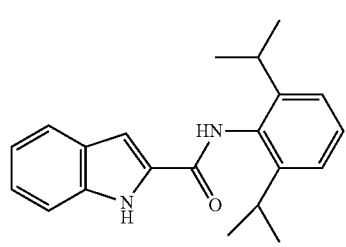
L-12
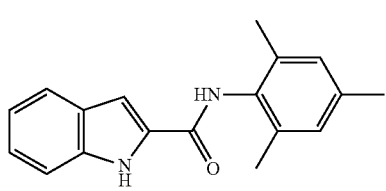
L-13
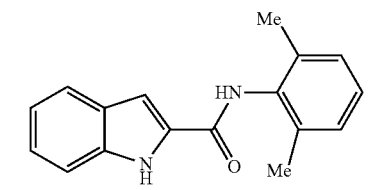
L-14
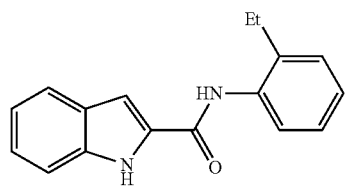
L-15
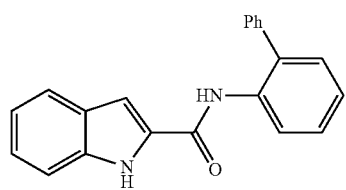
L-16
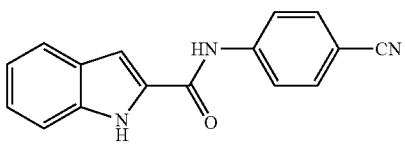
L-17
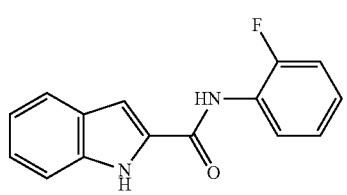
L-18
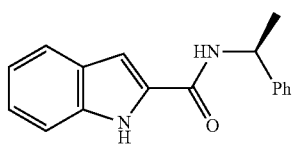
L-19
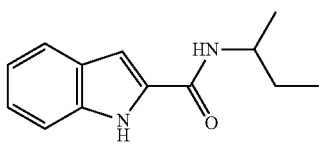
L-20
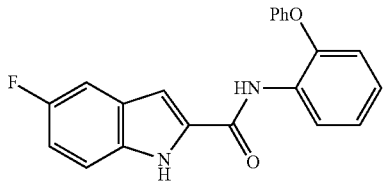
L-21
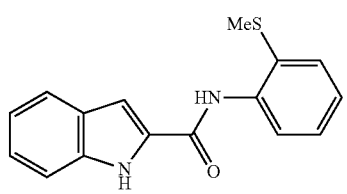
L-22
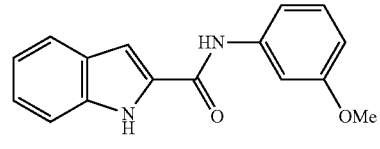
L-23
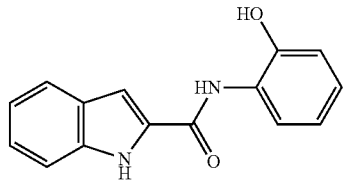
L-24
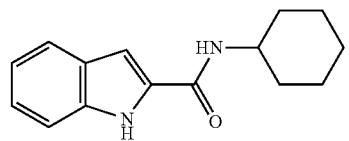

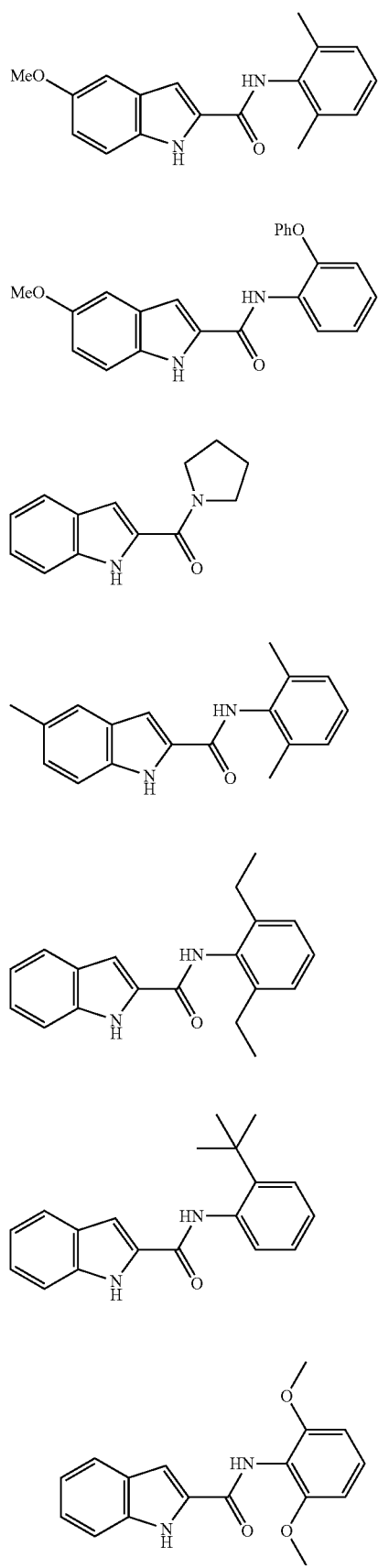
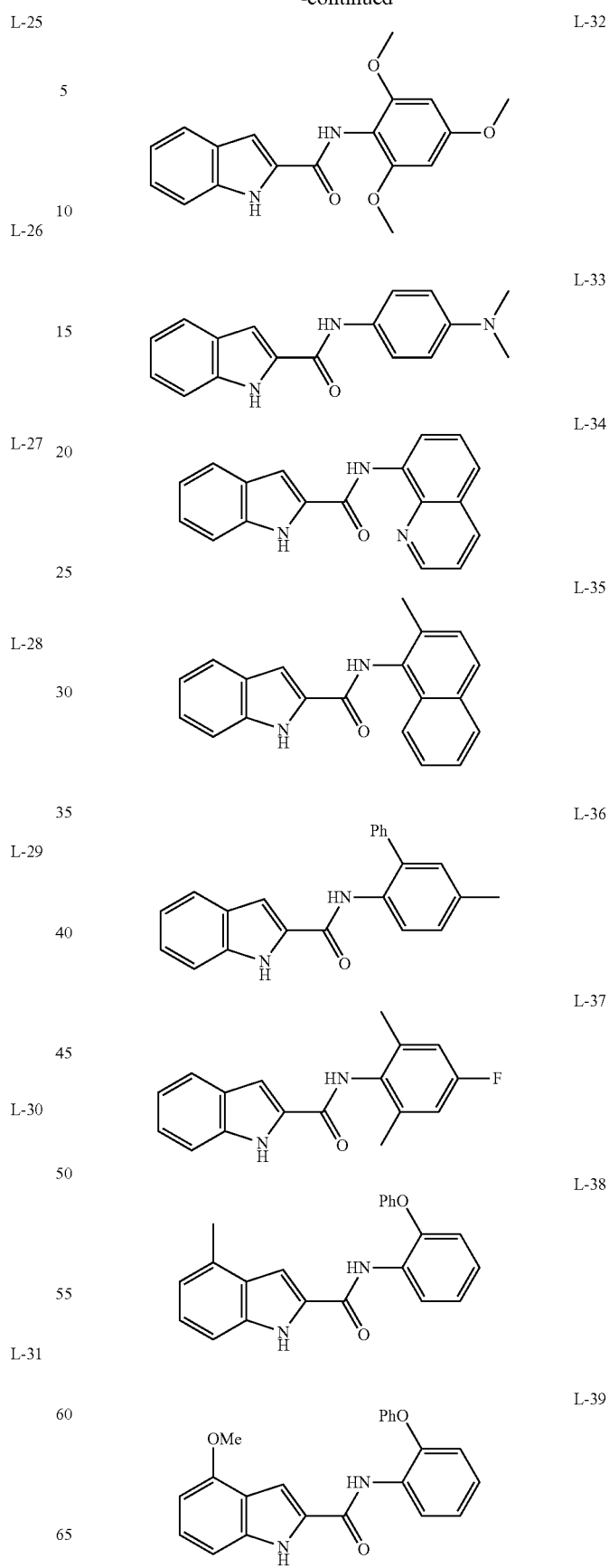

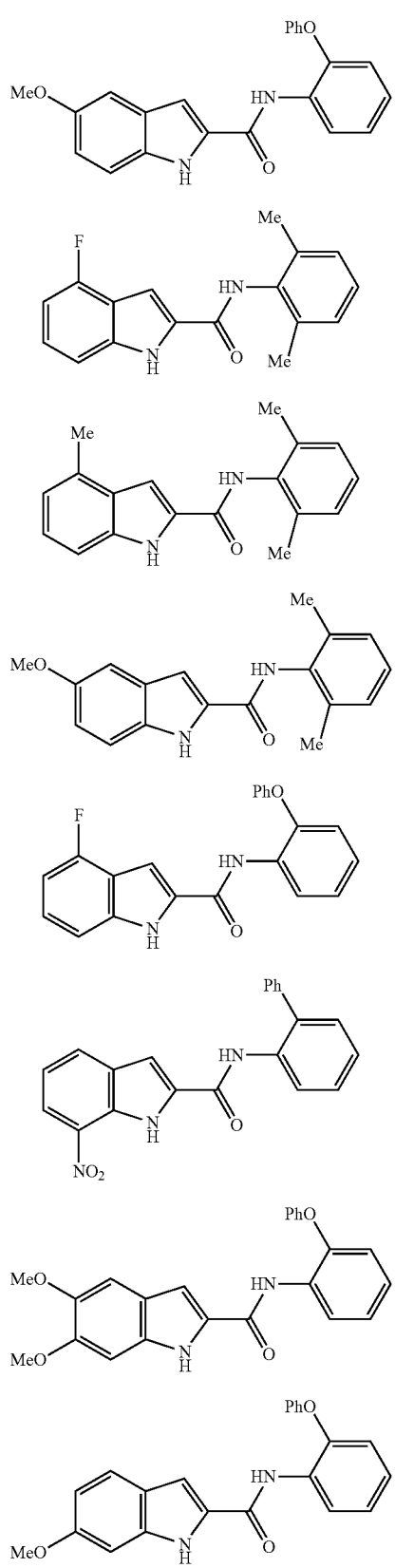

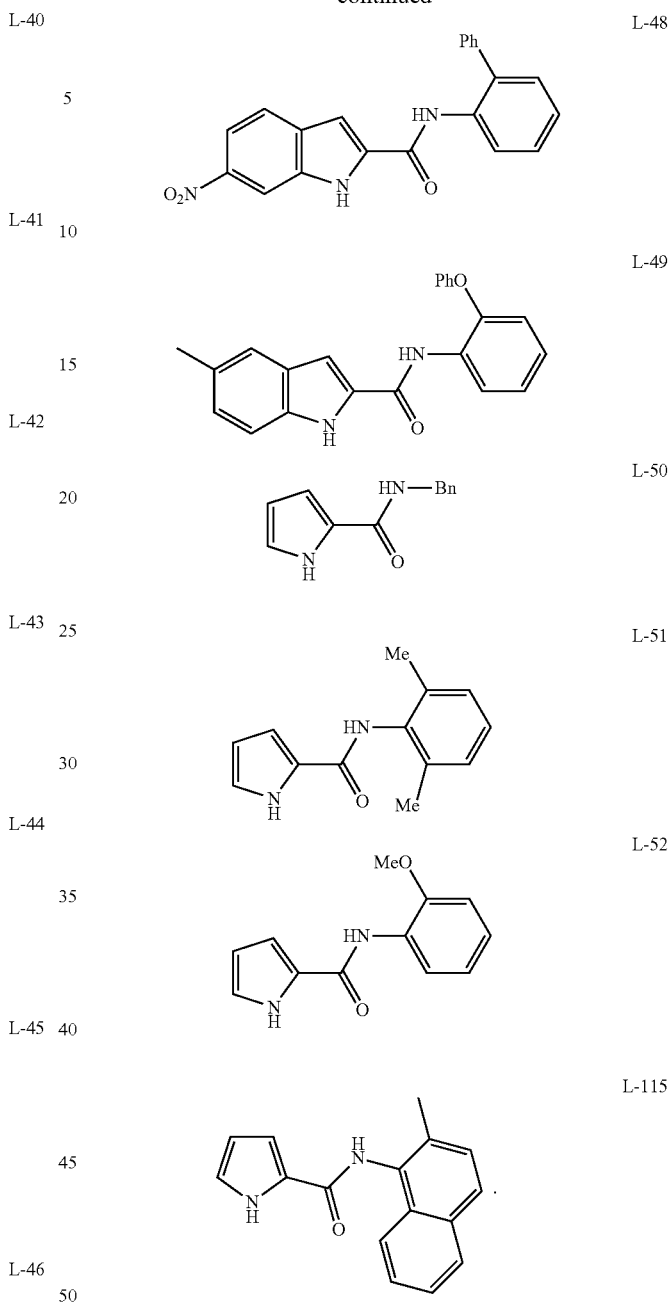

11. The method of claim 2, wherein in the coupling reaction, the molar ratio of the ligand to the reactant aryl halide is 5-20:100; and/or the molar ratio of the ligand to the copper catalyst is 1-2:1.

12. The method of claim 4, wherein the reaction temperature is 100-130° C.

13. The method of claim 5, wherein the ammonia source is selected from the group consisting of: ammonia gas, ammonium hydroxide, ammonium chloride, and diammonium hydrogen phosphate.

* * * * *